(12) United States Patent
Fukuda

(10) Patent No.: US 6,686,363 B2
(45) Date of Patent: Feb. 3, 2004

(54) CYCLOPROPYL CONTAINING OXAZOLIDINONE ANTIBIOTICS AND DERIVATIVES THEREOF

(75) Inventor: Yasumichi Fukuda, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 38 days.

(21) Appl. No.: 10/305,368

(22) Filed: Nov. 27, 2002

(65) Prior Publication Data

US 2003/0225107 A1 Dec. 4, 2003

Related U.S. Application Data

(60) Provisional application No. 60/333,741, filed on Nov. 29, 2001.

(51) Int. Cl.$^7$ .................. A61K 31/495; C07D 40/102; A61P 43/00

(52) U.S. Cl. .................. 514/255.05; 514/362; 514/363; 514/364; 514/369; 514/374; 514/376; 548/125; 548/127; 548/128; 548/131; 548/138; 548/143; 548/196; 544/405

(58) Field of Search ................... 514/364, 369, 514/362, 363, 376, 255.05, 374; 548/131, 143, 196, 127, 125, 128, 138, 229, 232; 544/405

(56) References Cited

U.S. PATENT DOCUMENTS 6,069,160 A   5/2000   Stolle et al.

FOREIGN PATENT DOCUMENTS

EP   0 657 440 A1   12/1994
WO   WO 96/35691   11/1996

OTHER PUBLICATIONS

"Recent developments with oxazolidinone antibiotics", Bernd Riedl et al., Expert Opinion on Therapeutic Patents, Ashley Publications Ltd., 1999, pp. 625–633, ISSN 1354–3776.

"Oxazolidinones: new bacterial agents", Charles W. Ford, Trends in Microbiology, vol. 5, No. 5, May 1997, pp. 196–200.

Primary Examiner—Joseph K. McKane
Assistant Examiner—Andrea D. Small
(74) Attorney, Agent, or Firm—McDermott, Will & Emery

(57) ABSTRACT

This invention relates to new oxazolidinones having a cyclopropyl moiety, which are effective against aerobic and anerobic pathogens such as multi-resistant staphylococci, streptococci and enterococci, Bacteroides spp., Clostridia spp. species, as well as acid-fast organisms such as *Mycobacterium tuberculosis* and other mycobacterial species. The compounds are represented by structural formula I:

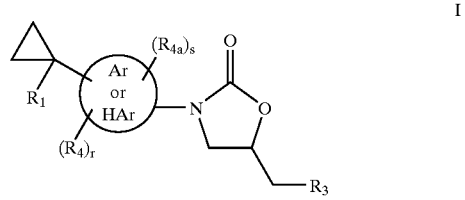

its enantiomer, diastereomer, or pharmaceutically acceptable salt or ester thereof.

32 Claims, No Drawings

CYCLOPROPYL CONTAINING OXAZOLIDINONE ANTIBIOTICS AND DERIVATIVES THEREOF

CROSS REFERENCE TO RELATED APPLICATIONS

This application claims priority from U.S. Provisional Application Serial No. 60/333,741, filed Nov. 29, 2001.

BACKGROUND OF THE INVENTION

Oxazolidinones represent the first new class of antibacterials to be developed since the quinolones. The oxazolidinones are synthetic antibacterial compounds that are orally or intravenously active against problematic multidrug resistant Gram positive organisms and are not cross-resistant with other antibiotics. See Riedl et al, Recent Developments with Oxazolidinone Antibiotics, *Exp. Opin. Ther. Patents* (1999) 9(5), Ford et al., Oxazolidinones: New Antibacterial Agents, *Trends in Microbiology* 196 Vol. 5, No. 5, May 1997 and WO 96/35691.

This invention relates to new oxazolidinones having a cyclopropyl moiety, which are effective against aerobic and anerobic pathogens such as multi-resistant staphylococci, streptococci and enterococci, Bacteroides spp., Clostridia spp. species, as well as acid-fast organisms such as *Mycobacterium tuberculosis* and other mycobacterial species.

SUMMARY OF THE INVENTION

The present invention relates to compounds of formula I:

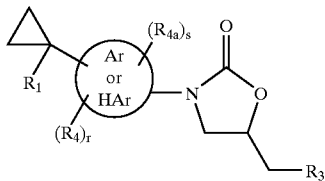

its enantiomer, diastereomer, or pharmaceutically acceptable salt, hydrate or prodrug thereof wherein:

$R_1$ represents
  i) hydrogen,
  ii) $NR_5NR_6$,
  iii) $CR_7R_8R_9$, $C(R)_2OR_{14}$, $CH_2NHR_{14}$, $C(=O)R_{13}$, $C(=NOH)H$, $C(=NOR_{13})H$, $C(=NOR_{13})R_{13}$, $C(=NOH)R_{13}$, $C(=O)N(R_{13})_2$, $C(=NOH)N(R_{13})_2$, $NHC(=X_1)N(R_{13})_2$, $(C=NH)R_7$, $N(R_{13})C(=X_1)N(R_{13})_2$, $COOR_{13}$, $SO_2R_{14}$, $N(R_{13})SO_2R_{14}$, $N(R_{13})COR_{14}$, or $(C_{1-6}alkyl)CN$, CN, $CH=C(R)_2$, OH, $C(=O)CHR_{13}$, $C(=NR_{13})R_{13}$, $NHC(=X_1)R_{13}$; or
  iv) $C_{5-10}$ heterocycle optionally substituted with 1–3 groups of $R_7$, which may be attached through either a carbon or a heteroatom;

represents aryl or heteroaryl, heterocycle, heterocyclyl or heterocyclic, provided that in the case of a heteroaryl, heterocycle, heterocyclyl or heterocyclic, the cyclopropyl is not attached to a nitrogen atom on the ring;

$R_3$ represents
  i) $NR_{13}(C=X_2)R_{12}$,
  ii) $NR_{13}(C=X_1)R_{12}$,
  iii) $NR_{13}SO_2R_{14}$,
  iv) $NR_{13}(CHR_{13})_{0-4}aryl$,
  v) $NR_{13}(CHR_{13})_{0-4}heteroaryl$,
  vi) $S(CHR_{13})_{0-4}aryl$,
  vii) $S(CHR_{13})_{0-4}heteroaryl$,
  viii) $O(CHR_{13})_{0-4}aryl$, or
  ix) $O(CHR_{13})_{0-4}heteroaryl$;
  x) $OCR_{13}=NR_{16}$
  xi)

$R_4$ and $R_{4a}$ independently represent
  i) hydrogen,
  ii) halogen,
  iii) $C_{1-6}$ alkoxy,
  iv) $C_{1-6}$ alkyl,
  v) CN,
  vi) Aryl, or
  vii) heteroaryl
r and s independently are 1–3, with the provision that when $(R_{4a})_s$ and $(R_4)_r$ are attached to an Ar or HAr ring the sum of r and s is less than or equal to 4;

represents an optionally substituted aromatic heterocyclic group containing at least one nitrogen in the ring and which is attached through a bond on any N, and which is unsubstituted or contains 1 to 3 substituents of $R_{16}$;

$R_5$ and $R_6$ independently represent
  i) hydrogen,
  ii) $C_{1-6}$ alkyl optionally substituted with 1–3 groups of halogen, CN, OH, $C_{1-6}$ alkoxy, amino, imino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethylenyloxy, or ethynyl, said phenyl and pyridine optionally substituted with 1–3 halogen, CN, OH, $CF_3$, $C_{1-6}$ alkyl or $C_{1-6}$ alkoxy;
  iii) $C_{1-6}$ acyl optionally substituted with 1–3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, aralkyloxy, phenyl, pyridine, $C_{1-6}$ alkylcarbonyl, $C_{1-6}$ alkylamino, $C_{1-6}$ dialkylamino, $C_{1-6}$ hydroxyacyloxy, $C_{1-6}$ alkylsulfenyl, phthalimido, maleimido, succinimido, said phenoxy, phenyl and pyridine optionally substituted with 1–3 groups of halo, OH, CN, $C_{1-6}$ alkoxy, amino, $C_{1-6}$ acylamino, $CF_3$ or $C_{1-6}$ alkyl;
  iv) $C_{1-6}$ alkylsulfonyl optionally substituted with 1–3 groups of halogen, OH, $C_{1-6}$ alkoxy, amino, hydroxylamino, alkoxylamino, $C_{1-6}$ acyloxy, or phenyl; said phenyl optionally substituted with 1–3 groups of halo, OH, $C_{1-6}$ alkoxy, amino, $C_{1-6}$ acylamino, $CF_3$ or $C_{1-6}$ alkyl;
  v) arylsulfonyl optionally substituted with 1–3 of halogen, $C_{1-6}$ alkoxy, OH or $C_{1-6}$ alkyl;

vi) $C_{1-6}$ alkoxycarbonyl optionally substituted with 1–3 of halogen, OH, $C_{1-6}$ alkoxy, $C_{1-6}$ acyloxy, or phenyl, said phenyl optionally substituted with 1–3 groups of halo, OH, $C_{1-6}$ alkoxy, amino, $C_{1-6}$ acylamino, $CF_3$ or $C_{1-6}$ alkyl;

vii) aminocarbonyl, $C_{1-6}$ alkylaminocarbonyl or $C_{1-6}$ dialkylaminocarbonyl, said alkyl groups optionally substituted with 1–3 groups of halogen, OH, $C_{1-6}$ alkoxy or phenyl;

viii) five to six membered heterocycles optionally substituted with 1–3 groups of halogen, OH, CN, amino, $C_{1-6}$ acylamino, $C_{1-6}$ alkylsulfonylamino, $C_{1-6}$ alkoxycarbonylamino, $C_{1-6}$ alkoxy, $C_{1-6}$ acyloxy or $C_{1-6}$ alkyl, said alkyl optionally substituted with 1–3 groups of halogen, or $C_{1-6}$ alkoxy;

ix) $C_{3-6}$ cycloalkylcarbonyl optionally substituted with 1–3 groups of halogen, OH, $C_{1-6}$ alkoxy or CN;

x) benzoyl optionally substituted with 1–3 groups of halogen, OH, $C_{1-6}$ alkoxy, $C_{1-6}$ alkyl, $CF_3$, $C_{1-6}$ alkanoyl, amino or $C_{1-6}$ acylamino;

xi) pyrrolylcarbonyl optionally substituted with 1–3 of $C_{1-6}$ alkyl;

xii) $C_{1-2}$ acyloxyacetyl where the acyl is optionally substituted with amino, $C_{1-6}$ alkylamino, $C_{1-6}$ dialkylamino, 4-morpholino, 4-aminophenyl, 4-(dialkylamino)phenyl, 4-(glycylamino)phenyl; or $R_5$ and $R_6$ taken together with any intervening atoms can form a 3 to 7 membered heterocyclic ring containing carbon atoms and 1–2 heteroatoms independently chosen from O, S, SO, $SO_2$, N, or $NR_8$;

$R_7$ represents
i) hydrogen, halogen, OH, $C_{1-6}$ alkoxy, $C_{1-6}$ alkyl, alkenyl,
ii) amino, $C_{1-6}$ alkylamino, $C_{1-6}$ dialkylamino, hydroxylamino or $C_{1-2}$ alkoxyamino all of which can be optionally substituted on the nitrogen with $C_{1-6}$ acyl, $C_{1-6}$ alkylsulfonyl or $C_{1-6}$ alkoxycarbonyl, said acyl and alkylsulfonyl optionally substituted with 1–2 of halogen or OH;

$R_8$ and $R_8$ independently represent
i) H, CN,
ii) $C_{1-6}$ alkyl optionally substituted with 1–3 halogen, CN, OH, $C_{1-6}$ alkoxy, $C_{1-6}$ acyloxy, or amino,
iii) phenyl optionally substituted with 1–3 groups of halogen, OH, $C_{1-6}$ alkoxy; or $R_7$ and $R_8$ taken together can form a 3–7 membered carbon ring optionally interrupted with 1–2 heteroatoms chosen from O, S, SO, $SO_2$, NH, and $NR_8$;

$X_1$ represents O, S or $NR_{13}$, NCN, or $NSO_2R_{14}$;
$X_2$ represents O, S, NH or $NSO_2R_{14}$;
$R_{10}$ represents hydrogen, $C_{1-6}$ alkyl or $CO_2R_{15}$;
$R_{11}$ represents hydrogen, $C_{1-6}$ alkyl, $C_{1-6}$ alkanoyl, halogen, amino, $C_{1-6}$ acylamino, $C_{1-6}$ alkoxy, OH or $CF_3$,; $NHC_{1-6}$ alkyl, or $N(C_{1-6}$ alkyl$)_2$, where said alkyl may be substituted with 1–3 groups of halo, OH or $C_{1-6}$ alkoxy;
$R_{12}$ represents hydrogen, $C_{1-6}$ alkyl, $C_{1-6}$ cycloalkyl, heteroaryl, wherein said heteroaryl may be substituted with 1–2 groups of $C_{1-6}$ alkyl, $NH_2$, $C_{1-6}$ alkylamino, $C_{1-6}$ alkoxy or $C_{1-6}$ dialkylamino, where said alkyl may be substituted with 1–3 groups of halo, OH or $C_{1-6}$ alkoxy; alkylthio, alkylsulfinyl, alkylsulfonyl or cyano;

Each $R_{13}$ represents independently hydrogen, $C_{1-6}$ alkyl, $NR_5R_6$, $SR_8$, $S(O)R_8$, $S(O)_2R_8$, CN, $C_{1-6}$ alkylS(O)R, OH, $C_{1-6}$ alkoxycarbonyl, $C_{6-10}$ arylcarboxy, hydroxycarbonyl, $C_{1-6}$ acyl, $C_{3-7}$ membered carbon ring optionally interrupted with 1–4 heteroatoms chosen from O, S, SO, $SO_2$, NH and $NR_8$ where said $C_{1-6}$ alkyl or $C_{1-6}$ acyl groups may be independently substituted with 0–3 halogens, hydroxy, $N(R)_2$, $CO_2R$, $C_{6-10}$ aryl, $C_{5-10}$ heteroaryl, or $C_{1-6}$ alkoxy groups;

When two $R_{13}$ groups are attached to the same atom or two adjacent atoms they may be taken together to form a 3–7 membered carbon ring optionally interrupted with 1–2 heteroatoms chosen from O, S, SO, $SO_2$, NH, and $NR_8$;

R represents hydrogen or $C_{1-6}$ alkyl;

$R_{14}$ represents amino, $C_{1-6}$ alkyl, $C_{1-6}$ haloalkyl, five to six membered heterocycles or phenyl, said phenyl and heterocycles optionally substituted with 1–3 group of halo, $C_{1-6}$ alkoxy, $C_{1-6}$ acylamino, or $C_{1-6}$ alkyl, hydroxy and/or amino, said amino and hydroxy optionally protected with an amino or hydroxy protecting group;

$R_{15}$ is $C_{1-6}$ alkyl or benzyl said benzyl optionally substituted with 1–3 groups of halo, OH, $C_{1-6}$ alkoxy, amino, $C_{1-6}$ acylamino, or $C_{1-6}$ alkyl;

$R_{16}$ represents CN, $NH_2$, OH, hydroxy $C_{1-6}$ alkyl, $C_{1-6}$ alkyl, $COOC_{1-6}$ alkyl, COOH, $CONH_2$, $CON(C_{1-6}$ alkyl$)_2$, $CONHC_{1-6}$ alkyl, CHO, C=NOH, C=NOC$_{1-6}$ alkyl, $(CH_2)_{1-3}NH_2$, $(CH_2)_{1-6}NHOC_{1-6}$ alkyl, $(CH_2)_{1-6}N(C_{1-6}$ alkyl$)_2$, m, n, and q represents 0–1.

Another aspect of the invention is concerned with the use of the novel antibiotic compositions in the treatment of bacterial infections.

DETAILED DESCRIPTION OF THE INVENTION

The invention is described herein in detail using the terms defined below unless otherwise specified.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen Stereochemistry of Carbon Compounds (John Wiley and Sons, New York 1994, in particular pages 1119–1190).

When any variable (e.g. aryl, heterocycle, $R_5$, $R_6$ etc.) occurs more than once, its definition on each occurrence is independent at every other occurrence. Also combinations of substituents/or variables are permissible only if such combinations result in stable compounds.

The term "alkyl" refers to a monovalent alkane (hydrocarbon) derived radical containing from 1 to 15 carbon atoms unless otherwise defined. It may be straight or branched. Preferred alkyl groups include lower alkyls which have from 1 to 6 carbon atoms such as methyl, ethyl, propyl, isopropyl, butyl and t-butyl. When substituted, alkyl groups may be substituted with up to 3 substituent groups, selected from the groups as herein defined, at any available point of attachment. When the alkyl group is said to be substituted with an alkyl group, this is used interchangeably with "branched alkyl group".

Cycloalkyl is a species of alkyl containing from 3 to 15 carbon atoms, without alternating or resonating double bonds between carbon atoms. It may contain from 1 to 4 rings which are fused. Preferred cycloalkyl groups are cyclopropyl, cyclobutyl, cyclopentyl and cyclohexyl. When substituted, cycloalkyl groups may be substituted with up to 3 substituents which are defined herein by the definition of alkyl.

Alkanoyl refers to a group derived from an aliphatic carboxylic acid of 2 to 4 carbon atoms. Examples are acetyl, propionyl, butyryl and the like.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

refers to aryl or heteroaryl, heterocycle, Het, heterocyclyl or heterocyclic as described immediately below.

Aryl refers to any stable monocyclic or bicyclic carbon ring of up to 7 atoms in each ring, wherein at least one ring is aromatic. Examples of such aryl elements include phenyl, naphthyl, tetrahydronaphthyl, indanyl, indanonyl, biphenyl, tetralilnyl, tetralonyl, fluorenonyl, phenanthryl, anthryl, acenaphthyl, and the like substituted phenyl and the like. Aryl groups may likewise be substituted as defined. Preferred substituted aryls include phenyl and naphthyl.

The expression

represents an optionally substituted aromatic heterocyclic group containing 1 to 4 ntrogen atoms and at least one double bond, and which is connected through a bond on any nitrogen. Exemplary groups are 1,2,3-triazole, 1,2,4-triazole, 1,2,5-triazole, tetrazole, pyrazole, and imidazole, any of which may contain 1 to 3 substituents selected from CN, $NH_2$, OH, $C_{1-6}$ alkyl, $COOC_{1-6}$ alkyl, COOH, $CONH_2$, $CON(C_{1-6}$ alkyl$)_2$, $CONH(C_{1-6}$ alkyl), CHO, $C=NOC_{1-6}$ alkyl, $(CH_2)_{1-3}NH_2$, NHAc, or $N(C_{1-6}$ alkyl$)_2$.

The term heterocycle, heteroaryl, Het, heterocyclyl or heterocyclic, as used herein except where noted, represents a stable 5- to 7-membered mono- or bicyclic or stable 8- to 11-membered bicyclic heterocyclic ring system, any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized (in which case it is properly balanced by a counterion), and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. "Heterocycle" or "heterocyclyl" therefore includes the above mentioned heteroaryls, as well as dihydro and tetrahydro analogs thereof. The heterocycle, heteroaryl, Het or heterocyclic may be substituted with 1–3 groups of $R_7$. Examples of such heterocyclic elements include, but are not limited to the following: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyrimidonyl, pyridinonyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thiophenyl, imidazopyridinyl, tetrazolyl, triazinyl, thienyl, benzothienyl, thiamorpholinyl sulfoxide, thiamorpholinyl sulfone, naphthpyridinyl, dihydropyrimidinyl, dihydropyrrolyl, dihydroquinolinyl, dihydrotetrazolyl, dihydrotriazolyl, dihydrothienyl, dihydrooxazolyl, dihydrobenzothiophenyl, dihydrofuranyl, benzothiazolyl, benzothienyl, benzoimidazolyl, benzopyranyl, benzothiofuranyl, carbolinyl, chromanyl, cinnolinyl, benzopyrazolyl, benzodioxolyl and oxadiazolyl. Additional examples of heteroaryls are illustrated by formulas a, b, c and d:

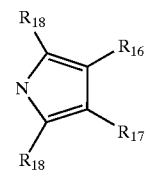

a

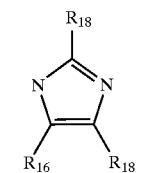

b

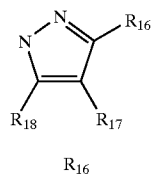

c

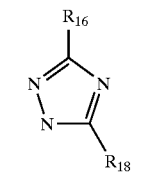

d wherein $R_{16}$ and $R_{17}$ are independently selected from hydrogen, halogen, $C_{1-6}$ alkyl, $C_{2-4}$ alkanoyl, $C_{1-6}$ alkoxy; and $R_{18}$ represents hydrogen, $C_{1-6}$ alkyl, $C_{2-4}$ alkanoyl, $C_{1-6}$ alkoxycarbonyl and carbamoyl.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The terms "quaternary nitrogen" and "positive charge" refer to tetravalent, positively charged nitrogen atoms (balanced as needed by a counterion known in the art) including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

The term "prodrug" refers to compounds which are drug precursors which, following administration and absorption, release the drug in vivo via some metabolic process. Exemplary prodrugs include acyl amides of the amino compounds of this invention such as amides of alkanoic($C_{1-6}$)acids, amides of aryl acids (e.g., benzoic acid) and alkane($C_{1-6}$) dioic acids.

Halogen and "halo" refer to bromine, chlorine, fluorine and iodine.

When a group is termed "substituted", unless otherwise indicated, this means that the group contains from 1 to 3 substituents thereon.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. Protective Groups in Organic Synthesis Wiley, New York (1991). Examples of suitable protecting groups are contained throughout the specification.

Examples of suitable hydroxyl and amino protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, allyloxycarbonyl and the like. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl, t-butyl and the like.

The cyclopropyl containing oxazolidinone compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel cyclopropyl containing oxazolidinone compounds.

The pharmaceutically acceptable salts referred to above also include acid addition salts. Thus, when the Formula I compounds are basic, salts may be prepared from pharmaceutically acceptable non-toxic acids, including inorganic or organic acids. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, isethionic, lactate, maleate, mandelic, malic, maleic, methanesulfonate, mucic, 2-naphthalenesulfonate, nicotinate, nitric oxalate, pamoate, pectinate, persulfate, 3-phenylpropionate, picrate, pivalate, propionate, phosphate, pantothenic, pamoic, sulfate, succinate, tartrate, thiocyanate, tosylate and undecanoate.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium zinc and the like. Particularly preferred are the ammonium, calcium, magnesium, potassium and sodium salts. Salts derived from pharmaceutically acceptable inorganic non-toxic bases include salts of primary, secondary and teritiary amines, substituted amines including naturally occurring substituted amines, cyclic amines and basic ion exchange resins, such as arginine, betaine caffeine, choline, $N,N^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The pharmaceutically acceptable esters are such as would be readily apparent to a medicinal chemist, and include those which are hydrolyzed under physiological conditions, such as "biolabile esters", pivaloyloxymethyl, acetoxymethyl, phthalidyl, indanyl and methoxymethyl, and others.

Biolabile esters are biologically hydrolizable, and may be suitable for oral administration, due to good absorption through the stomach or intenstinal mucosa, resistance to gastric acid degradation and other factors. Examples of biolabile esters include compounds.

Another embodiment of this invention is realized when $R_1$ independently represent H, $NR_5NR_6$, CN, OH, $C(R)_2OR_{14}$, $NHC(=X_1)N(R_{13})_2$, $C(=NOH)N(R_{13})_2$, or $CR_7R_8R_9$ and all other variables are as described herein.

Another embodiment of this invention is realized when

is phenyl, pyridine, pyrimidine, or piperidine and all other variables are as described herein.

Another embodiment of this invention is realized when $R_1$ is $NR_5R_6$ and all other variables are as described herein.

Another embodiment of this invention is realized when $R_1$ is CN and all other variables are as described herein.

Still another embodiment of this invention is realized when $R_5$ and $R_6$ independently are:
i) H,
ii) $C_{1-6}$ alkyl optionally substituted with 1–3 groups of halogen, CN, OH, $C_{1-6}$ alkoxy, amino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethyenyloxy, or ethynyl, said phenyl and pyridine optionally substituted with 1–3 halogen, CN, OH, CF$_3$, C$_{1-6}$ alkyl or C$_{1-6}$ alkoxy;

iii) C$_{1-6}$ acyl optionally substituted with 1–3 groups of halogen, OH, SH, C$_{1-6}$ alkoxy, naphthalenoxy, phenoxy, amino, C$_{1-6}$ acylamino, hydroxylamino, alkoxylamino, C$_{1-6}$ acyloxy, phenyl, pyridine, C$_{1-6}$ alkylcarbonyl, C$_{1-6}$ alkylamino, C$_{1-6}$ dialkylamino, C$_{1-6}$ hydroxyacyloxy, C$_{1-6}$ alkylsulfenyl, phthalimido, maleimido, succinimido, said phenoxy, phenyl and pyridine optionally substituted with 1–3 groups of halo, OH, CN, C$_{1-6}$ alkoxy, amino, C$_{1-6}$ acylamino, CF$_3$ or C$_{1-6}$ alkyl; or iv) benzoyl optionally substituted with 1–3 groups of halogen, OH, C$_{1-6}$ alkoxy, C$_{1-6}$ alkyl, CF$_3$, C$_{1-6}$ alkanoyl, amino or C$_{1-6}$ acylamino and all other variables are as described herein.

Yet another embodiment of this invention is realized when X$_1$ represents O and all other variables are as described herein.

A preferred embodiment of this invention is realized when the structural formula is II:

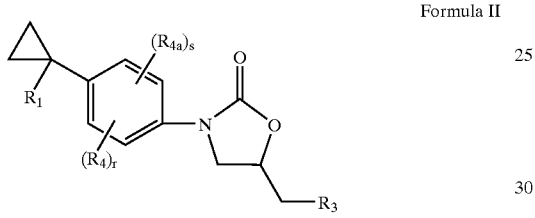

Formula II wherein R$_1$, R$_4$, R$_{4a}$, and R$_3$ are as described herein.

Another preferred embodiment of this invention is realized when R$_1$ is CN or NR$_5$R$_6$.

Preferred compounds of this invention are:

N-[5(S)-3-[4-[(1-t-Butoxycarbonyl)cyclopropan-1-yl]-3-fluorophenyl]-2-oxooxazolidin-5-ylmethyl]acetamide, N-[5(S)-3-[4-(1-Carboxycyclopropan-1-yl)-3-fluorophenyl]-2-oxooxazolidin-5-ylmethyl]acetamide, N-[5(S)-3-[3-Fluoro-4-(1-hydroxymethylcyclopropan-1-yl)phenyl]-2-oxooxazolidin-5-ylmethyl]acetamide, N-[5(S)-3-[4-(1-Aminocyclopropan-1-yl)-3-fluorophenyl]-2-oxooxazolidin-5-ylmethyl]acetamide, N-[5(S)-3-[4-(1-Aminocyclopropan-1-yl)-3,5-difluorophenyl]-2-oxooxazolidin-5-ylmethyl]acetamide, N-[5(S)-3-[4-(1-Aminocyclopropan-1-yl)phenyl]-2-oxooxazolidin-5-ylmethyl]acetamide, N-[5(S)-3-[3-Fluoro-4-(1-formylcyclopropan-1-yl)phenyl]-2-oxooxazolidin-5-ylmethyl]acetamide, N-[5(S)-3-[3-Fluoro-4-(1-(hydroxyimino)methylcyclopropan-1-yl)phenyl]-2-oxooxazolidin-5-ylmethyl]acetamide, N-[5(S)-3-[4-(1-Cyanocyclopropan-1-yl)-3-fluorophenyl]-2-oxooxazolidin-5-ylmethyl]acetamide, N-[5(S)-3-[4-(1-Cyanocyclopropan-1-yl)-3-fluorophenyl]-2-oxooxazolidin-5-ylmethyl]thioacetamide, N-[5(S)-3-[4-(1-Cyanocyclopropan-1-yl)-3,5-difluorophenyl]-2-oxooxazolidin-5-ylmethyl]thioacetamide, N-[5(S)-3-[4-(1-Cyanocyclopropan-1-yl)-3-fluorophenyl]-2-oxooxazolidin-5-ylmethyl]methanesulfonylamide, N-[5(S)-3-[4-[(1-t-Butoxycarbonyl)cyclopropan-1-yl]-3,5-difluorophenyl]-2-oxooxazolidin-5-ylmethyl]acetamide, N-[5(S)-3-[3,5-Difluoro-4-(1-hydroxymethylcyclopropan-1-yl)phenyl]-2-oxooxazolidin-5-ylmethyl]acetamide, N-[5(S)-3-[3,5-Difluoro-4-(1-formylcyclopropan-1-yl)phenyl]-2-oxooxazolidin-5-ylmethyl]acetamide, N-[5(S)-3-[4-(1-Cyanocyclopropan-1-yl)-3,5-difluorophenyl]-2-oxooxazolidin-5-ylmethyl]acetamide, N-[5(S)-3-[4-(1-Cyanocyclopropan-1-yl)-3-fluorophenyl]-2-oxooxazotidin-5-ylmethyl]difluoroacetamide, N-[5(S)-3-[4-(1-Cyanocyclopropan-1-yl)-3,5-difluorophenyl]-2-oxooxazolidin-5-ylmethyl]difluoroacetamide, N-[5(S)-3-[4-(1-Cyanocyclopropan-1-yl)phenyl]-2-oxooxazolidin-5-ylmethyl]difluoroacetamide, 5(S)-5-[N-(t-Butoxycarbonyl)-N-(1,2,4-oxadiazolyl-3-yl)]-3-[4-(1-cyanocyclopropan-1-yl)-3-fluorophenyl]aminomethyloxazolidin-2-one, 5(S)-5-[N-(t-Butoxycarbonyl)-N-(1,2-isoxadiazolyl-3-yl)]-3-[4-(1-cyanocyclopropan-1-yl)-3-fluorophenyl]aminomethyloxazolidin-2-one, 5(S)-3-[4-(1-Cyanocyclopropan-1-yl)-3-fluorophenyl]-5-[N-(1,2,4-oxadiazolyl-3-yl)amino]methyloxazolidin-2-one, 5(S)-3-[4-(1-Cyanocyclopropan-1-yl)-3,5-difluorophenyl]-5-[N-(1,2,4-oxadiazolyl-3-yl)amino]methyloxazolidin-2-one, 5(S)-3-[4-(1-Cyanocyclopropan-1-yl)-3-fluorophenyl]-5-[N-(1,2,3,4-thiatriazolyl-5-yl)amino]methyloxazolidin-2-one, 5(S)-3-[4-(1-Cyanocyclopropan-1-yl)-3,5-difluorophenyl]-5-[N-(1,2,3,4-thiatriazolyl-5-yl)amino]methyloxazolidin-2-one, 5(S)-3-[4-(1-Cyanocyclopropan-1-yl)phenyl]-5-[N-(1,2,3,4-thiatriazolyl-5-yl)amino]methyloxazolidin-2-one, 5(S)-3-[4-(1-Cyanocyclopropan-1-yl)-3-fluorophenyl]-5-[N-(1,2-isoxadiazolyl-3-yl)amino]methyloxazolidin-2-one, (S)-3-[4-(1-Cyanocyclopropan-1-yl)-3,5-difluorophenyl]-5-[N-(1,2-isoxadiazolyl-3-yl)amino]methyloxazolidin-2-one, N-[5(S)-3-[4-(1-Cyanocyclopropan-1-yl)phenyl]-2-oxooxazolidin-5-ylmethyl]acetamide, N-[5(S)-3-[4-(1-Cyanocyclopropan-1-yl)phenyl]-2-oxooxazolidin-5-ylmethyl]thioacetamide, 5(S)-5-[N-(t-Butoxycarbonyl)-N-(1,2,4-oxadiazolyl-3-yl)]-3-[4-(1-cyanocyclopropan-1-yl)phenyl]aminomethyloxazolidin-2-one, 5(S)-5-[N-(t-Butoxycarbonyl)-N-(1,2-isoxadiazolyl-3-yl)]-3-[4-(1-cyanocyclopropan-1-yl)phenyl]aminomethyloxazolidin-2-one, 5(S)-3-[4-(1-Cyanocyclopropan-1-yl)phenyl]-5-[N-(1,2,4-oxadiazolyl-3-yl)amino]methyloxazolidin-2-one, 5(S)-3-[4-(1-Cyanocyclopropan-1-yl)phenyl]-5-[N-(1,2-isoxadiazolyl-3-yl)amino]methyloxazolidin-2-one, 5(R)-3-[4-(1-Cyanocyclopropan-1-yl)phenyl]-5-[N-(1,2-isoxadiazolyl-3-yl)oxy]methyloxazolidin-2-one, 5(S)-5-[N-(t-Butoxycarbonyl)-N-(1,3-thiazolyl-2-yl)]-3-[4-(1-cyanocyclopropan-1-yl)phenyl]aminomethyloxazolidin-2-one, 5(S)-5-[N-(t-Butoxycarbonyl)-N-(1,3,4-thiadiazolyl-2-yl)]-3-[4-(1-cyanocyclopropan-1-yl)phenyl]aminomethyloxazolidin-2-one, 5(S)-3-[4-(1-Cyanocyclopropan-1-yl)phenyl]-5-[N-(1,3-thiazolyl-2-yl)amino]methyloxazolidin-2-one, 5(S)-3-[4-(1-Cyanocyclopropan-1-yl)-3-fluorophenyl]-5-[N-(1,3-thiazolyl-2-yl)amino]methyloxazolidin-2-one, 5(S)-3-[4-(1-Cyanocyclopropan-1-yl)-3,5-difluorophenyl]-5-[N-(1,3-thiazolyl-2-yl)amino]methyloxazolidin-2-one, 5(S)-3-[4-(1-Cyanocyclopropan-1-yl)phenyl]-5-[N-(1,3,4-thiadiazolyl-2-yl)amino]methyloxazolidin-2-one, S-Methyl N-[5(S)-3-[4-(1-Cyanocyclopropan-1-yl)-3-fluorophenyl]-2-oxooxazolidin-5-ylmethyl]dithiocarbamate, S-Methyl N-[5(S)-3-[4-(1-Cyanocyclopropan-1-yl)-3,5-difluorophenyl]-2-oxooxazolidin-5-ylmethyl]dithiocarbamate, S-Methyl N-[5(S)-3-[4-(1-Cyanocyclopropan-1-yl)phenyl]-2-oxooxazolidin-5-ylmethyl]dithiocarbamate, N-[5(S)-3-[4-(1-Cyanocyclopropan-1-yl)-3-fluorophenyl]-2-oxooxazolidin-5-ylmethyl]thiourea, N-[5(S)-3-[4-(1-Cyanocyclopropan-1-yl)-3,5-fluorophenyl]-2-oxooxazolidin-5-ylmethyl]thiourea, N-[5(S)-3-[4-(1-Cyanocyclopropan-1-yl)phenyl]-2-oxooxazolidin-5-ylmethyl]thiourea, O-Methyl N-[5(S)-3-[4-(1-Cyanocyclopropan-1-yl)-3-fluorophenyl]-2-oxooxazolidin-5-ylmethyl]thiocarbonate, O-Methyl N-[5(S)-3-[4-(1-Cyanocyclopropan-1-yl)-3,5-difluorophenyl]-2-oxooxazolidin-5-ylmethyl]thiocarbonate, N'-Methyl N-[5(S)-3-[4-(1-Cyanocyclopropan-1-yl)-3-fluorophenyl]-2-oxooxazolidin-5-ylmethyl]thiourea, N'-Methyl N-[5(S)-3-[4-(1-Cyanocyclopropan-1-yl)-3,5-difluorophenyl]-2-oxooxazolidin-5-ylmethyl]thiourea, N'-Methyl N-[5(S)-3-[4-(1-Cyanocyclopropan-1-yl)phenyl]-2-oxooxazolidin-5-ylmethyl]thiourea, O-Methyl N-[5(S)-3-[4-(1-Cyanocyclopropan-1-yl)phenyl]-2-oxooxazolidin-5-ylmethyl]thiocarbonate, N'-Cyano N-[5(S)-3-[4-(1-Cyanocyclopropan-1-yl)phenyl]-2-oxooxazolidin-5-ylmethyl]acetamidine, and N'-Cyano N-[5(S)-3-[4-(1-Cyanocyclopropan-1-yl)-3-fluorophenyl]-2-oxooxazolidin-5-ylmethyl]acetamidine, or their enantiomer, diastereomer, or pharmaceutically acceptable salt, hydrate or prodrug thereof wherein.

The compounds of the present invention can be prepared according to the procedures of the following schemes and general examples, using appropriate materials, and are further exemplified by the following specific examples. The compounds illustrated in the examples are not, however, to be construed as forming the only genus that is considered as the invention. The following examples further illustrate details for the preparation of compounds of the present invention. Those skilled in the art will readily understand that known variations of the conditions and processes of the following preparative procedures can be used to prepare the compounds of the present invention. All temperatures are in degrees Celsius unless otherwise noted.

Scheme I

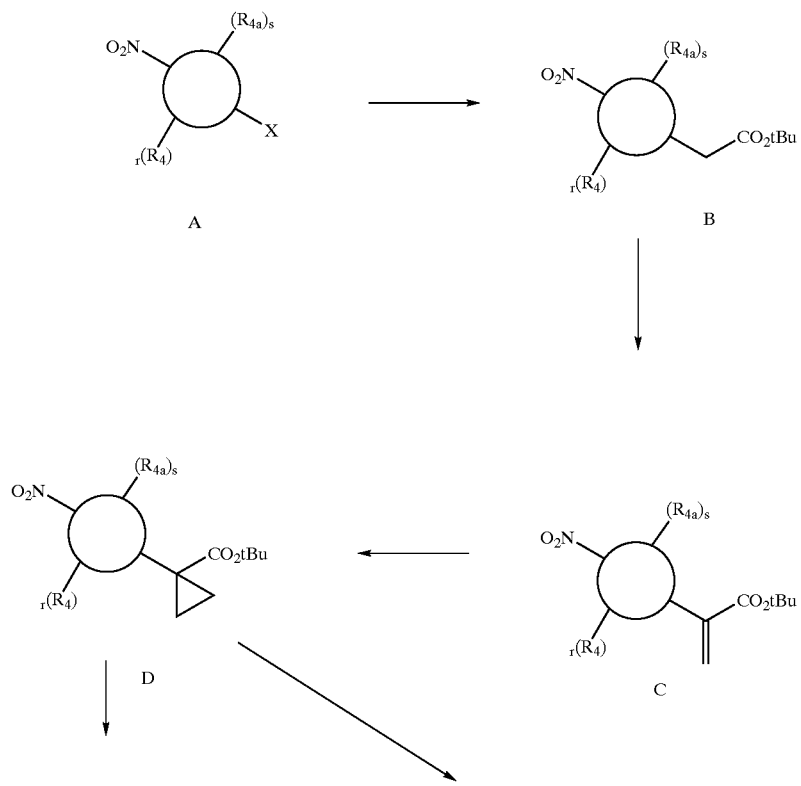

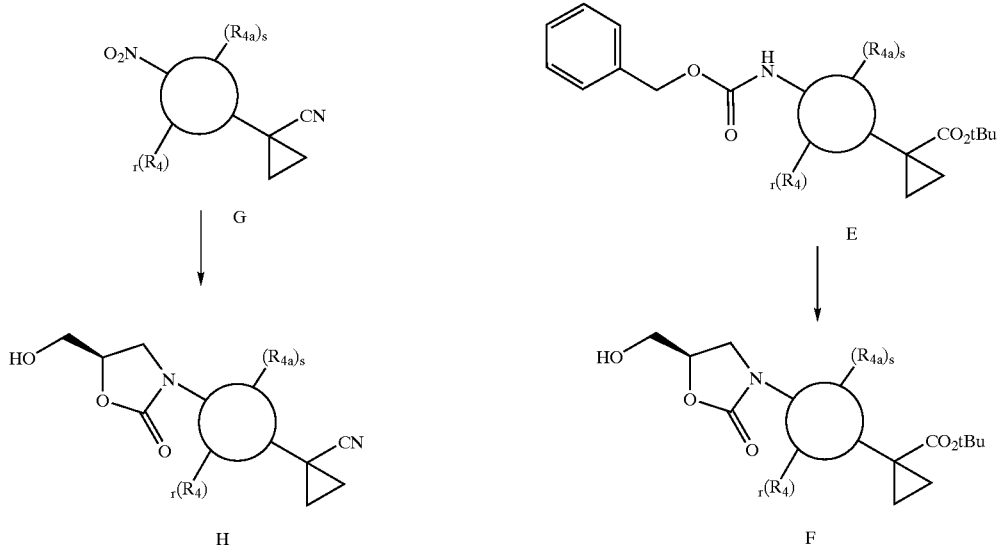

General Schemes for the preparation of the compounds of the present invention are detailed in Schemes I–IV. It should be recognized that the chemical transformations depicted in Schemes I–IV are performed in one possible sequence. It will be recognized by those skilled in the art that modifications of the described schemes can be mentioned in which the requisite transformations can be performed in a different sequence to obtain the compounds of the present invention. Thus, the general sequence of synthetic transformations described below should not be construed as limiting with regard to the preparation of the compounds of the present invention. As shown in Schemes I–II one general procedure for the preparation of the Compounds of the present invention begins from readily available nitroaromatic or nitroheteroaromatic compounds, A, which are optimally substituted with a leaving group (X) appropriate for substitution. In many cases a preferred leaving group is picked from one of the halogens, but those skilled in the art will recognize that in some cases other leaving groups may be substituted such as sulfonyl or phosphoryl ethers. Treatment of the selected compounds with a malonyl ester in the presence of an appropriate base readily selected by practitioners of the art followed by in situ hydrolysis of the resulting diester and decarboxylation under acidic conditions affords the resulting nitro substituted aromatic or heteroaromatic acetic acid. Typical malonyl esters would include ethyl or other lower alkyl esters as well as aryl esters such as phenyl or substituted phenyl esters. Many strong bases can be used for performing this transformation, some preferred bases include metal hydrides such as sodium hydride or potassium hydride along with non-nucleophilic amide bases such as lithium diisopropylamide or the like or alkoxide bases such as sodium ethoxide or sodium methoxide. Likewise a variety of aqueous acids sulfuric acid or hydrochloric acid can be envisioned for the hydrolysis and if necessary appropriate cosolvents such as acetic acid or propionic acid may be employed in the in situ decarboxylation of the intermediate diester to the desired aromatic or heteroaromatic acetic acid. Optionally the hydrolysis mixture may be heated to accelerate the rate of the reaction and often it is convenient to reflux the reaction mixture until the reaction has been completed. In a second step the aromatic or heteroaromatic acetic acid obtained above is esterified to form B. It will be recognized that there are a plethora of potential methods for the preparation of esters from acids and potentially many of them could be used for the preparation of the desired aromatic or heteroaromatic phenylacetic acid ester. While a number of alkyl esters could be formed in the above transformation the use of the t-butyl ester or other tertiary alkyl ester is preferred for the subsequent transformations. These esters may be prepared by a variety of methods such as reacting the aromatic or heteroaromatic phenyl acetic acid in a non-polar solvent with a 1,1-disubstituted olefin in the presence of a strong acid such as sulfuric acid. Alternatively the requisite tertiary alkyl ester B can be formed by in situ formation of an acid chloride or a mixed anhydride and allowing the resulting activated acid to react with a tertiary alcohol such as t-butanol or t-amyl alcohol to form the requisite tertiary ester. Preferred reagents for the activation of the aromatic or heteroaromatic acid include, but are not limited to, oxalyl chloride, thionyl chloride, or di-t-butyldicarbonate.

In the next step the ester B is converted to the acrylate C. A convenient method for the preparation of C is the reaction of B with Bis-N,N-dimethylaminomethane or another appropriate formaldehyde equivalent in an a nonprotic polar solvent such as dimethylsulfoxide or dimethylformamide or the like in the presence of an anhydride such as acetic anhydride. In this way the acrylate C is conveniently prepared and can be converted to the desired 1,1-substituted cyclopropane, D, by reaction with an ylide precursor such as trimethylsulfoxonium iodide in the presence of a non-nucleophilic base such as potassium t-butoxide of sufficient strength to form the requisite ylide.

The nitro cyclopropane D is then reduced to the amino compound and acylated to the carboxybenzyl-protected intermediate E. Numerous methods for the reduction of aromatic and heteroaromatic nitro compound to the corresponding amines will be well known to those familiar with the art and these are incorporated within the scope of the present invention. Particularly useful however is the reduction of the nitro group with hydrogen gas in the presence of a metal catalyst such as platinum, palladium, or ruthenium deposited on an inert carrier such as carbon in an appropriate solvent such as methanol, ethanol, acetic acid, ethyl acetate and the like. Alternatively other reducing agents such as SnCl$_2$ or FeCl$_3$ could be employed in the present reduction. The amine so synthesized is then acylated with an alkylchloroformate such as benzylchloroformate in a non-polar solvent such as tetrahydrofuran, ethyl ether, or methylene chloride to afford the required carboxybenzylprotected amine, E. The oxazolidinones of the present invention are then readily prepared in a stepwise fashion by first deprotonating E in an ethereal solvent such as tetrahydrofuran or diethyl ether with a strong base such as an alkyl lithium, alkyl magnesium halide or a dialkyl lithium amide. Examples of bases appropriate for this transformation would include but are not limited to n-butyl lithium, methyl magnesium bromide, t-butyl lithium, sec-butyl lithium, or lithium diisopropyl amide and the like. Typically the deprotonation is carried out at a reduced temperature in the range of 0° C. to −100° C. but may be performed at any appropriate temperature. Addition of a glycydyl ester such as glycidyl butyrate followed by warming to room temperature affords the desired 5-hydroxyoxazolidinone, F, of the present invention. It should be noted that if an R-glycydyl ester is used an R-5-hydroxyoxazolidinone will be obtained while if an S-glycydyl ester is employed an S-5-hydroxyoxazloidinone will be obtained. By this way oxazolidinones that are substantially single enantiomers can be prepared. However if racemic F would be desired, it would be readily prepared from an appropriate racemic glycydyl ester.

Optionally, if a 1-cyanosubstituted cyclopropane is desired in the compounds of the present invention the ester D may be converted to the cyano compound G. It will be recognized that there are several methods and reagents for carrying out this transformation. For example the ester may be hydrolyzed to the acid and subsequently reduced to the carbinol. Oxidation to the aldehyde followed by formation of the oxime and dehydration would then afford the cyano compound G. Alternatively the ester may be directly reduced to the carbinol and then converted to G as described above. In another modification of the invention one could directly convert the ester to the aldehyde and thence to G. All of the above methods are incorporated into the present invention. However, a particularly preferred procedure for performing this transformation involves removal of the ester under acidic conditions, such as treatment with trifluoroacetic acid, hydrochloric acid or another appropriate strong acid, conversion of the resulting acid to a mixed anhydride in situ by treatment with a reagent such ethylchloroformate and an amine base such as triethylamine and reduction of the resulting mixed anhydride with a hydride reducing agent such as sodium borohydride, lithium borohydride, lithium aluminum hydride, diisobutylaluminum hydride, or one of many other appropriate hydride reducing agents well known to practitioners of the art. The resulting carbinol is then oxidized to the aldehyde with reagents suitable for this transformation such as the Dess-Martin reagent or 1-hydroxy-1-benziodoxol-3(1H)-one, dimethylsulfoxide/oxalyl chloride, chromium trioxide pyridine complex, or another reagent chosen from oxidizing agents appropriate for this transformation. The resulting aldehyde is then converted to the oxime using hydroxylamine hydrochloride and an appropriate buffer such as sodium acetate and dehydrated with an appropriate dehydrating agent such as acetic anhydride or diisopropylazodicarboxylate in the presence of triphenyl phosphine to afford the requisite cyano compound, G. In a manner similar to that described above for the transformation of D to F, intermediate G can be converted to the 5-hydroxyoxazolidinone of the present invention H.

Scheme II

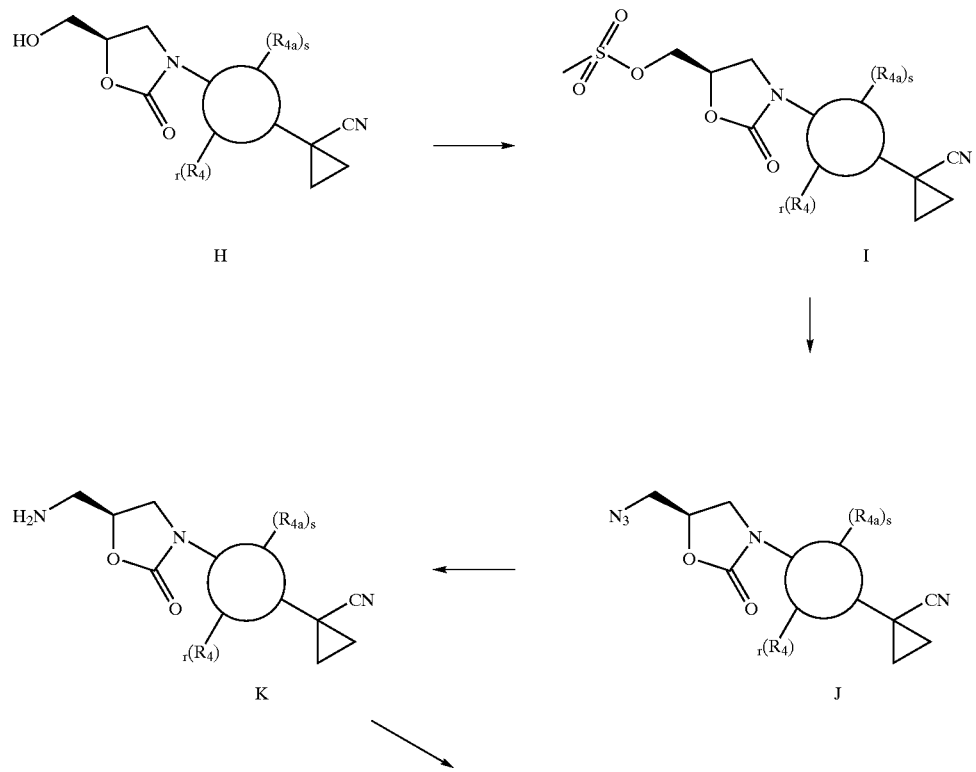

-continued

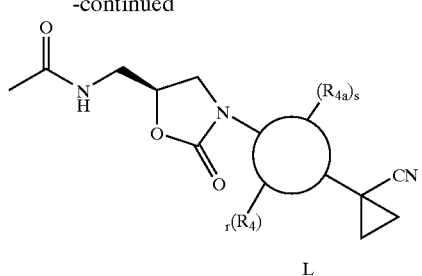

L

The 5-hydroxyoxazolidinones F and H are useful intermediates for the preparation of compounds of the present invention. In Scheme II further modifications of H are illustrated but it will be realized that similar modifications of F can be performed to form analogous compounds of the present invention and that further modification of both F and H are incorporated within the present invention. The hydroxymethyloxazolidinone H can be converted to a leaving group by treatment with an appropriate reagent. Preferred leaving groups include the mesylate, tosylate, benzenesulfonate, trifluoromethanesulfonate, halides and the like and the methods to produce these intermediates will be readily recognized by those skilled in the art. A preferred leaving group is the mesylate I which may be readily prepared by treatment with methanesulfonylchloride in a nonpolar solvent such as methylene chloride, tetrahydrofuran, diethylether, carbon tetrachloride, dichloroethane and the like using a tertiary amine such as triethylamine as a catalyst. The resulting mesylate I can be further converted to compounds of the present invention by treatment with a variety of nucleophiles which substitute the mesylate radical with the nucleophile radical of the present invention. Examples of nucleophiles that can be used include, but are not limited to sodium azide, sodiumthiocyanate, heterocycles such as 1,2,3-triazole, imidazole, pyrazole and the like optionally activated as their metal salts by the addition of sodium hydride or other such appropriate base. Typical solvents for these reactions include such solvents as dimethylformamide or dimethylsulfoxide which are particularly useful for displacements of this type but may also include less polar solvents such as methylene chloride, tetrahydrofuran, diethyl ether, or alcohol solvents such as methanol, ethanol , or isopropyl alcohol when appropriate. A particularly useful intermediate is the 5-azidomethyl oxazolidinone J. The azide J can be used as a substrate in 1,3-dipolar additions in which a substituent is added to the proximal and distal nitrogens of the azide to afford 1,2,3-triazole analogues. For example treatment of J with norbornadiene at reflux in dioxane affords the 1-substituted, 1,2,3-triazole while treatment with malononitrile affords the 4-cyano-5-amino-1,2,3-triazole. Similarly the 5-hydroxymethyl-1,2,3-triazole can be prepared from J and propargyl alcohol which can itself be transformed to a variety of analogues of the present invention by modifications of the hydroxymethyl group to the aldehyde, oxime, oximemethyl ether, and cyano analogues and the like by methods which will be readily apparent to those of ordinary skill in the art. Treatment of J in a similar manner with t-butyl propiolate affords the t-butyl 1-substituted-1,2,3-triazole-4-carboxylate and the ester can be further transformed to the acid and modified to further amide and ester analogues of the present invention. Alternatively reduction of the ester to the hydroxymethyl analogue would allow further modification as described above for the 5-hydroxymethyl regioisomer.

In addition to being a substrate for 1,3-dipolar additions, the 5-azidomethyl oxazolidinone J can be reduced to the 5-aminomethyl oxazolidinone K. The 5-aminomethyl oxazolidinone can be acylated with a wide variety of acylating agents under appropriate conditions. Examples of acylating agents used to prepare compounds of the present invention include, but are not limited to acetic anhydride, difluoroacetic anhydride, trifluoroacetic anhydride, bis-2 (1H)-hydroxypyridine thiocarbonate, methylisothiocyanate, O-methyl-N-cyanoacetamide, propionic anhydride, methylchloroformate, dichloroacetylchloride, N-cyanodithioiminocarbonate, and sulfonyl chlorides such as methane sulfonyl chloride and the like. Alternatively carboxylic acids can be used to acylated the 5-aminomethyloxazolidinone, K. In these modifications the carboxylic acids are typically activated for acylation by conversion to the acid chloride with thionyl chloride or oxalyl chloride or activated in situ with a carbodiimde such as dicyclohexyl carbodiimide. Examples of carboxylic acids that can be used to acylate K include but are not limited to cyclopropanecarboxylic acid, 2-methoxyacetic acid, furn-3-carboxylic acid, pyrazine-2-carboxylic acid, isoxazole-5-carboxylic acid, 1,2,5-thiadiazole-3-carboxylic acid, 4-methylthiazole-5-carboxylic acid, formic acid, methylthioacetic acid, methylsulfonylacetic acid, 2,2,-dichlorocyclopropane-1-carboxylic acid, 2-chloropropionic acid, 1-cyano-cyclopropane-1-carboxylic acid, 1-hydroxycyclopropane-1-carboxylic acid.

One preferred modification of the 5-aminomethyl-oxazolidinone K is the 5-acetamidomethyl oxazolidinone L which is readily prepared from K by treatment with acetic anhydride. The acetamide L can be further modified to the thioacetamide by treatment with Lawesson's reagent, or alkylated with alkyl halides such as methyl iodide in the presence of a suitable base such as potassium t-butoxide to afford the N-alkylacetamides.

Further compounds of the present invention can be prepared by displacement of the hydroxyl group of the 5-hydroxymethyloxazolidinone H with an appropriate nucleophile. Typically displacements of this sort are carried out under conditions known to those skilled in the art as Mitsunobu conditions. These generally involve in situ activation of H with an azodicarboxylate analogue such as diethylazodicarboxylate, diisopropylazodicarboxylate, or tetramethylazodicarboxamide, in the presence of a phosphine such as tributyl phosphine, triphenyl phosphine or trifuryl phosphine in a suitable solvent such as benzene, ether, toluene, tetrahydrofuran, or methylene chloride. Among the nucleophiles used in such displacement reactions to prepare compounds of the present invention include but are not limited to N-benzoyloxyacetamide heterocycles such as 1,2,4-triazole, pyrazole, 1H-tetrazole, 3-hydroxyisoxazole, and t-butoxycarbonylprotected amino-heterocycles such as 3-N-(t-butoxycarbonyl)amino-1,2,4-oxadiazole, 3-N-(t-butoxycarbonyl)amino-1,2-isoxazole, 2-N-(t-butoxycarbonyl)amino-1,3-thiazole, and 2-N-(t-butoxycarbonyl)amino-1,3,4-thiadiazole, and 2-N-(t-butoxycarbonyl)aminopyridine. In those cases where an amino group is protected as a t-butoxycarbonyl derivative or where an hydroxy is protected by a benzoyl group, these protecting groups can be removed under conditions well known to those skilled in the art to prepare the corresponding amino or hydroxyl analogues of the present invention.

As mentioned above and as shown in Scheme III the 5-hydroxymethyl oxazolidinone F can converted to the mesylate M which can in turn be converted to the 5-azidomethyloxazolidinone N. The 5-azidomethyloxazolidinone N can be reduced to the 5-aminomethyloxazolidinone O which can in turn be acylated to the 5-acetamidooxazolidinone P. These conversions can be carried out in a manner exactly analogous to the conversion of H to L as described in Scheme II. Moreover further modifications of F, M, N, O, and P can be carried out. For example analogous modifications to that described for H can be carried out on F to afford further compounds of the present invention. Likewise, M can be modified analogous to I, N modified analogous J, O modified analogous to K, and P modified analogous to L. All of these analogous modifications are incorporated into the compounds of the present invention. In addition the t-butoxycarbonyl group of F, M, N, O, and P can be independently modified to form further compounds of the present invention. These modifications are exemplified in Scheme IV for compound P, but it will be readily recognized by those with ordinary skill in the art that analogous modifications could be made to F, M, N, or O independently and all of the potential modifications are incorporated into the compounds of the present invention.

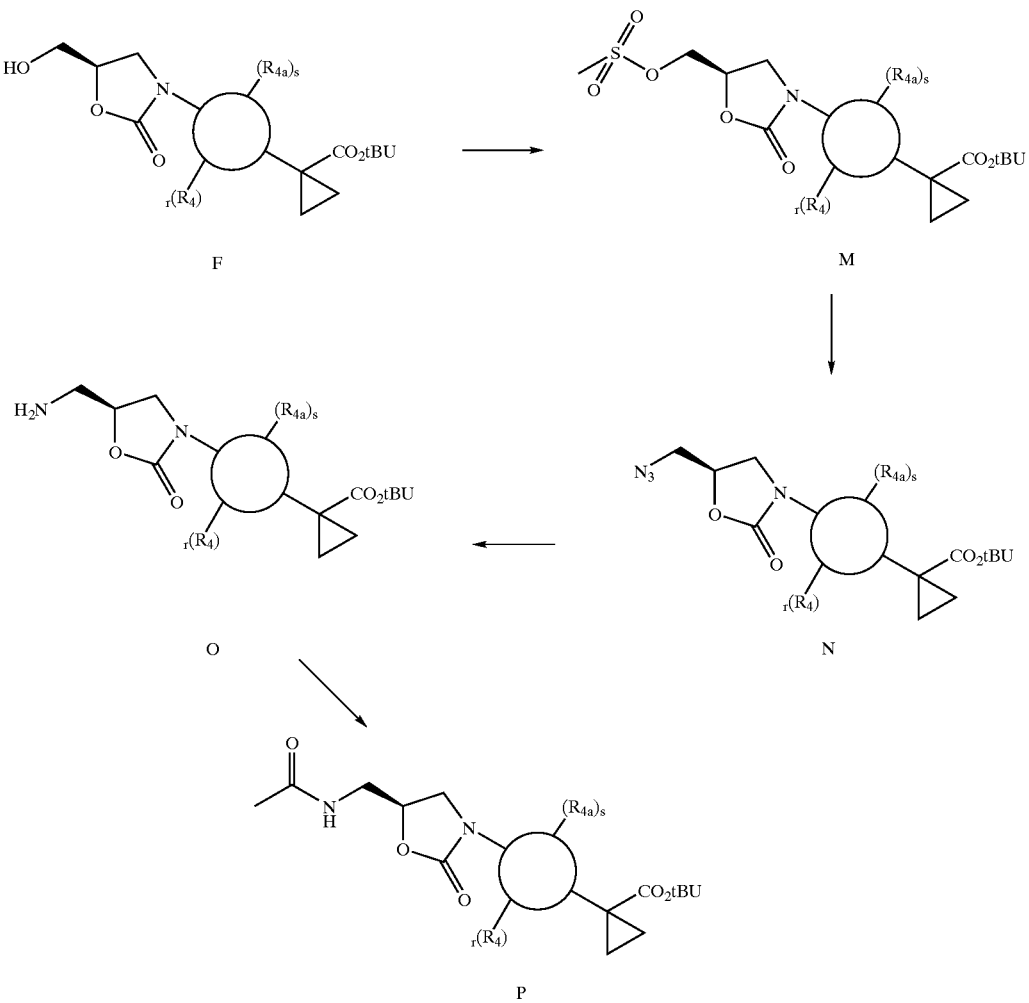

Scheme III

As shown in Scheme IV compound P can be treated with a strong acid such as tnrifuoroacetic acid or hydrochloric acid in a nonpolar solvent such as methylene chloride to afford the carboxylic acid Q. It will be recognized by those with ordinary skill in the art that a variety of methods are known for the conversion of Q to the amine R. In a preferred method Q is treated with triphenylphosphoryl azide in a nonpolar solvent such as methylene chloride in the presence of a tertiary amine base to afford R. Alternatively Q can be reduced to the hydroxymethyl compound S by formation of the mixed anhydride with alkylchloroformate such as ethylchloroformate in the presence of a tertiary amine base and the in situ formed anhydride reduced with aqueous sodium borohydride which after workup in the standard way affords S. As described above a variety of methods are available for the oxidation of primary alcohol to the aldehyde, thus in a preferred, but not limiting transformation S is treated with 1-hydroxy-1,2-benziodoxol-3(1H)-one 1-oxide to afford the aldehyde T. The compound T can be converted to the oxime U by treatment with hydroxylamine hydrochloride in an alcoholic solvent such as methanol in the presence of a mild base such as sodium acetate. It should be recognized that dehydration of T by methods described above for the dehydration of oximes provides an alternative method for the preparation of L.

of in vivo activity when the compositions are administered to a mammal infected with a susceptible bacterial organism.

Using standard susceptibility tests, the compositions of the invention are determined to be active against MRSA and enterococcal infections.

The compounds of the invention are formulated in pharmaceutical compositions by combining the compounds with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating Scheme IV

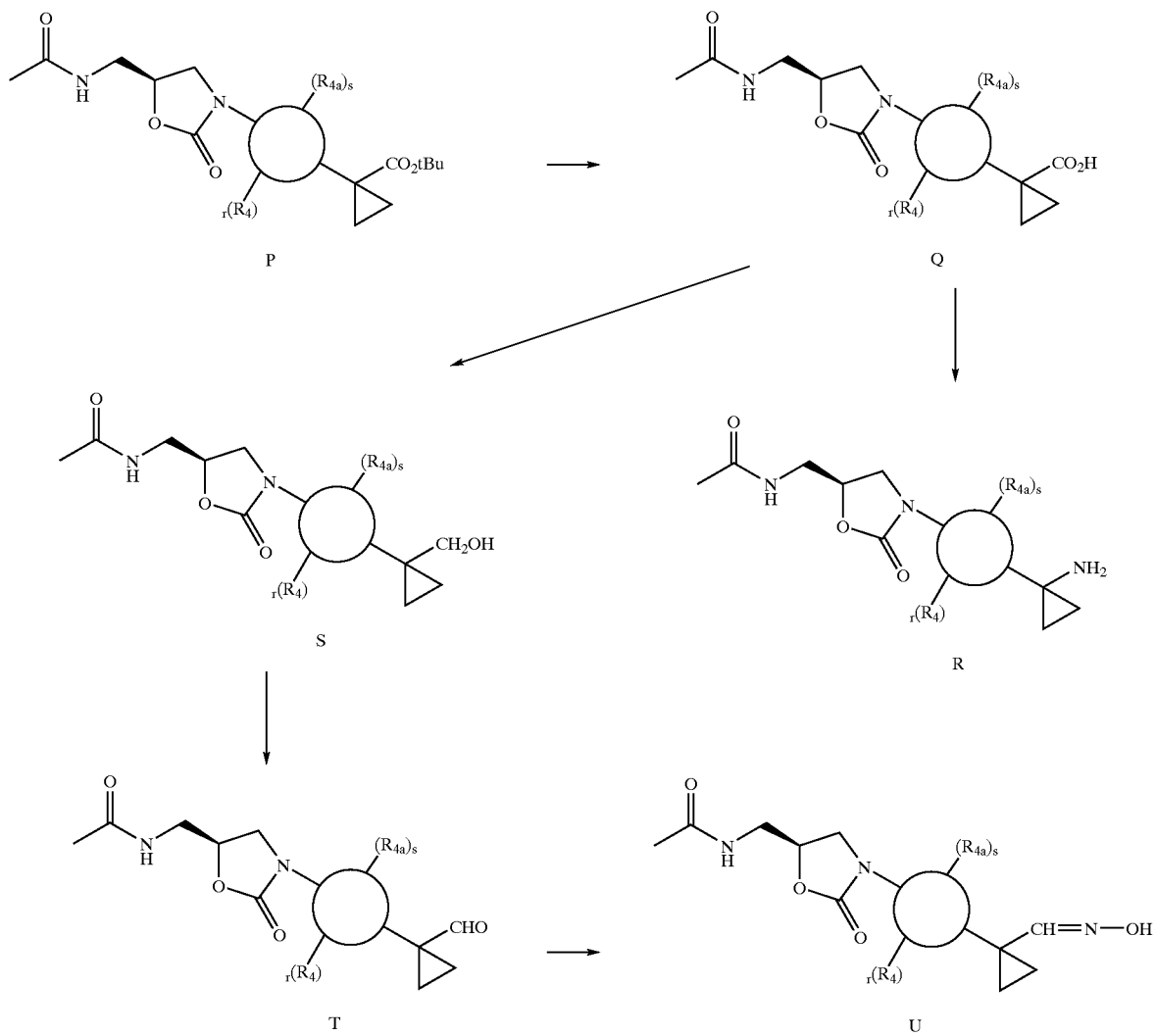

Suitable subjects for the administration of the formulation of the present invention include mammals, primates, man, and other animals. In vitro antibacterial activity is predictive agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The novel antibiotic compositions of this invention for human delivery per unit dosage, whether liquid or solid, comprise from about 0.01% to as high as about 99% of the cyclopropyl containing oxazolidinone compounds discussed herein, the preferred range being from about 10–60% and from about 1% to about 99.99% of one or more of other antibiotics such as those discussed herein, preferably from about 40% to about 90%. The composition will generally contain from about 125 mg to about 3.0 g of the cyclopropyl containing oxazolidinone compounds discussed herein; however, in general, it is preferable to employ dosage amounts in the range of from about 250 mg to 1000 mg and from about 200 mg to about 5 g of the other antibiotics discussed herein; preferably from about 250 mg to about 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal the claimed composition in an amount effective to treat said infection.

The preferred methods of administration of the claimed compositions include oral and parenteral, e.g., i.v. infusion, i.v. bolus and i.m. injection formulated so that a unit dosage comprises a therapeutically effective amount of each active component or some submultiple thereof.

For adults, about 5–50 mg/kg of body weight, preferably about 250 mg to about 1000 mg per person of the cyclopropyl containing oxazolidinone antibacterial compound and about 250 mg, to about 1000 mg per person of the other antibiotic(s) given one to four times daily is preferred. More specifically, for mild infections a dose of about 250 mg two or three times daily of the cyclopropyl containing oxazolidinone antibacterial compound and about 250 mg two or three times daily of the other antibiotic is recommended. For moderate infections against highly susceptible gram positive organisms a dose of about 500 mg each of the cyclopropyl containing oxazolidinone and the other antibiotics, three or four times daily is recommended. For severe, life-threatening infections against organisms at the upper limits of sensitivity to the antibiotic, a dose of about 500–2000 mg each of the cyclopropyl-containing oxazolidinone compound and the other antibiotics, three to four times daily may be recommended.

For children, a dose of about 5–25 mg/kg of body weight given 2, 3, or 4 times per day is preferred; a dose of 10 mg/kg is typically recommended.

The invention is further described in connection with the following non-limiting examples.

Antibacterial Activity

The pharmaceutically-acceptable compounds of the present invention are useful antibacterial agents having a good spectrum of activity in vitro against standard bacterial strains, which are used to screen for activity against pathogenic bacteria. Notably, the pharmaceutically-acceptable compounds of the present invention show activity against vancomycin-resistant enterococci, streptococci including penicillin-resistant *S. pneumoniae*, methicillin-resistant *S. aureus*, *M. catarrhalis*, and *C. pneumoniae*. The antibacterial spectrum and potency of a particular compound may be determined in a standard test system.

The following in vitro results were obtained based on an agar dilution method except for *C. pneumoniae*. The activity is presented as the minimum inhibitory concentration (MIC) *S. aureus* and *M. catarrhalis* were tested on Mueller-Hinton agar, using an approximate inoculum of $1 \times 10^4$ cfu/spot an incubation temperature of 35C for 24 hours. The MIC was defined as the lowest concentration at which no visible bacterial growth was observed.

Streptococci and enterococci were tested on Mueller-Hinton agar supplemented with 5% defibrinated horse blood, using an approximate inoculum of $1 \times 10^4$ cfu/spot an incubation temperature of 35C in an atmosphere of 5% $CO_2$ for 24 hours. The MIC was defined as the lowest concentration at which no visible bacterial growth was observed.

*C. pneumoniae* was tested using minimum essential medium supplemented with 10% heat-inactivated fetal bovine serum, 2 mM L-glutamine, 1 mg/ml cycloheximide and non essential amino acid. HeLa 229 cells were inoculated with $10^4$ inclusion-forming units of *C. pneumoniae* strain per mL. Infected cells were incubated with test compounds in complete medium at 35C in an atmosphere of 5% $CO_2$ for 72 hours. Cells monolayers were fixed in methanol, stained for chlamydial inclusions with an fluorescein-conjugated anti-Chiamydia monoclonal antibody, and were observed with fluorescence microscope. The MIC was defined as the lowest concentration at which no inclusion was observed.

| Strains | example 7 | example 8 | example 18 | example 32 | Linezolid |
|---|---|---|---|---|---|
| *Staphylococcus aureus* | | | | | |
| Smith | 0.5 | 0.125 | 0.5 | 0.125 | 1 |
| CR | 4 | 0.5 | 16 | 2 | 16 |
| MR | 0.5 | 0.125 | 0.5 | 0.125 | 1 |
| *Streptococcus pneumoniae* | | | | | |
| IID553 | 1 | 0.25 | 1 | 0.25 | 2 |
| PRQR | 1 | 0.25 | 1 | 0.125 | 1 |
| *Streptococcus pyogenes* | | | | | |
| IID692 | 0.5 | 0.125 | 1 | 0.125 | 1 |
| *Enterococcus faecium* | | | | | |
| VRQR | 0.5 | 0.25 | 1 | 0.25 | 2 |
| *Moraxella catarrhalis* | | | | | |
| ATCC25238 | 4 | 0.5 | 8 | 0.5 | 4 |
| *Chlamydia pneumoniae* | | | | | |
| ATCCVR-1360 | 0.5 | 0.25 | NT | 4 | 8 |

CR = chloramphenicol resistant
MR = methicillin resistant
PRQR = penicillin resistant, quinolone resistant
VRQR = vancomycin resistant, quinolone resistant
NT = not tested The invention described herein is exemplified by the following non-limiting examples. The compound data is designated in accordance with *General Guidelines for Manuscript Preparation*, J. Org. Chem. Vol. 66, pg. 19A, Issue January, 2001.

The invention described herein is exemplified by the following non-limiting examples. The compound data is designated in accordance with *General Guidelines for Manuscript Preparation*, J. Org. Chem. Vol. 66, pg. 19A, Issue January, 2001.

EXAMPLE 1

N-[5(S)-3-[4-[(1-t-Butoxycarbonyl)cyclopropan-1-yl]-3-fluorophenyl]-2-oxooxazolidin-5-ylmethyl]acetamide

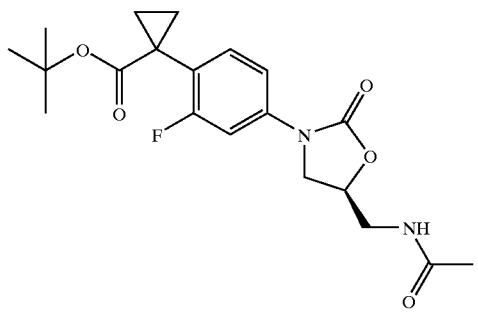

Step 1

5(R)-3-[4-[(1-t-Butoxycarbonyl)cyclopropan-1-yl]-3-fluorophenyl]-5-hydroxymethyloxazolidin-2-one.

To a solution of t-butyl 1-(4-benzyloxycarbonylamino-2-fluorophenyl)cyclopropane-1-carboxylate (7.30 g) in dry tetrahydrofuran (100 mL) was added a solution of n-butyllithium in hexane (1.6 M, 11.9 mL) at −78° C., and the mixture was stirred at the same temperature for 30 min. (R)-Glycidyl butyrate (2.16 g) was added to the mixture at −78° C. and the mixture was allowed to stand at room temperature for 12 hours. After quenching the reaction with the addition of saturated ammonium chloride solution, the mixture was extracted with ethyl acetate. The organic extracts were washed with brine, dried over anhydrous magnesium sulfate, filtered, and then concentrated in vacuo. A suspension of the residue and potassium carbonate (3 g) in methanol (50 mL) was stirred at room temperature for 10 min. After dilution the mixture with water, the mixture was extracted with ethyl acetate. The organic extracts were washed with brine, dried over anhydrous magnesium sulfate, filtered, and then concentrated in vacuo. Flash chromatography (silica, hexane:ethyl acetate=1:4) of the residue gave 5(R)-3-[4-[(1-t-butoxycarbonyl)-cyclopropan-1-yl]-3-fluorophenyl]-5-hydroxymethyloxazolidin-2-one.

MS (EI$^+$) m/z: 351 (M$^+$). HRMS (EI$^+$) for $C_{18}H_{22}FNO_5$ (M$^+$): calcd, 351.1482; found, 351.1469.

Step 2

5(R)-Azidomethyl-3-[4-[(1-t-butoxycarbonyl)cyclopropan-1-yl]-3-fluorophenyl]-oxazolidin-2-one.

To a solution of 5(R)-3-[4-[(1-t-butoxycarbonyl)cyclopropan-1-yl]-3-fluorophenyl]-5-hydroxymethyloxazolidin-2-one (2.00 g) in dichloromethane (15 mL) was successively added triethylamine (1.59 mL) and methanesulfonyl chloride (1.23 g) at 0° C., and the mixture was stirred at the same temperature for 30 min. The mixture was washed with saturated sodium hydrogencarbonate solution and brine, dried over anhydrous magnesium sulfate, filtered, and then concentrated in vacuo to give 5(R)-3-[4-[(1-t-butoxycarbonyl)cyclopropan-1-yl]-3-fluorophenyl]-5-methanesulfonyloxymethyloxazolidin-2-one. This was used in the next step without further purification. The mixture of crude 5(R)-3-[4-[(1-t-butoxycarbonyl)-cyclopropan-1-yl]-3-fluorophenyl]-5-methanesulfonyloxymethyloxazolidin-2-one thus obtained and sodium azide (1.30 g) in N,N-dimethylformamide (15 mL) was heated at 60° C. for 9 hours, and then concentrated in vacuo. The residue was diluted with ethyl acetate and washed with water and brine. The organic extracts were dried over anhydrous magnesium sulfate, filtered, and then concentrated in vacuo to give 5(R)-azidomethyl-3-[4-[(1-t-butoxycarbonyl)cyclopropan-1-yl]-3-fluorophenyl]-oxazolidin-2-one. MS (EI$^+$) m/z: 376 (M$^+$).

HRMS (EI$^+$) for $C_{18}H_{21}FN_4O_4$ (M$^+$): calcd, 376.1547; found, 376.1524.

Step 3

N-[5(S)-3-[4-[(1-t-Butoxycarbonyl)cyclopropan-1-yl]-3-fluorophenyl]-2-oxooxazolidin-5-ylmethyl]acetamide.

A suspension of crude 5(R)-azidomethyl-3-[4-[(1-t-butoxycarbonyl)cyclopropan-1-yl]-3-fluorophenyl]oxazolidin-2-one thus obtained in step 2 and palladium catalyst (10% on charcoal, 214 mg) in ethyl acetate (57 mL) was hydrogenated at 1 atmosphere for 3 hours at room temperature. After filtration of the catalyst, the filtrate was concentrated in vacuo to give 5(S)-aminomethyl-3-[4-[(1-t-butoxycarbonyl)cyclopropan-1-yl]-3-fluorophenyl]oxazolidin-2-one. To a solution of crude 5(S)-aminomethyl-3-[4-[(1-t-butoxycarbonyl)cyclopropan-1-yl]-3-fluorophenyl]oxazolidin-2-one thus obtained in ethyl acetate (50 mL) was added triethylamine (4.8 mL) and acetic anhydride (1.6 mL), and the mixture was stirred at room temperature for 2 hours. After quenching the reaction by the addition of saturated sodium hydrogencarbonate solution, the mixture was extracted with ethyl acetate. The organic extracts were washed with brine, dried over anhydrous magnesium sulfate, filtered, and then concentrated in vacuo. Flash chromatography (silica, ethyl acetate:methanol=20:1) of the residue gave N-[5(S)-3-[4-[1-t-butoxycarbonyl)cyclopropan-1-yl]-3-fluorophenyl]-2-oxooxazolidin-5-ylmethyl]acetamide. MS (EI$^+$) m/z: 392 (M$^+$).

HRMS (EI$^+$) for $C_{20}H_{25}FN_2O_5$ (M$^+$): calcd, 392.1748; found, 392.1730.

EXAMPLE 2

N-[5(S)-3-[4-(1-Carboxycyclopropan-1-yl)-3-fluorophenyl]-2-oxooxazolidin-5-ylmethyl]acetamide

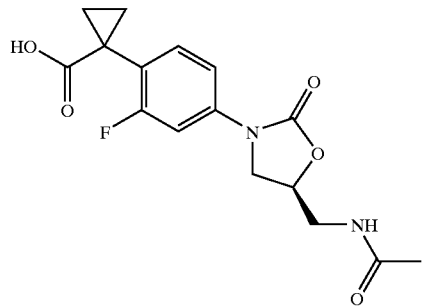

To a solution of N-[5(S)-3-[4-[(1-t-butoxycarbonyl)cyclopropan-1-yl]-3-fluorophenyl]-2-oxooxazolidin-5-ylmethyl]acetamide (0.73 g) in dichloromethane (10 mL) was added trifluoroacetic acid (5 mL) at 0° C., and the mixture was stirred at room temperature for 1 hour, then concentrated in vacuo to give N-[5(S)-3-[4-(1-carboxycyclopropan-1-yl)-3-fluorophenyl]-2-oxooxazolidin-5-ylmethyl]acetamide.

MS (EI$^+$) m/z: 336 (M$^+$). HRMS (EI$^+$) for $C_{16}H_{17}FN_2O_5$ (M$^+$): calcd, 336.1122; found, 336.1140.

EXAMPLE 3

N-[5(S)-3-[3-Fluoro-4-(1-hydroxymethylcyclopropan-1-yl)phenyl]-2-oxooxazolidin-5-ylmethyl]acetamide

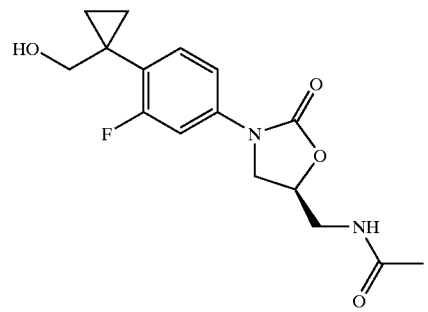

To a solution of N-[5(S)-3-[4-(1-carboxycyclopropan-1-yl)-3-fluorophenyl]-2-oxooxazolidin-5-ylmethyl]acetamide (500 mg) in tetrahydrofuran (10 mL) was successively added triethylamine (249 L) and ethyl chloroformate (156 L) at 0° C., and the mixture was stirred at the same temperature for 30 min. To a suspension of sodium borohydride (562 mg) in water (5 mL) was added the above mixture at 0° C., and the mixture was stirred at room temperature for 30 min. The mixture was adjusted to pH 2 by the addition of 1 N hydrochloric acid, and extracted with dichloromethane. The organic extracts were washed with brine, dried over anhydrous magnesium sulfate, filtered, and then concentrated in vacuo. Flash chromatography (silica, ethyl acetate:methanol=9:1) of the residue gave N-[5(S)-3-[3-fluoro-4-(1-hydroxymethylcyclopropan-1-yl)phenyl]-2-oxooxazolidin-5-ylmethyl]acetamide. MS (EI$^+$) m/z: 322 (M$^+$).

HRMS (EI) for $C_{16}H_{19}FN_2O_4$ (M): calcd, 322.1329; found, 322.1319.

EXAMPLE 4

N-[5(S)-3-[4-(1-Aminocyclopropan-1-yl)-3-fluorophenyl]-2-oxooxazolidin-5-ylmethyl]acetamide

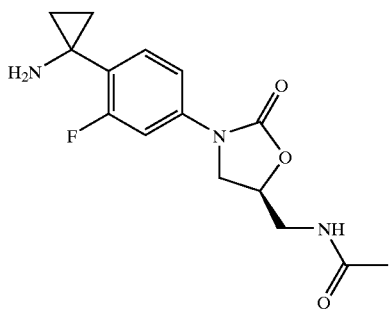

To a solution of N-[5(S)-3-[4-(1-carboxycyclopropan-1-yl)-3-fluorophenyl]-2-oxooxazolidin-5-ylmethyl]acetamide (prepared from of N-[5(S)-3-[4-[(1-t-butoxycarbonyl)cyclopropan-1-yl]-3-fluorophenyl]-2-oxooxazolidin-5-ylmethyl]acetamide (420 mg) in the same manner as described for EXAMPLE 2) in dichloromethane (5 mL) was added triethylamine (224 L) and DPPA (442 mg) at room temperature, and the mixture was stirred at the same temperature for 30 min, then concentrated in vacuo. The resulting residue was diluted with toluene, the mixture was heated at reflux for 2 hours, and then concentrated in vacuo. To a solution of the residue in dioxane (10 mL) was added 10% potassium carbonate solution (10 mL), and the mixture was stirred at room temperature for 1 hour. After dilution the mixture with brine, the mixture was extracted with ethyl acetate. The ethyl acetate solution was extracted with 5% hydrochloric acid. The aqueous extracts were adjusted to pH 10 by the addition of potassium carbonate, diluted with brine, and extracted with ethyl acetate and dichloromethane-methanol (4:1). The combined organic extracts were dried over anhydrous magnesium sulfate, filtered, and then concentrated in vacuo. Flash chromatography (silica, dichloromethane:methanol=9:1) of the residue gave N-[5 (S)-3-[4-(1-aminocyclopropan-1-yl)-3-fluorophenyl]-2-oxooxazolidin-5-ylmethyl]acetamide.

MS (EI$^+$) m/z: 307 (M$^+$). HRMS (EI$^+$) for $C_{15}H_{18}FN_3O_3$ (M$^+$): calcd, 307.1332; found, 307.1329.

EXAMPLE 5

N-[5(S)-3-[3-Fluoro-4-(1-formylcyclopropan-1-yl) phenyl]-2-oxooxazolidin-5-ylmethyl]acetamide

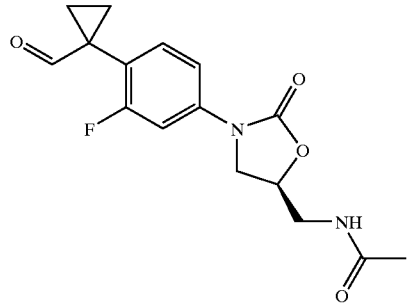

To a solution of N-[5(S)-3-[3-fluoro-4-(1-hydroxymethylcyclopropan-1-yl)phenyl]-2-oxooxazolidin-5-ylmethyl]acetamide (337 mg) in dimethyl sulfoxide (5 mL) was added 1-hydroxy-1,2-benziodoxol-3(1H)-one 1-oxide (439 mg), and the mixture was stirred at room temperature for 12 hours. After dilution with saturated sodium hydrogencarbonate solution, the mixture was extracted with ethyl acetate. The organic extracts were washed with brine, dried over anhydrous magnesium sulfate, filtered, and then concentrated in vacuo. Flash chromatography (silica, ethyl acetate:methanol=10:1) of the residue gave N-[5(S)-3-[3-fluoro-4-(1-formylcyclopropan-1-yl) phenyl]-2-oxooxazolidin-5-ylmethyl]acetamide.

MS (EI$^+$) m/z: 320 (M$^+$). HRMS (EI$^+$) for $C_{16}H_{17}FN_2O_4$ (M$^+$): calcd, 320.1172; found, 320.1190.

EXAMPLE 6

N-[5(S)-3-[3-Fluoro-4-(1-(hydroxyimino) methylcyclopropan-1-yl)phenyl]-2-oxooxazolidin-5-ylmethyl]acetamide

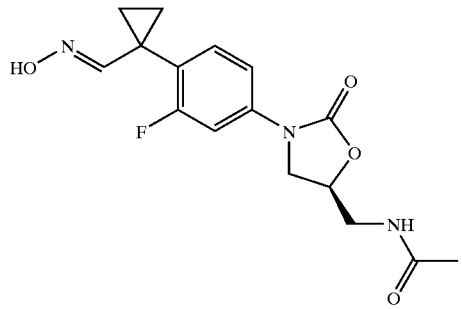

To a solution of hydroxylamine hydrochloride (163 mg) in methanol (10 mL) was added sodium acetate (384 mg), and the mixture was stirred at room temperature for 30 min. To a resulting mixture was added N-[5(S)-3-[3-fluoro-4-(1-formylcyclopropan-1-yl)phenyl]-2-oxooxazolidin-5-ylmethyl]acetamide (250 mg), the mixture was stirred at room temperature for 30 min, and then concentrated in vacuo. Flash chromatography (silica, dichloromethane:methanol=9:1) of the residue gave N-[5 (S)-3-[3-fluoro-4-(1-(hydroxyimino)methylcyclopropan-1-yl)phenyl]-2-oxooxazolidin-5-ylmethyl]acetamide.

MS (EI$^+$) m/z: 335 (M$^+$). HRMS (EI$^+$) for $C_{16}H_{18}FN_3O_4$ (M$^+$): calcd, 335.1281; found, 335.1233.

EXAMPLE 7

N-[5(S)-3-[4-(1-Cyanocyclopropan-1-yl)-3-fluorophenyl]-2-oxooxazolidin-5-ylmethyl] acetamide

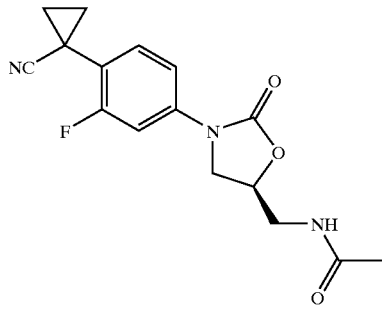

To a solution of N-[5(S)-3-[3-fluoro-4-(1-(hydroxyimino) methylcyclopropan-1-yl)phenyl]-2-oxooxazolidin-5-ylmethyl]acetamide (160 mg) in tetrahydrofuran (5 mL) was added diisopropyl azodicarboxylate (145 mg) and triphenylphosphine (375 mg) at room temperature, and the mixture was stirred at the same temperature for 10 min. Flash chromatography (silica, ethyl acetate:methanol=19:1) of the mixture gave N-[5(S)-3-[4-(1-cyanocyclopropan-1-yl)-3-fluorophenyl]-2-oxooxazolidin-5-ylmethyl]acetamide.

MS (EI$^+$) m/z: 317 (M$^+$).

HRMS (EI$^+$) for $C_{16}H_{16}FN_3O_3$ (M$^+$): calcd, 317.1176; found, 317.1177.

EXAMPLE 8

N-[5(S)-3-[4-(1-Cyanocyclopropan-1-yl)-3-fluorophenyl]-2-oxooxazolidin-5-ylmethyl]thioacetamide

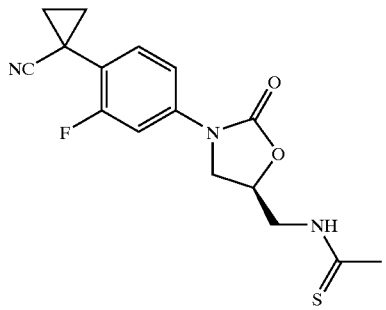

To a solution of N-[5(S)-3-[4-(1-cyanocyclopropan-1-yl)-3-fluorophenyl]-2-oxooxazolidin-5-ylmethyl]acetamide (120 mg) in toluene was added Lawesson's reagent (153 mg) at 80° C., and the mixture was stirred at the same temperature for 2 hours. Flash chromatography (silica, hexane:ethyl acetate=1:1) of the mixture gave N-[5(S)-3-[4-(1-cyanocyclopropan-1-yl)-3-fluorophenyl]-2-oxooxazolidin-5-ylmethyl]thioacetamide. MS (FAB$^+$) m/z: 334 (MH$^+$).

HRMS (FAB$^+$) for $C_{16}H_{17}FN_3O_2S$ (MH$^+$): calcd, 334.1026; found, 334.1043.

EXAMPLE 9

N-[5(S)-3-[4-(1-Cyanocyclopropan-1-yl)-3-fluorophenyl]-2-oxooxazolidin-5-ylmethyl]methanesulfonylamide

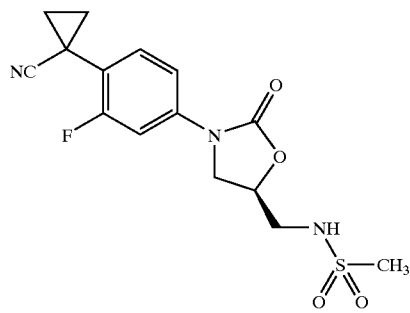

A suspension of 5(R)-azidomethyl-3-[4-(1-cyanocyclopropan-1-yl)-3-fluorophenyl]oxazolidin-2-one (122 mg) and Lindlar catalyst (12 mg) in methanol (5 mL) was hydrogenated at 1 atm for 3 hours at room temperature. After filtration of the catalyst, the filtrate was concentrated in vacuo to give 5(S)-aminomethyl-3-[4-(1-cyanocyclopropan-1-yl)-3-fluorophenyl]oxazolidin-2-one. To a solution of crude 5(S)-aminomethyl-3-[4-(1-cyanocyclopropan-1-yl)-3-fluorophenyl]oxazolidin-2-one thus obtained in dichloromethane (2 mL) was added pyridine (96 mg) and methanesulfonyl chloride (70 mg) at 0° C., and the mixture was stirred at the same temperature for 30 min. The mixture was washed with water and 5% hydrochloric acid, dried over anhydrous magnesium sulfate, filtered, and then concentrated in vacuo. Flash chromatography (silica, ethyl acetate) of the residue gave N-[5(S)-3-[4-(1-cyanocyclopropan-1-yl)-3-fluorophenyl]-2-oxooxazolidin-5-ylmethyl]methanesulfonylamide. MS (EI$^+$) m/z: 353 (M$^+$).

HRMS (EI$^+$) for $C_{15}H_{16}FN_3O_4S$ (M$^+$): calcd, 353.0846; found, 353.0869.

EXAMPLE 10

N-[5(S)-3-[4-[(1-t-Butoxycarbonyl)cyclopropan-1-yl]-3,5-difluorophenyl]-2-oxooxazolidin-5-ylmethyl]acetamide

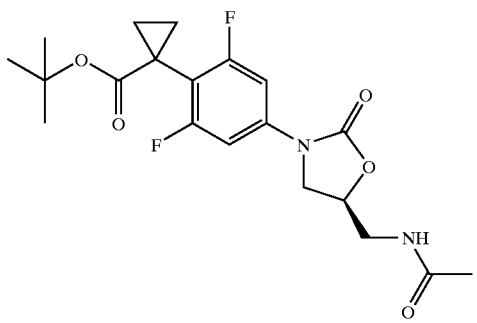

Step 1

5(R)-Azidomethyl-3-[4-[(1-t-butoxycarbonyl)cyclopropan-1-yl]-3-fluorophenyl]oxazolidin-2-one.

The title compound 5(R)-azidomethyl-3-[4-[(1-t-butoxycarbonyl)cyclopropan-1-yl]-3,5-difluorophenyl]oxazolidin-2-one (19.5 g) was prepared from t-butyl 1-(4-benzyloxycarbonylamino-2,6-difluorophenyl)-cyclopropane-1-carboxylate (13.6 g) in the same manner as described for EXAMPLE 1.

Step 2

N-[5(S)-3-[4-[(1-t-Butoxycarbonyl)cyclopropan-1-yl]-3,5-difluorophenyl]-2-oxooxazolidin-5-ylmethyl]acetamide.

The title compound N-[5(S)-3-[4-[(1-t-butoxycarbonyl)cyclopropan-1-yl]-3,5-difluorophenyl]-2-oxooxazolidin-5-ylmethyl]acetamide (5.90 g) was prepared from 5(R)-azidomethyl-3-[4-[(1-t-butoxycarbonyl)cyclopropan-1-yl]-3,5-difluorophenyl]oxazolidin-2-one (7.57 g) in the same manner as described for EXAMPLE 1.

MS (EI$^+$) m/z: 410 (M$^+$). HRMS (EI$^+$) for $C_{20}H_{24}F_2N_2O_5$ (M$^+$): calcd, 410.1653; found, 410.1693.

EXAMPLE 11

N-[5(S)-3-[3,5-Difluoro-4-(1-hydroxymethylcyclopropan-1-yl)phenyl]-2-oxooxazolidin-5-ylmethyl]acetamide

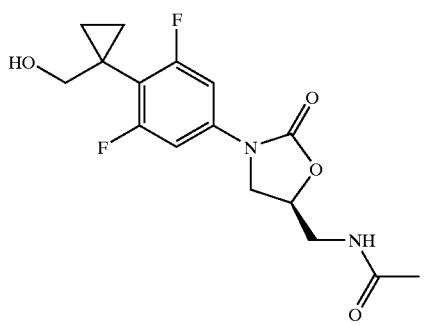

Step 1

N-[5(S)-3-[4-(1-Carboxycyclopropan-1-yl)-3,5-difluorophenyl]-2-oxooxazolidin-5-ylmethyl]acetamide.

The title compound N-[5(S)-3-[4-(1-carboxycyclopropan-1-yl)-3,5-difluorophenyl]-2-oxooxazolidin-5-ylmethyl]acetamide was prepared from N-[5(S)-3-[4-[(1-t-butoxycarbonyl)cyclopropan-1-yl]-3,5-difluorophenyl]-2-oxooxazolidin-5-ylmethyl]acetamide (3.00 g) in the same manner as described for EXAMPLE 2.

MS (EI$^+$) m/z: 354 (M$^+$). HRMS (EI$^+$) for $C_{16}H_{16}F_2N_2O_5$ (M$^+$): calcd, 354.1027; to found, 354.0984.

Step 2

N-[5(S)-3-[3,5-Difluoro-4-(1-hydroxymethylcyclopropan-1-yl)phenyl]-2-oxooxazolidin-5-ylmethyl]acetamide.

The title compound N-[5(S)-3-[3,5-difluoro-4-(1-hydroxymethylcyclopropan-1-yl)phenyl]-2-oxooxazolidin-5-ylmethyl]acetamide (2.11 g) was prepared from crude N-[5(S)-3-[4-(1-carboxycyclopropan-1-yl)-3,5-difluorophenyl]-2-oxooxazolidin-5-ylmethyl]acetamide thus obtained in step 1 in the same manner as described for EXAMPLE 3.

MS (EI$^+$) m/z: 340 (M$^+$). HRMS (EI$^+$) for $C_{16}H_{18}F_2N_2O_4$ (M$^+$): calcd, 340.1235; found, 340.1211.

EXAMPLE 12

N-[5(S)-3-[3,5-Difluoro-4-(1-formylcyclopropan-1-yl)phenyl]-2-oxooxazolidin-5-ylmethyl]acetamide

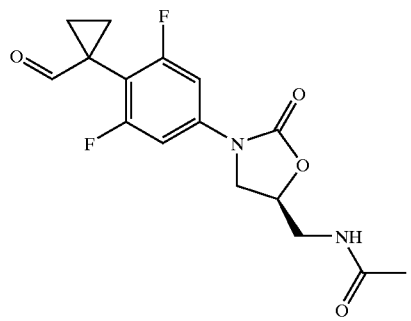

The title compound N-[5(S)-3-[3,5-difluoro-4-(1-formylcyclopropan-1-yl)phenyl]-2-oxooxazolidin-5-ylmethyl]acetamide (520 mg) was prepared from N-[5(S)-3-[3,5-difluoro-4-(1-hydroxymethylcyclopropan-1-yl)phenyl]-2-oxooxazolidin-5-ylmethyl]acetamide (1.00 g) in the same manner as described for EXAMPLE 5.

MS (EI$^+$) m/z: 338 (M$^+$). HRMS (EI$^+$) for $C_{16}H_{16}F_2N_2O_4$ (M$^+$): calcd, 338.1078; found, 338.1099.

EXAMPLE 13

N-[5(S)-3-[4-(1-Cyanocyclopropan-1-yl)-3,5-difluorophenyl]-2-oxooxazolidin-5-ylmethyl]acetamide

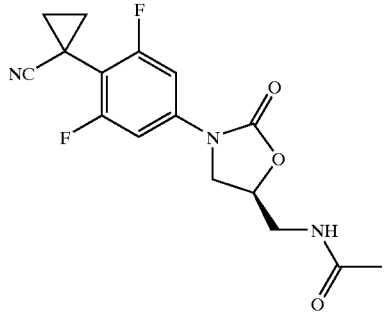

The title compound N-[5(S)-3-[4-(1-cyanocyclopropan-1-yl)-3,5-difluorophenyl]-2-oxooxazolidin-5-ylmethyl]acetamide (418 mg) was prepared from N-[5(S)-3-[3,5-difluoro-4-(1-formylcyclopropan-1-yl)phenyl]-2-oxooxazolidin-5-ylmethyl]acetamide (520 mg) in the same manner as described for EXAMPLE 6 and 7. MS (EI$^+$) m/z: 335 (M$^+$).

HRMS (EI$^+$) for $C_{16}H_{15}F_2N_3O_3$ (M$^+$): calcd, 335.1081; found, 335.1080.

EXAMPLE 14

N-[5(S)-3-[4-(1-Cyanocyclopropan-1-yl)-3-fluorophenyl]-2-oxooxazolidin-5-ylmethyl]difluoroacetamide

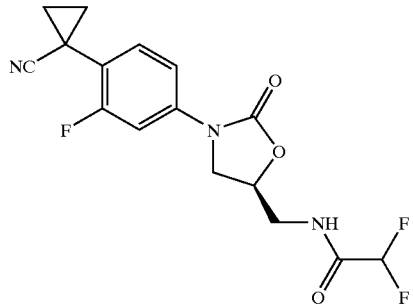

Step 1

5(R)-3-[4-(1-Cyanocyclopropan-1-yl)-3-fluorophenyl]-5-hydroxymethyloxazolidin-2-one.

The title compound 5(R)-3-[4-(1-cyanocyclopropan-1-yl)-3-fluorophenyl]-5-hydroxymethyloxazolidin-2-one (483 mg) was prepared from 1-(4-benzyloxycarbonylamino-2-fluorophenyl)-1-cyclopropanecarbonitrile (638 mg) in the same manner as described for EXAMPLE 1. MS (EI$^+$) m/z: 276 (M$^+$).

HRMS (EI$^+$) for $C_{14}H_{13}FN_2O_3$ (M$^+$): calcd, 276.0910; found, 276.0905.

Step 2

5(R)-Azidomethyl-3-[4-(1-cyanocyclopropan-1-yl)-3-fluorophenyl]oxazolidin-2-one.

The title compound 5(R)-azidomethyl-3-[4-(1-cyanocyclopropan-1-yl)-3-fluorophenyl]oxazolidin-2-one (490 mg) was prepared from 5(R)-3-[4-(1-cyanocyclopropan-1-yl)-3-fluorophenyl]-5-hydroxymethyloxazolidin-2-one (450 mg) in the same manner as described for EXAMPLE 1. MS (EI$^+$) m/z: 301 (M$^+$).

HRMS (EI$^+$) for C$_{14}$H$_{12}$FN$_5$O$_2$ (M$^+$): calcd, 301.0975; found, 301.0964.

Step 3

N-[5(S)-3-[4-(1-Cyanocyclopropan-1-yl)-3-fluorophenyl]-2-oxooxazolidin-5-ylmethyl]difluoroacetamide.

To a solution of crude 5(S)-aminomethyl-3-[4-(1-cyanocyclopropan-1-yl)-3-fluorophenyl]oxazolidin-2-one (prepared from 5(R)-azidomethyl-3-[4-(1-cyanocyclopropan-1-yl)-3-fluorophenyl]oxazolidin-2-one (490 mg) in the same manner as described for EXAMPLE 9) in pyridine (10 mL) was added difluoroacetic anhydride (340 mg) at 0° C., and the mixture was stirred at room temperature for 2 hours. After quenching the reaction by the addition of water, the mixture was extracted with ethyl acetate. The organic extracts were washed with brine, dried over anhydrous sodium sulfate, filtered, and then concentrated in vacuo. Flash chromatography (silica, hexane:ethyl acetate=1:1) of the residue gave N-[5(S)-3-[4-(1-cyanocyclopropan-1-yl)-3-fluorophenyl]-2-oxooxazolidin-5-ylmethyl]-difluoroacetamide. MS (EI$^+$) m/z: 353 (M$^+$).

HRMS (EI$^+$) for C$_{16}$H$_{14}$F$_3$N$_3$O$_3$ (M$^+$): calcd, 353.0987; found, 353.0983.

EXAMPLE 15

5(S)-5-[N-(t-Butoxycarbonyl)-N-(1,2,4-oxadiazolyl-3-yl)]-3-[4-(1-cyanocyclopropan-1-yl)-3-fluorophenyl]aminomethyloxazolidin-2-one

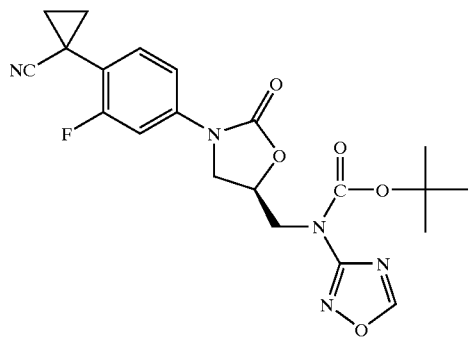

A mixture of 5(R)-3-[4-(1-cyanocyclopropan-1-yl)-3-fluorophenyl]-5-hydroxymethyloxazolidin-2-one (250 mg), 3-N-(t-butoxycarbonyl)amino-1,2,4-oxadiazole (252 mg), tetramethylazodicarboxamide (312 mg), and tributylphosphine (0.45 mL) in benzene (10 mL) was heated at 70–80° C. for 7.7 hours. After insoluble materials were filtered off, the filtrate was concentrated in vacuo. Flash chromatography (silica, hexane:ethyl acetate=1:1) of the residue gave 5(S)-5-[N-(t-butoxycarbonyl)-N-(1,2,4-oxadiazolyl-3-yl)]-3-[4-(1-cyanocyclopropan-1-yl)-3-fluorophenyl]aminomethyloxazolidin-2-one. MS (EI$^+$) m/z: 443 (M$^+$).

HRMS (EI$^+$) for C$_{21}$H$_{22}$FN$_5$O$_5$ (M$^+$): calcd, 443.1605; found, 443.1637.

EXAMPLE 16

5(S)-5-[N-(t-Butoxycarbonyl)-N-(1,2-isoxadiazolyl-3-yl)]-3-[4-(1-cyanocyclopropan-1-yl)-3-fluorophenyl]aminomethyloxazolidin-2-one

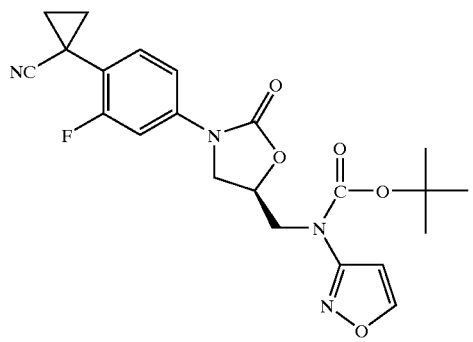

The title compound 5(S)-5-[N-(t-butoxycarbonyl)-N-(1,2-isoxadiazolyl-3-yl)]-3-[4-(1-cyanocyclopropan-1-yl)-3-fluorophenyl]amino-methyloxazolidin-2-one (364 mg) was prepared from 5(R)-3-[4-(1-cyanocyclopropan-1-yl)-3-fluorophenyl]-5-hydroxymethyloxazolidin-2-one (250 mg) and 3-N-(t-butoxycarbonyl)aminoisoxazole (250 mg) in the same manner as described for EXAMPLE 15. MS (EI$^+$) m/z: 442 (M$^+$).

HRMS (EI$^+$) for C$_{22}$H$_{23}$FN$_4$O$_5$ (M$^+$): calcd, 442.1652; found, 442.1650.

EXAMPLE 17

5(S)-3-[4-(1-Cyanocyclopropan-1-yl)-3-fluorophenyl]-5-[N-(1,2,4-oxadiazolyl-3-yl)amino]methyloxazolidin-2-one

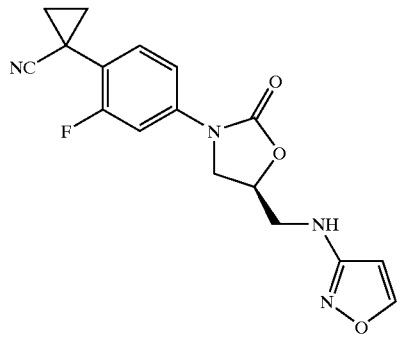

To a solution of 5(S)-5-[N-(t-butoxycarbonyl)-N-(1,2,4-oxadiazolyl-3-yl)]-3-[4-(1-cyanocyclopropan-1-yl)-3-fluorophenyl]aminomethyloxazolidin-2-one (331 mg) in dichloromethane (8 mL) was added trifluoroacetic acid at 0° C., and the mixture was stirred at the same temperature for 40 min. After quenching the reaction by the addition of saturated sodium hydrogencarbonate solution and 1 N sodium hydroxide solution, the mixture was extracted with dichloromethane. The organic extracts were washed with brine, dried over anhydrous sodium sulfate, filtered, and then concentrated in vacuo. After treating the residue with methanol, the resulting precipitates were collected by filtration to give 5(S)-3-[4-(1-cyanocyclopropan-1-yl)-3-fluorophenyl]-5-[N-(1,2,4-oxadiazolyl-3-yl)amino]methyloxazolidin-2-one. Flash chromatography (silica, hexane:ethyl acetate=1:4) of the filtrate gave further amount of the product. MS (EI⁺) m/z: 343 (M⁺).

HRMS (EI⁺) for $C_{16}H_{14}FN_5O_3$ (M⁺): calcd, 343.1081; found, 343.1067.

EXAMPLE 18

5(S)-3-[4-(1-Cyanocyclopropan-1-yl)-3-fluorophenyl]-5-[N-(1,2-isoxadiazolyl-3-yl)amino]methyloxazolidin-2-one

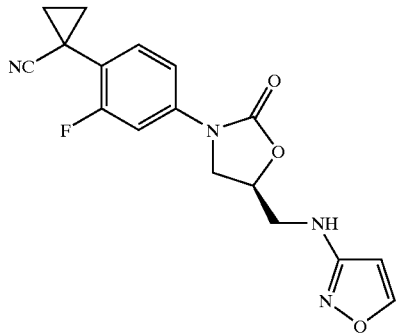

The title compound 5(S)-3-[4-(1-cyanocyclopropan-1-yl)-3-fluorophenyl]-5-[N-(1,2-isoxadiazolyl-3-yl)amino]methyloxazolidin-2-one (242 mg) was prepared from 5(S)-5-[N-(t-butoxycarbonyl)-N-(1,2-isoxadiazolyl-3-yl)]-3-[4-(1-cyanocyclopropan-1-yl)-3-fluorophenyl]aminomethyloxazolidin-2-one (360 mg) in the same manner as described for EXAMPLE 17. MS (EI⁺) m/z: 342 (M⁺).

HRMS (EI⁺) for $C_{17}H_{15}FN_4O_3$ (M⁺): calcd, 342.1128; found, 342.1141.

EXAMPLE 19

N-[5(S)-3-[4-(1-Cyanocyclopropan-1-yl)phenyl]-2-oxooxazolidin-5-ylmethyl]acetamide

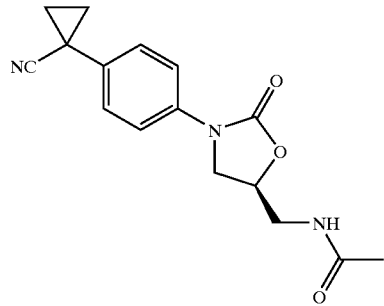

Step 1

5(R)-3-[4-(1-Cyanocyclopropan-1-yl)phenyl]-5-hydroxymethyloxazolidin-2-one.

The title compound 5(R)-3-[4-(1-cyanocyclopropan-1-yl)phenyl]-5-hydroxymethyloxazolidin-2-one (6.31 g) was prepared from 1-(4-benzyloxycarbonylaminophenyl)-1-cyclopropanecarbonitrile (8.34 g) in the same manner as described for EXAMPLE 1. MS (EI⁺) m/z: 258 (M⁺).

HRMS (EI⁺) for $C_{14}H_{14}N_2O_3$ (M⁺): calcd, 258.1004; found, 258.1021.

Step 2

5(R)-Azidomethyl-3-[4-(1-cyanocyclopropan-1-yl)phenyl]oxazolidin-2-one.

The title compound 5(R)-azidomethyl-3-[4-(1-cyanocyclopropan-1-yl)phenyl]oxazolidin-2-one (1.30 g) was prepared from 5(R)-3-[4-(1-cyanocyclopropan-1-yl)phenyl]-5-hydroxymethyloxazolidin-2-one (1.36 g) in the same manner as described for EXAMPLE 1. MS (EI⁺) m/z: 283 (M⁺).

HRMS (EI⁺) for $C_{14}H_{12}FN_5O_2$ (M⁺): calcd, 283.1069; found, 283.1059.

Step 3

N-[5(S)-3-[4-(1-Cyanocyclopropan-1-yl)phenyl]-2-oxooxazolidin-5-ylmethyl]acetamide.

The title compound N-[5(S)-3-[4-(1-cyanocyclopropan-1-yl)phenyl]-2-oxooxazolidin-5-ylmethyl]acetamide (388 mg) was prepared from 5(R)-azidomethyl-3-[4-(1-cyanocyclopropan-1-yl)phenyl]oxazolidin-2-one (634 mg) in the same manner as described for EXAMPLE 1. MS (EI⁺) m/z: 299 (M⁺).

HRMS (EI⁺) for $C_{16}H_{17}N_3O_3$ (M⁺): calcd, 299.1270; found, 299.1281.

EXAMPLE 20

N-[5(S)-3-[4-(1-Cyanocyclopropan-1-yl)phenyl]-2-oxooxazolidin-5-ylmethyl]thioacetamide

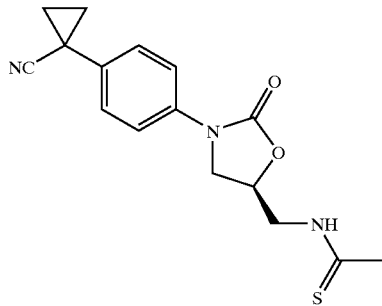

The title compound N-[5(S)-3-[4-(1-cyanocyclopropan-1-yl)phenyl]-2-oxooxazolidin-5-ylmethyl]thioacetamide (196 mg) was prepared from N-[5(S)-3-[4-(1-cyanocyclopropan-1-yl)phenyl]-2-oxooxazolidin-5-ylmethyl]acetamide (212 mg) in the same manner as described for EXAMPLE 8. MS (FAB⁺) m/z: 316 (MH⁺).

HRMS (FAB⁺) for $C_{16}H_{18}N_3O_2S$ (M⁺): calcd, 316.1120; found, 316.1116.

EXAMPLE 21

5(S)-5-[N-(t-Butoxycarbonyl)-N-(1,2,4-oxadiazolyl-3-yl)]-3-[4-(1-cyanocyclopropan-1-yl)phenyl]aminomethyloxazolidin-2-one

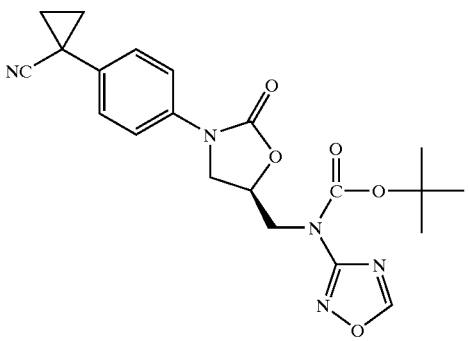

The title compound 5(S)-5-[N-(t-butoxycarbonyl)-N-(1,2,4-oxadiazolyl-3-yl)]-3-[4-(1-cyanocyclopropan-1-yl)

phenyl]aminomethyloxazolidin-2-one (113 mg) was prepared from 5(R)-3-[4-(1-cyanocyclopropan-1-yl)phenyl]-5-hydroxymethyloxazolidin-2-one (260 mg) and 3-t-butoxycarbonylamino-1,2,4-oxadiazole (278 mg) in the same manner as described for EXAMPLE 15.

MS (EI$^+$) m/z: 425 (M$^+$). HRMS (EI$^+$) for C$_{21}$H$_{23}$N$_5$O$_5$ (M$^+$): calcd, 425.1699; found, 425.1689.

EXAMPLE 22

5(S)-5-[N-(t-Butoxycarbonyl)-N-(1,2-isoxadiazolyl-3-yl)]-3-[4-(1-cyanocyclopropan-1-yl)phenyl]aminomethyloxazolidin-2-one

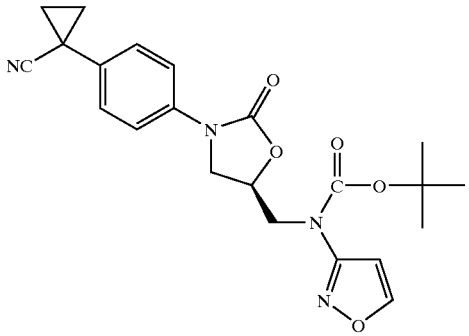

The title compound 5(S)-5-[N-(t-butoxycarbonyl)-N-(1,2-isoxadiazolyl-3-yl)]-3-[4-(1-cyanocyclopropan-1-yl)phenyl]aminomethyloxazolidin-2-one (1.53 g) was prepared from 5(R)-3-[4-(1-cyanocyclopropan-1-yl)phenyl]-5-hydroxymethyloxazolidin-2-one (1.00 g) and 3-t-butoxycarbonylamino-1,2-isoxazole (855 mg) in the same manner as described for EXAMPLE 15.

MS (EI$^+$) m/z: 424 (M$^+$). HRMS (EI$^+$) for C$_{22}$H$_{24}$N$_4$O$_5$ (M$^+$): calcd, 424.1747; found, 424.1765.

EXAMPLE 23

5(S)-3-[4-(1-Cyanocyclopropan-1-yl)phenyl]-5-[N-(1,2,4-oxadiazolyl-3-yl)amino]methyloxazolidin-2-one

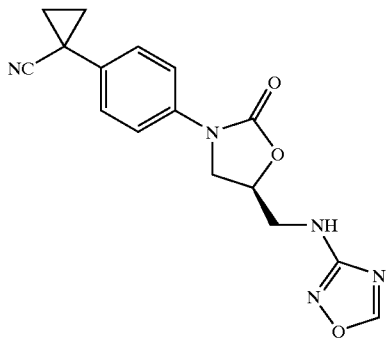

The title compound 5(S)-3-[4-(1-cyanocyclopropan-1-yl)phenyl]-5-[N-(1,2,4-oxadiazolyl-3-yl)amino]methyloxazolidin-2-one (55 mg) was prepared from 5(S)-5-[N-(t-butoxycarbonyl)-N-(1,2,4-oxadiazolyl-3-yl)]-3-[4-(1-cyanocyclopropan-1-yl)phenyl]aminomethyloxazolidin-2-one (113 mg) in the same manner as described for EXAMPLE 17. MS (FAB$^+$) m/z: 326 (MH$^+$).

HRMS (FAB$^+$) for C$_{16}$H$_{16}$N$_5$O$_3$ (MH$^+$): calcd, 326.1253; found, 326.1231.

EXAMPLE 24

5(S)-3-[4-(1-Cyanocyclopropan-1-yl)phenyl]-5-[N-(1,2-isoxadiazolyl-3-yl)amino]methyloxazolidin-2-one

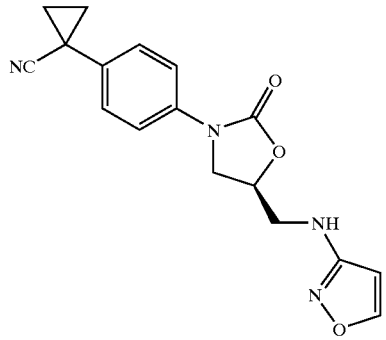

The title compound 5(S)-3-[4-(1-cyanocyclopropan-1-yl)phenyl]-5-[N-(1,2-isoxadiazolyl-3-yl)amino]methyloxazolidin-2-one (1.11 g) was prepared from 5(S)-5-[N-(t-butoxycarbonyl)-N-(1,2-isoxadiazolyl-3-yl)]-3-[4-(1-cyanocyclopropan-1-yl)phenyl]aminomethyloxazolidin-2-one (1.53 g) in the same manner as described for EXAMPLE 17. MS (FAB$^+$) m/z: 325 (MH$^+$).

HRMS (FAB$^+$) for C$_{17}$H$_{18}$N$_4$O$_3$ (MH$^+$): calcd, 325.1379; found, 325.1287.

EXAMPLE 25

5(R)-3-[4-(1-Cyanocyclopropan-1-yl)phenyl]-5-[N-(1,2-isoxadiazolyl-3-yl)oxy]methyloxazolidin-2-one

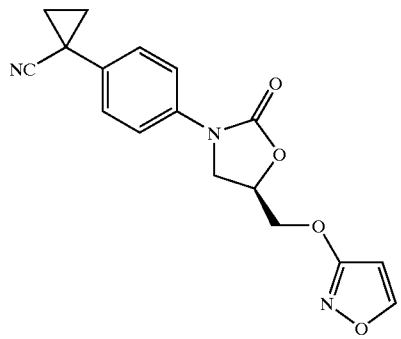

To a solution of 5(R)-3-[4-(1-cyanocyclopropan-1-yl)phenyl]-5-hydroxymethyloxazolidin-2-one (249 mg) in tetrahydrofuran (15 mL) was added 3-hydroxyisoxazole (106 mg), triphenylphosphine (380 mg), and diisopropyl azodicarboxylate (0.25 mL), the mixture was stirred at room temperature for 50 min, and then concentrated in vacuo. Flash chromatography (silica, hexane:ethyl acetate=1:1) of the residue gave 5(R)-3-[4-(1-cyanocyclopropan-1-yl)phenyl]-5-[N-(1,2-isoxadiazolyl-3-yl)oxy]methyloxazolidin-2-one. MS (EI$^+$) m/z: 325 (M$^+$).

HRMS (EI$^+$) for C$_{17}$H$_{15}$N$_3$O$_4$ (M$^+$): calcd, 325.1063; found, 325.1078.

EXAMPLE 26

5(S)-5-[N-(t-Butoxycarbonyl)-N-(1,3-thiazolyl-2-yl)]-3-[4-(1-cyanocyclopropan-1-yl)phenyl] aminomethyloxazolidin-2-one

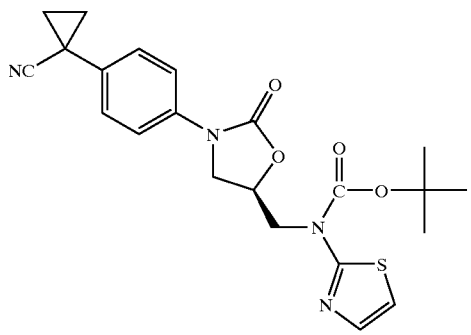

The title compound 5(S)-5-[N-(t-butoxycarbonyl)-N-(1,3-thiazolyl-2-yl)]-3-[4-(1-cyanocyclopropan-1-yl)phenyl] aminomethyloxazolidin-2-one (363 mg) was prepared from 5(R)-3-[4-(1-cyanocyclopropan-1-yl)phenyl]-5-hydroxymethyloxazolidin-2-one (250 mg) and 2-t-butoxycarbonylamino-1,3-thiazole (252 mg) in the same manner as described for EXAMPLE 15.

MS (FAB$^+$) m/z: 441 (MH$^+$). HRMS (FAB$^+$) for $C_{22}H_{25}N_4O_4S$ (MH$^+$): calcd, 441.1597; found, 441.1607.

EXAMPLE 27

5(S)-5-[N-(t-Butoxycarbonyl)-N-(1,3,4-thiadiazolyl-2-yl)]-3-[4-(1-cyanocyclopropan-1-yl)phenyl] aminomethyloxazolidin-2-one

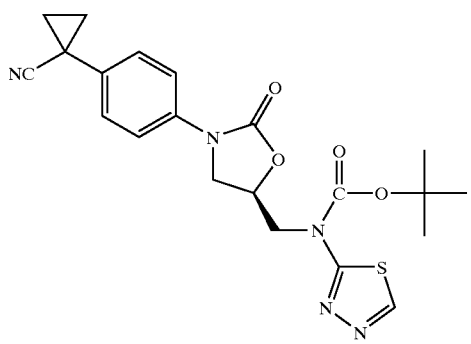

The title compound 5(S)-5-[N-(t-butoxycarbonyl)-N-(1,3,4-thiadiazolyl-2-yl)]-3-[4-(1-cyanocyclopropan-1-yl) phenyl]aminomethyloxazolidin-2-one (359 mg) was prepared from 5(R)-3-[4-(1-cyanocyclopropan-1-yl)phenyl]-5-hydroxymethyloxazolidin-2-one (300 mg) and 2-t-buoxycarbonylamino-1,3,4-thiadiazole (303 mg) in the same manner as described for EXAMPLE 15.

MS (FAB$^+$) m/z: 442 (MH$^+$). HRMS (FAB$^+$) for $C_{21}H_{24}N_5O_4S$ (MH$^+$): calcd, 442.1549; found, 442.1583.

EXAMPLE 28

5(S)-3-[4-(1-Cyanocyclopropan-1-yl)phenyl]-5-[N-(1,3-thiazolyl-2-yl)amino]methyloxazolidin-2-one

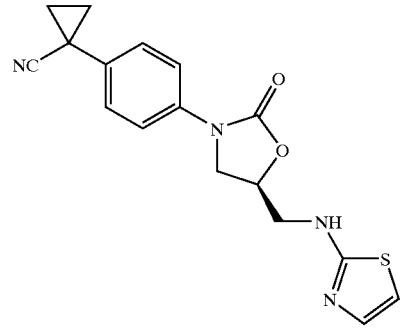

The title compound 5(S)-3-[4-(1-cyanocyclopropan-1-yl) phenyl]-5-[N-(1,3-thiazolyl-2-yl)amino]methyloxazolidin-2-one (190 mg) was prepared from 5(S)-5-[N-(t-butoxycarbonyl)-N-(1,3-thiazolyl-2-yl)]-3-[4-(1-cyanocyclopropan-1-yl)phenyl]aminomethyloxazolidin-2-one (360 mg) in the same manner as described for EXAMPLE 17. MS (EI$^+$) m/z: 340 (M$^+$).

HRMS (EI$^+$) for $C_{17}H_{16}N_4O_2S$ (M$^+$): calcd, 340.0994; found, 340.0979.

EXAMPLE 29

5(S)-3-[4-(1-Cyanocyclopropan-1-yl)phenyl]-5-[N-(1,3,4-thiadiazolyl-2-yl)amino]methyloxazolidin-2-one

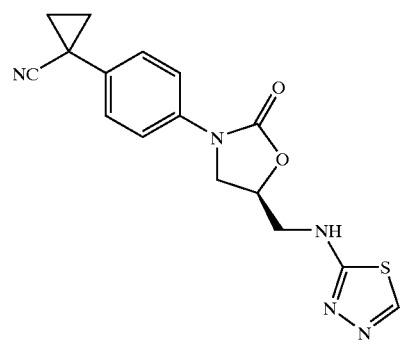

The title compound 5(S)-3-[4-(1-cyanocyclopropan-1-yl) phenyl]-5-[N-(1,3,4-thiadiazolyl-2-yl)amino] methyloxazolidin-2-one (194 mg) was prepared from 5(S)-5-[N-(t-butoxycarbonyl)-N-(1,3,4-thiadiazolyl-2-yl)]-3-[4-(1-cyanocyclopropan-1-yl)phenyl]aminomethyloxazolidin-2-one (353 mg) in the same manner as described for EXAMPLE 17. MS (EI$^+$) m/z: 341 (M$^+$).

HRMS (EI$^+$) for $C_{16}H_{15}N_5O_2S$ (M$^+$): calcd, 341.0946; found, 341.0945.

EXAMPLE 30

S-Methyl N-[5(S)-3-[4-(1-Cyanocyclopropan-1-yl)-3-fluorophenyl]-2-oxooxazolidin-5-ylmethyl]dithiocarbamate

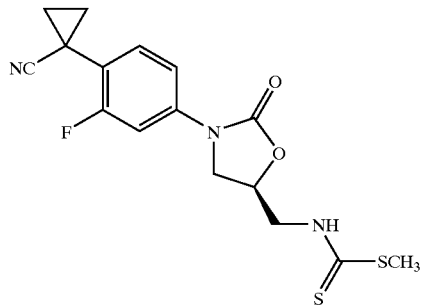

To a solution of crude 5(S)-aminomethyl-3-[4-(1-cyanocyclopropan-1-yl)-3-fluorophenyl]oxazolidin-2-one (prepared from 5(R)-azidomethyl-3-[4-(1-cyanocyclopropan-1-yl)-3-fluorophenyl]oxazolidin-2-one (500 mg) in the same manner as described for EXAMPLE 8) in ethanol (10 mL) and water (2 drops) was added carbon disulfide (0.2 mL) and triethylamnine (0.5 mL) at 0° C., the mixture was stirred at the same temperature for 1 hour, and further stirred at room temperature for 1 hour. To the mixture was added methyl iodide (0.11 mL) at 0° C., the mixture was stirred at the same temperature for 65 min, and further stirred at room temperature for 75 min. The resulting precipitates were collected by filtration, washed with methanol to give S-methyl N-[5(S)-3-[4-(1-cyanocyclopropan-1-yl)-3-fluorophenyl]-2-oxooxazolidin-5-ylmethyl]dithiocarbamate. MS (FAB$^+$) m/z: 366 (MH$^+$).

HRMS (FAB$^+$) for $C_{16}H_{17}FN_3O_2S_2$ (MH$^+$): calcd, 366.0746; found, 366.0749.

EXAMPLE 31

N-[5(S)-3-[4-(1-Cyanocyclopropan-1-yl)-3-fluorophenyl]-2-oxooxazolidin-5-ylmethyl]thiourea

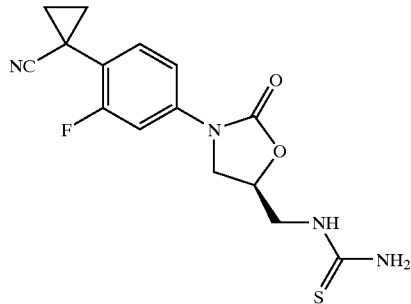

Step 1.
N-[5(R)-3-[4-(1-Cyanocyclopropan-1-yl)-3-fluorophenyl]-2-oxooxazolidin-5-ylmethyl]isothiocyanate.

To a solution of 1,1'-thiocarbonyldi-2(1H)-pyridone (280 mg) in dichloromethane (20 mL) was added a solution of crude 5(S)-aminomethyl-3-[4-(1-cyanocyclopropan-1-yl)-3-fluorophenyl]oxazolidin-2-one (prepared from 5(R)-azidomethyl-3-[4-(1-cyanocyclopropan-1-yl)-3-fluorophenyl]oxazolidin-2-one (300 mg) in the same manner as described for EXAMPLE 9) in dichloromethane (5 mL) at 0° C. for 5 min, and the mixture was stirred at room temperature for 2 hours. The mixture was washed with water and brine, dried over anhydrous sodium sulfate, filtered, and then concentrated in vacuo. Flash chromatography (silica, hexane:ethyl acetate=1:1) of the residue gave N-[5(R)-3-[4-(1-cyanocyclopropan-1-yl)-3-fluorophenyl]-2-oxooxazolidin-5-ylmethyl]isothiocyanate.

Rf=0.36 (hexane:ethyl acetate=1:1).

Step 2.

N-[5(S)-3-[4-(1-Cyanocyclopropan-1-yl)-3-fluorophenyl]-2-oxooxazolidin-5-15 ylmethyl]thiourea.

A solution of N-[5(R)-3-[4-(1-cyanocyclopropan-1-yl)-3-fluorophenyl]-2-oxooxazolidin-5-ylmethyl]isothiocyanate (257 mg) in tetrahydrofuran (5 mL) was saturated with ammonia gas at room temperature for 10 min, and then concentrated in vacuo. Flash chromatography (silica, hexane:ethyl acetate=1:2) of the residue gave N-[5(S)-3-[4-(1-cyanocyclopropan-1-yl)-3-fluorophenyl]-2-oxooxazolidin-5-ylmethyl]thiourea. MS (FAB$^+$) m/z: 335 (MH$^+$).

HRMS (FAB$^+$) for $C_{15}H_{16}FN_4O_2S$ (MH$^+$): calcd, 335.0978; found, 335.0975.

EXAMPLE 32

O-Methyl N-[5(S)-3-[4-(1-Cyanocyclopropan-1-yl)-3-fluorophenyl]-2-oxooxazolidin-5-ylmethyl]thiocarbonate

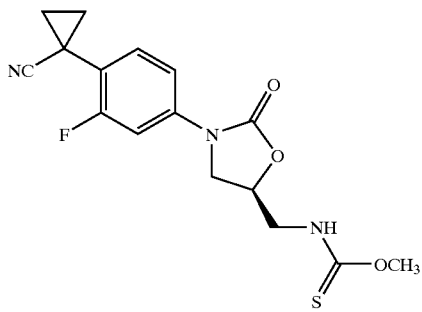

To a solution of sodium hydride (20 mg) in methanol (1 mL) was added a solution of N-[5(R)-3-[4-(1-cyanocyclopropan-1-yl)-3-fluorophenyl]-2-oxooxazolidin-5-ylmethyl]isothiocyanate (40 mg) in methanol (1 mL) at 0° C., and the mixture was stirred at room temperature for 10 min. After quenching the reaction by the addition of saturated ammonium chloride solution, the resulting precipitates were collected by filtration, washed with water, and then dried to give O-methyl N-[5(S)-3-[4-(1-cyanocyclopropan-1-yl)-3-fluorophenyl]-2-oxooxazolidin-5-ylmethyl]thiocarbonate (36 mg). MS (EI$^+$) m/z: 349 (M$^+$).

HRMS (EI$^+$) for $C_{16}H_{16}FN_3O_3S$ (M$^+$): calcd, 349.0896; found, 349.0930.

EXAMPLE 33

N'-Methyl N-[5(S)-3-[4-(1-Cyanocyclopropan-1-yl)-3-fluorophenyl]-2-oxooxazolidin-5-ylmethyl]thiourea

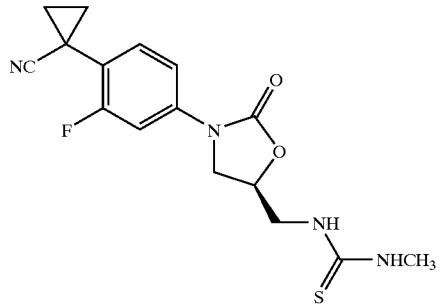

To a solution of methyl isothiocyanate (80 mg) in tetrahydrofuran (4 mL) was added a solution of crude 5(S)-aminomethyl-3-[4-(1-cyanocyclopropan-1-yl)-3-fluorophenyl]oxazolidin-2-one (prepared from 5(R)-azidomethyl-3-[4-(1-cyanocyclopropan-1-yl)-3-fluorophenyl]oxazolidin-2-one (250 mg) in the same manner as described for EXAMPLE 9) in tetrahydrofuran (4 mL) at room temperature, the mixture was stirred at the same temperature for 16.5 hours, and then concentrated in vacuo. Flash chromatography (silica, dichloromethane:methanol= 20:1) of the residue gave N'-methyl N-[5(S)-3-[4-(1-cyanocyclopropan-1-yl)-3-fluorophenyl]-2-oxooxazolidin-5-ylmethyl]thiourea (250 mg).

MS (FAB$^+$) m/z: 349 (MH$^+$). HRMS (FAB$^+$) for $C_{16}H_{18}FN_4O_2S$ (MH$^+$): calcd, 349.1135; found, 349.1129.

EXAMPLE 34

O-Methyl N-[5(S)-3-[4-(1-Cyanocyclopropan-1-yl)phenyl]-2-oxooxazolidin-5-ylmethyl]thiocarbonate

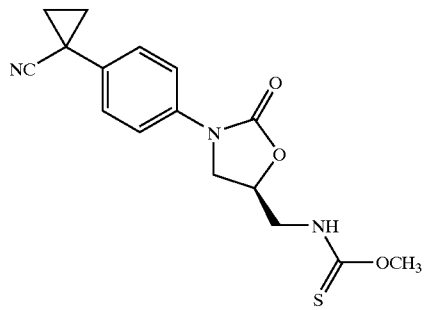

The title compound O-methyl N-[5(S)-3-[4-(1-cyanocyclopropan-1-yl)phenyl]-2-oxooxazolidin-5-ylmethyl]thiocarbonate (272 mg) was prepared from 5(R)-azidomethyl-3-[4-(1-cyanocyclopropan-1-yl)-3-fluorophenyl]oxazolidin-2-one (300 mg) in the same manner as described for EXAMPLES 31 and 32.

MS (EI$^+$) m/z: 331 (M$^+$). HRMS (EI$^+$) for $C_{16}H_{17}N_3O_3S$ (M$^+$): calcd, 331.0991; found, 331.1004.

EXAMPLE 35

N'-Cyano N-[5(S)-3-[4-(1-Cyanocyclopropan-1-yl)phenyl]-2-oxooxazolidin-5-ylmethyl]acetamidine

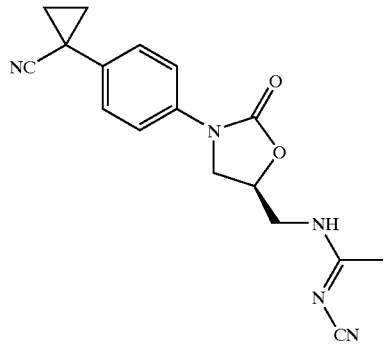

To a solution of crude 5(S)-aminomethyl-3-[4-(1-cyanocyclopropan-1-yl)phenyl]oxazolidin-2-one (prepared from 5(R)-azidomethyl-3-[4-(1-cyanocyclopropan-1-yl)phenyl]oxazolidin-2-one (227 mg) in methanol (10 mL) and tetrahydrofuran (2 mL) was added O-methyl N-cyanoacetamide (118 mg), the mixture was stirred at room temperature for 1 day, and then concentrated in vacuo. After treating the residue with methanol, the resulting precipitates were collected by filtration, washed with methanol to give N'-cyano N-[5(S)-3-[4-(1-cyanocyclopropan-1-yl)phenyl]-2-oxooxazolidin-5-ylmethyl]acetamidine (183 mg).

MS (FAB$^+$) m/z: 324 (MH$^+$). HRMS (FAB$^+$) for $C_{17}H_{18}N_5O_2$ (MH$^+$): calcd, 324.1460; found, 324.1464.

EXAMPLE 36

N'-Cyano N-[5(S)-3-[4-(1-Cyanocyclopropan-1-yl)-3-fluorophenyl]-2-oxooxazolidin-5-ylmethyl]acetamidine

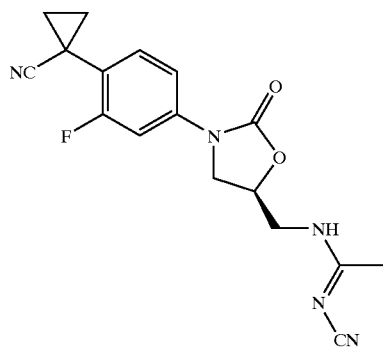

The title compound N'-cyano N-[5(S)-3-[4-(1-cyanocyclopropan-1-yl)-3-fluorophenyl]-2-oxooxazolidin-5-ylmethyl]acetamidine (93 mg) was prepared from 5(R)-azidomethyl-3-[4-(1-cyanocyclopropan-1-yl)-3-fluorophenyl]oxazolidin-2-one (121 mg) in the same manner as described for EXAMPLE 35.

MS (FAB$^+$) m/z: 342 (MH$^+$). HRMS (FAB$^+$) for $C_{17}H_{17}FN_5O_2$ (MH$^+$): calcd, 342.1366; found, 342.1350.

EXAMPLE 37

1-[5(R)-3-[4-(1-Cyanocyclopropan-1-yl)phenyl]-2-oxooxazolidin-5-ylmethyl]-1,2,3-triazole

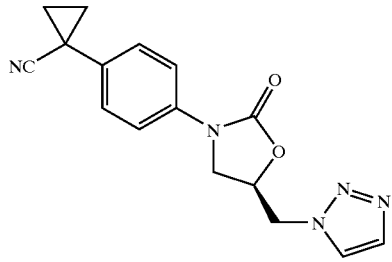

To a solution of 5(R)-azidomethyl-3-[4-(1-cyanocyclopropan-1-yl)phenyl]oxazolidin-2-one (300 mg) in dioxane (10 mL) was added 2,5-norbornadiene (0.6 mL), the mixture was heated under reflux for 4.5 hours, and then concentrated in vacuo. After dilution of the residue with dichloromethane, the mixture was washed with water, dried over anhydrous magnesium sulfate, filtered, and then concentrated in vacuo. Flash chromatography (silica, ethyl acetate) of the residue gave 1-[5(R)-3-[4-(1-cyanocyclopropan-1-yl)phenyl]-2-oxooxazolidin-5-ylmethyl]-1,2,3-triazole (190 mg).

MS (EI$^+$) m/z: 309 (M$^+$). HRMS (EI$^+$) for C16H15N5O2 (M$^+$): calcd, 309.1226; found, 309.1200.

EXAMPLE 38

5-Amino-4-cyano-1-[5(R)-3-[4-(1-cyanocyclopropan-1-yl)phenyl]-2-oxooxazolidin-5-ylmethyl]-1,2,3-triazole

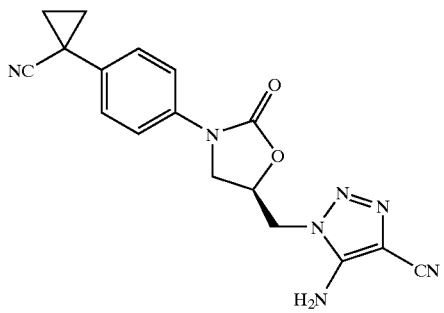

To a suspension of potassium carbonate (440 mg) in dimethyl sulfoxide (8 mL) was added a solution of 5(R)-azidomethyl-3-[4-(1-cyanocyclopropan-1-yl)phenyl]oxazolidin-2-one (300 mg) and malononitrile (105 mg) in dimethyl sulfoxide (10 mL) at room temperature, the mixture was stirred at the same temperature for 32.3 hours. After dilution of the mixture with water, the resulting precipitates were collected by filtration to give 5-amino-4-cyano-1-[5(R)-3-[4-(1-cyanocyclopropan-1-yl)phenyl]-2-oxooxazolidin-5-ylmethyl]-1,2,3-triazole (223 mg).

MS (EI$^+$) m/z: 349 (M$^+$). HRMS (EI$^+$) for C17H15N7O2 (M$^+$): calcd, 349.1287; found, 349.1292.

EXAMPLE 39

1-[5(R)-3-[4-(1-Cyanocyclopropan-1-yl)phenyl]-2-oxooxazolidin-5-ylmethyl]-5-methyl-1,2,3-triazole

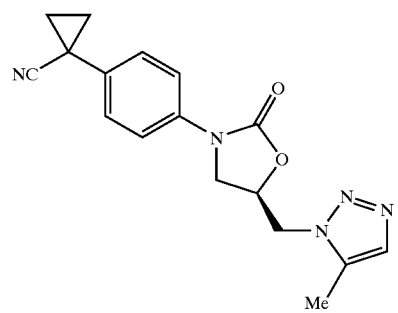

A solution of 5(R)-azidomethyl-3-[4-(1-cyanocyclopropan-1-yl)phenyl]oxazolidin-2-one (300 mg) and 1-triphenylphosphoranylidene-2-propanone (343 mg) in benzene (25 mL) was heated under reflux for 33 hours, and then concentrated in vacuo. After dilution of the residue with ethyl acetate, the resulting precipitates were collected by filtration to give 1-[5(R)-3-[4-(1-cyanocyclopropan-1-yl)phenyl]-2-oxooxazolidin-5-ylmethyl]-5-methyl-1,2,3-triazole (230 mg).

MS (EI$^+$) m/z: 323 (M$^+$). HRMS (EI$^+$) for C17H17N5O2 (M$^+$): calcd, 323.1382; found, 323.1369.

EXAMPLE 40

1-[5(R)-3-[4-(1-Cyanocyclopropan-1-yl)phenyl]-2-oxooxazolidin-5-ylmethyl]-4-methyl-1,2,3-triazole

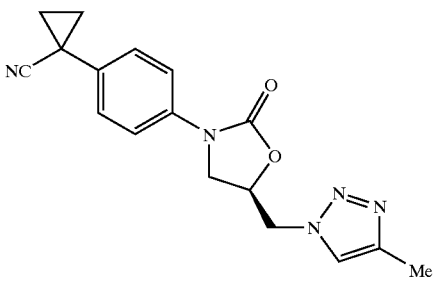

A solution of 5(S)-aminomethyl-3-[4-(1-cyanocyclopropan-1-yl)phenyl]oxazolidin-2-one (880 mg) in methanol (20 mL) was added a solution of 1,1-dichloroacetone tosylhydrazone (260 mg) in methanol (20 mL) at 0° C., the mixture was stirred at the same temperature for 1 hour, and then concentrated in vacuo. After dilution of the residue with dichloromethane, the resulting precipitates were filtered off. Flash chromatography (silica, ethyl acetate) of the filtrate gave 1-[5(R)-3-[4-(1-cyanocyclopropan-1-yl)phenyl]-2-oxooxazolidin-5-ylmethyl]-4-methyl-1,2,3-triazole (250 mg).

MS (EI$^+$) m/z: 323 (M$^+$). HRMS (EI$^+$) for C17H17N5O2 (M$^+$): calcd, 323.1382; found, 323.1377.

EXAMPLE 41

1-[5(R)-3-[4-(1-Cyanocyclopropan-1-yl)-3-fluorophenyl]-2-oxooxazolidin-5-ylmethyl]-1,2,3-triazole

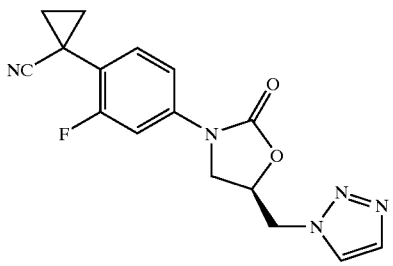

The title compound 1-[5(R)-3-[4-(1-cyanocyclopropan-1-yl)-3-fluorophenyl]-2-oxooxazolidin-5-ylmethyl]-1,2,3-triazole (284 mg) was prepared from 5(R)-azidomethyl-3-[4-(1-cyanocyclopropan-1-yl)-3-fluorophenyl]oxazolidin-2-one (300 mg) in the same manner as described for EXAMPLE 37.

MS (EI$^+$) m/z: 327 (M$^+$). HRMS (EI$^+$) for C16H14FN5O2 (M$^+$): calcd, 327.1132; found, 327.1135.

EXAMPLE 42

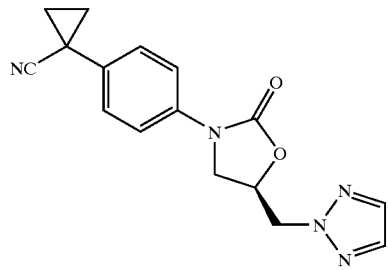

1-[5(R)-3-[4-(1-Cyanocyclopropan-1-yl)phenyl]-2-oxooxazolidin-5-ylmethyl]-1,2,5-triazole Step 1.
5(R)-3-[4-[(1-Cyanocyclopropan-1-yl)phenyl]-5-methanesulfonyloxymethyloxazolidin-2-one.

To a solution of 5(R)-3-[4-(1-cyanocyclopropan-1-yl)phenyl]-5-hydroxymethyloxazolidin-2-one (2.00 g) and triethylamine (2.0 mL) in tetrahydrofuran (40 mL) was added methanesulfonyl chloride (0.75 mL) at 0° C., the mixture was stirred at the same temperature for 25 min. After dilution with ice water, the mixture was extracted with ethyl acetate. The organic extracts were washed with brine, dried over anhydrous magnesium sulfate, filtered, and then concentrated in vacuo. Treatment of the residue with ethyl acetate gave 5(R)-3-[4-[(1-cyanocyclopropan-1-yl)phenyl]-5-methanesulfonyloxymethyloxazolidin-2-one (2.51 g).

Step 2.
1-[5(R)-3-[4-(1-Cyanocyclopropan-1-yl)phenyl]-2-oxooxazolidin-5-ylmethyl]-1,2,5-triazole.

To suspension of sodium hydride (120 mg) in dimethylformamide (15 mL) was added 1H-1,2,3-triazole (150 μL), the mixture was stirred at room temperature for 10 min. A solution of 5(R)-3-[4-[(1-cyanocyclopropan-1-yl)phenyl]-5-methanesulfonyloxymethyloxazolidin-2-one (500 mg) in dimethylformamide (15 mL) was added to the resulting mixture, the mixture was stirred at 80° C. for 4.5 hours. After quenching the reaction by adding 10% sodium carbonate solution, the mixture was extracted with ethyl acetate. The organic extracts were washed with brine, dried over anhydrous magnesium sulfate, filtered, and then concentrated in vacuo. Flash chromatography (silica, ethyl acetate) of the residue gave 1-[5(R)-3-[4-(1-cyanocyclopropan-1-yl)phenyl]-2-oxooxazolidin-5-ylmethyl]-1,2,5-triazole (291 mg).

MS (EI$^+$) m/z: 309 (M$^+$). HRMS (EI$^+$) for C16H15N5O2 (M$^+$): calcd, 309.1226; found, 309.1208.

EXAMPLE 43

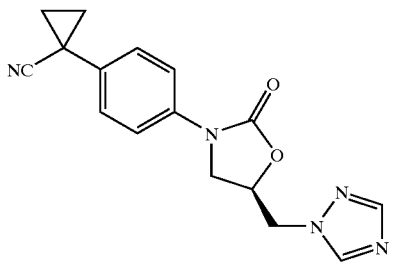

1-[5(R)-3-[4-(1-Cyanocyclopropan-1-yl)phenyl]-2-oxooxazolidin-5-ylmethyl]-1,2,4-triazole To the mixture of 5(R)-3-[4-(1-cyanocyclopropan-1-yl)phenyl]-5-hydroxymethyloxazolidin-2-one (50 mg), tetramethylazodicarboxamide (50 mg) and 1,2,4-triazole (16 mg) in benzene (2 mL) was added butylphosphine (0.09 mL), the mixture was stirred at 70° C. for 19 hours, and then concentrated in vacuo. Flash chromatography (silica, ethyl acetate:methanol=20:1) of the residue gave 1-[5(R)-3-[4-(1-cyanocyclopropan-1-yl)phenyl]-2-oxooxazolidin-5-ylmethyl]-1,2,4-triazole (47 mg).

MS (EI$^+$) m/z: 309 (M$^+$). HRMS (EI$^+$) for C16H15N5O2 (M$^+$): calcd, 309.1226; found, 309.1232.

EXAMPLE 44

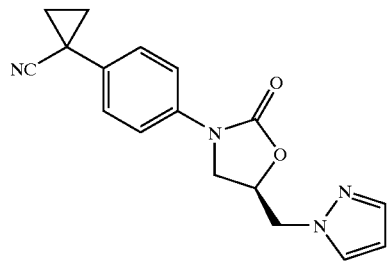

1-[5(R)-3-[4-(1-Cyanocyclopropan-1-yl)phenyl]-2-oxooxazolidin-5-ylmethyl]-1,2-prazole The title compound 1-[5(R)-3-[4-(1-cyanocyclopropan-1-yl)phenyl]-2-oxooxazolidin-5-ylmethyl]-1,2-prazole (240 mg) was prepared from 5(R)-3-[4-(1-cyanocyclopropan-1-yl)phenyl]-5-hydroxymethyloxazolidin-2-one (250 mg and pyrazole (80 mg) in the same manner as described for EXAMPLE 43.

MS (EI$^+$) m/z: 308 (M$^+$). HRMS (EI$^+$) for C17H16N4O2 (M$^+$): calcd, 308.1273; found, 308.1309.

EXAMPLE 45

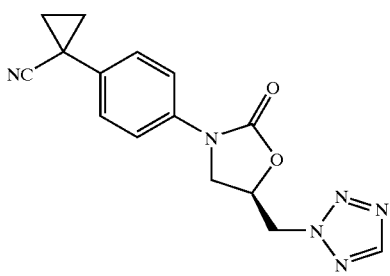

2-[5(R)-3-[4-(1-Cyanocyclopropan-1-yl)phenyl]-2-oxooxazolidin-5-ylmethyl]tetrazole The title compound 2-[5(R)-3-[4-(1-cyanocyclopropan-1-yl)phenyl]-2-oxooxazolidin-5-ylmethyl]tetrazole (252 mg) was prepared from 5(R)-3-[4-(1-cyanocyclopropan-1-yl)phenyl]-5-hydroxymethyloxazolidin-2-one (250 mg) and 1H-tetrazole (88 mg) in the same manner as described for EXAMPLE 43.

MS (EI$^+$) m/z: 310 (M$^+$). HRMS (EI$^+$) for C15H14N6O2 (M$^+$): calcd, 310.1178; found, 310.1161.

EXAMPLE 46

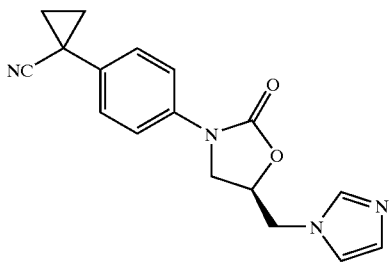

1-[5(R)-3-[4-(1-Cyanocyclopropan-1-yl)phenyl]-2-oxooxazolidin-5-ylmethyl]-1,3-imidazole The title compound 1-[5(R)-3-[4-(1-cyanocyclopropan-1-yl)phenyl]-2-oxooxazolidin-5-ylmethyl]-1,3-imidazole (34 mg) was prepared from 5(R)-3-[4-[(1-cyanocyclopropan-1-yl)phenyl]-5-methanesulfonyloxymethyloxazolidin-2-one (70 mg) and imidazole (28 mg) in the same manner as described for EXAMPLE 42.

MS (EI$^+$) m/z: 308 (M$^+$). HRMS (EI$^+$) for C17H16N4O2 (M$^+$): calcd, 308.1273; found, 308.1288.

EXAMPLE 47

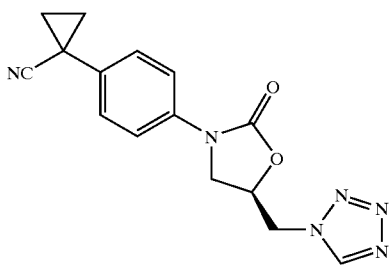

1-[5(R)-3-[4-(1-Cyanocyclopropan-1-yl)phenyl]-2-oxooxazolidin-5-ylmethyl]tetrazole The title compound 1-[5(R)-3-[4-(1-cyanocyclopropan-1-yl)phenyl]-2-oxooxazolidin-5-ylmethyl]tetrazole (165 mg) was prepared from 5(R)-3-[4-[(1-cyanocyclopropan-1-yl)phenyl]-5-methanesulfonyloxymethyloxazolidin-2-one (600 mg) and 1H-tetrazole (244 mg) in the same manner as described for EXAMPLE 42

MS (EI$^+$) m/z: 310 (M$^+$). HRMS (EI$^+$) for C15H14N6O2 (M$^+$): calcd, 310.1178; found, 310.1170.

EXAMPLE 48

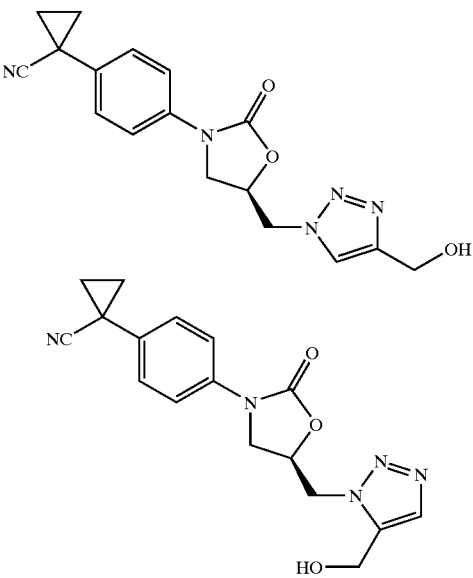

1-[5(R)-3-[4-(1-Cyanocyclopropan-1-yl)phenyl]-2-oxooxazolidin-5-ylmethyl]-4-hydroxymethyl-1,2,3-triazole and 1-[5(R)-3-[4-(1-Cyanocyclopropan-1-yl)phenyl]-2-oxooxazolidin-5-ylmethyl]-5-hydroxymethyl-1,2,3-triazole To a solution of 5(R)-azidomethyl-3-[4-(1-cyanocyclopropan-1-yl)phenyl]oxazolidin-2-one (100 mg) in toluene (5 mL) was added propagyl alcohol (23 μL), the mixture was heated under reflux for 36 hours. After dilution of the residue with water, the mixture was extracted with dichloromethane. The organic extracts were washed with brine, dried over anhydrous magnesium sulfate, filtered, and then concentrated in vacuo. Flash chromatography (silica, ethyl acetate:methanol=20:1) of the residue gave 1-[5(R)-3-[4-(1-cyanocyclopropan-1-yl)phenyl]-2-oxooxazolidin-5-ylmethyl]-4-hydroxymethyl-1,2,3-triazole (56 mg) and 1-[5(R)-3-[4-(1-cyanocyclopropan-1-yl)phenyl]-2-oxooxazolidin-5-ylmethyl]-5-hydroxymethyl-1,2,3-triazole (37 mg).

1-[5(R)-3-[4-(1-Cyanocyclopropan-1-yl)phenyl]-2-oxooxazolidin-5-ylmethyl]-4-hydroxymethyl-1,2,3-triazole:

MS (EI$^+$) m/z: 339 (M$^+$). HRMS (EI$^+$) for C17H17N5O3 (M$^+$): calcd, 339.1331; found, 339.1319.

1-[5(R)-3-[4-(1-Cyanocyclopropan-1-yl)phenyl]-2-oxooxazolidin-5-ylmethyl]-5-hydroxymethyl-1,2,3-triazole:

MS (EI$^+$) m/z: 339 (M$^+$). HRMS (EI$^+$) for C17H17N5O3 (M$^+$): calcd, 339.1331; found, 339.1303.

EXAMPLE 49

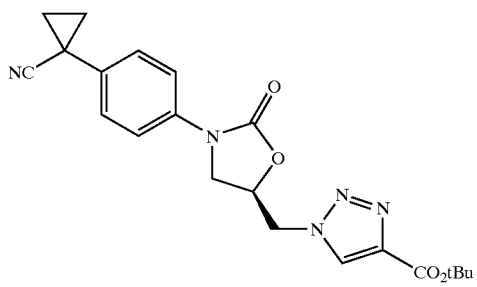

t-Butyl 1-[5(R)-3-[4-(1-Cyanocyclopropan-1-yl)
phenyl]-2-oxooxazolidin-5-ylmethyl]-1,2,3-triazole-
4-carboxylate To a suspension of copper(I) iodide (335 mg) in tetrahydrofuran (100 mL) was added t-butyl propiolate (3.63 mL), diisopropylethylamine (4.62 mL) and a solution of 5(R)-azidomethyl-3-[4-(1-cyanocyclopropan-1-yl)phenyl] oxazolidin-2-one (5.00 g) in tetrahydrofuran (10 mL), the mixture was stirred at room temperature for 2.5 hours, and then concentrated in vacuo. After dilution of the residue with ethyl acetate, the resulting precipitates were filtered off, and then concentrated in vacuo. Treatment of the residue with ethyl acetate gave t-butyl 1-[5(R)-3-[4-(1-cyanocyclopropan-1-yl)phenyl]-2-oxooxazolidin-5-ylmethyl]-1,2,3-triazole-4-carboxylate (6.85 g).

MS (EI$^+$) m/z: 409 (M$^+$). HRMS (EI$^+$) for C21H23N5O4 (M$^+$): calcd, 409.1750; found, 409.1729.

EXAMPLE 50

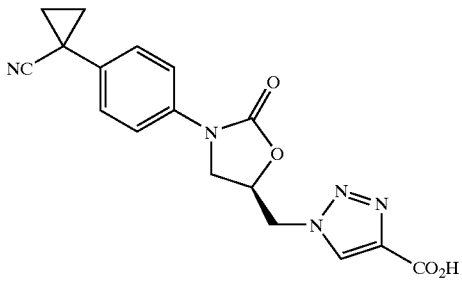

1-[5(R)-3-[4-(1-Cyanocyclopropan-1-yl)phenyl]-2-
oxooxazolidin-5-ylmethyl]-1,2,3-triazole-4-
carboxylic Acid The title compound 1-[5(R)-3-[4-(1-cyanocyclopropan-1-yl)phenyl]-2-oxooxazolidin-5-ylmethyl]-1,2,3-triazole-4-carboxylic acid (3.82 g) was prepared from t-butyl 1-[5(R)-3-[4-(1-cyanocyclopropan-1-yl)phenyl]-2-oxooxazolidin-5-ylmethyl]-1,2,3-triazole-4-carboxylate (4.45 g) in the same manner as described for EXAMPLE 2.

MS (FAB$^+$) m/z: 354 (MH$^+$). HRMS (FAB$^+$) for C17H16N5O4 (MH$^+$): calcd, 354.1202; found, 354.1197.

EXAMPLE 51

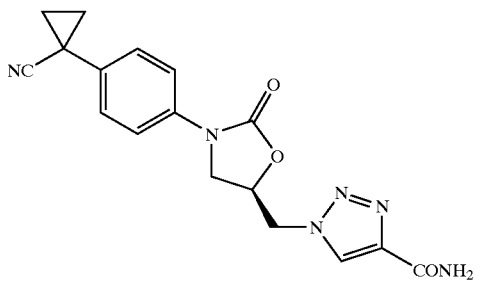

1-[5(R)-3-[4-(1-Cyanocyclopropan-1-yl)phenyl]-2-
oxooxazolidin-5-ylmethyl]-1,2,3-triazole-4-
carboxamide To a solution of 1-[5(R)-3-[4-(1-cyanocyclopropan-1-yl) phenyl]-2-oxooxazolidin-5-ylmethyl]-1,2,3-triazole-4-carboxylate (600 mg) in dimethylformamide (10 mL) was added N-hydroxysuccinimide (293 mg) and 1-[3-(dimethylamino)propyl]-3-ethylcarbodiimide hydrochloride (487 mg), the mixture was stirred at room temperature for 5 hours. The resulting solution was added 25% ammonium hydroxide solution (0.58 mL), the mixture was stirred at room temperature for 2 hours, and then concentrated in vacuo. After dilution of the residue with saturated sodium hydrogen carbonate solution and water, the resulting precipitates were collected by filtration to give 1-[5(R)-3-[4-(1-cyanocyclopropan-1-yl)phenyl]-2-oxooxazolidin-5-ylmethyl]-1,2,3-triazole-4-carboxamide (485 mg).

MS (EI$^+$) m/z: 352 (M$^+$). HRMS (EI$^+$) for C17H16N6O3 (M$^+$): calcd, 352.1284; found, 352.1290.

EXAMPLE 52

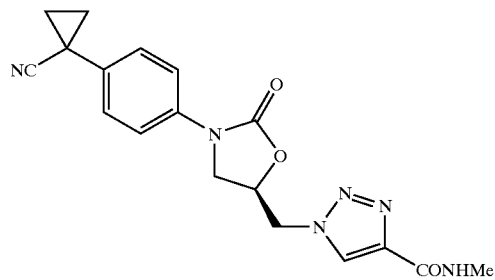

1-[5(R)-3-[4-(1-Cyanocyclopropan-1-yl)phenyl]-2-
oxooxazolidin-5-ylmethyl]-N-methyl-1,2,3-triazole-
4-carboxamide The title compound N-methyl 1-[5(R)-3-[4-(1-cyanocyclopropan-1-yl)phenyl]-2-oxooxazolidin-5-ylmethyl]-1,2,3-triazole-4-carboxamide (356 mg) was prepared from 1-[5(R)-3-[4-(1-cyanocyclopropan-1-yl) phenyl]-2-oxooxazolidin-5-ylmethyl]-1,2,3-triazole-4-carboxylate (400 mg) and methylamine (2.83 mL, 2.0 M solution in tetrahydrofuran) in the same manner as described for EXAMPLE 51.

MS (EI$^+$) m/z: 366 (M$^+$). HRMS (EI$^+$) for C18H18N6O3 (M$^+$): calcd, 366.1440; found, 366.1422.

EXAMPLE 53

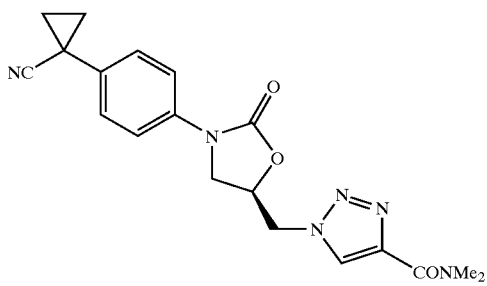

1-[5(R)-3-[4-(1-Cyanocyclopropan-1-yl)phenyl]-2-oxooxazolidin-5-ylmethyl]-N,N-dimethyl-1,2,3-triazole-4-carboxamide The title compound N,N-dimethyl 1-[5(R)-3-[4-(1-cyanocyclopropan-1-yl)phenyl]-2-oxooxazolidin-5-ylmethyl]-1,2,3-triazole-4-carboxamide (360 mg) was prepared from 1-[5(R)-3-[4-(1-cyanocyclopropan-1-yl)phenyl]-2-oxooxazolidin-5-ylmethyl]-1,2,3-triazole-4-carboxylate (400 mg), dimethylamine hydrochloride (401 mg) and triethylamine (0.79 mL) in the same manner as described for EXAMPLE 51.

MS (EI$^+$) m/z: 380 (M$^+$). HRMS (EI$^+$) for C19H20N6O3 (M$^+$): calcd, 380.1597; found, 380.1618.

EXAMPLE 54

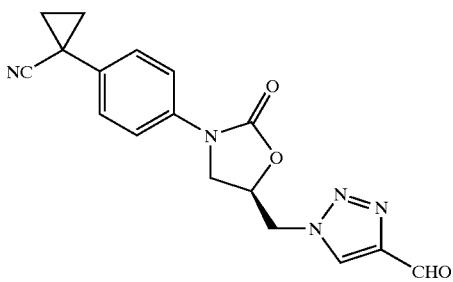

1-[5(R)-3-[4-(1-Cyanocyclopropan-1-yl)phenyl]-2-oxooxazolidin-5-ylmethyl]-1,2,3-triazole-4-carboxaldehyde The title compound 1-[5(R)-3-[4-(1-cyanocyclopropan-1-yl)phenyl]-2-oxooxazolidin-5-ylmethyl]-1,2,3-triazole-4-carboxaldehyde (95.3 mg) was prepared from 1-[5(R)-3-[4-(1-cyanocyclopropan-1-yl)phenyl]-2-oxooxazolidin-5-ylmethyl]-4-hydroxymethyl-1,2,3-triazole (100 mg) in the same manner as described for EXAMPLE 5.

MS (EI$^+$) m/z: 337 (M$^+$). HRMS (EI$^+$) for C17H15N5O3 (M$^+$): calcd, 337.1175; found, 337.1175.

EXAMPLE 55

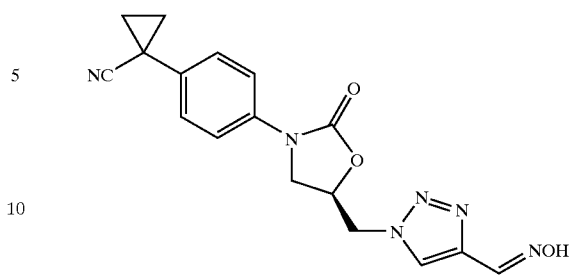

1-[5(R)-3-[4-(1-Cyanocyclopropan-1-yl)phenyl]-2-oxooxazolidin-5-ylmethyl]-4-(hydroxyimino)methyl-1,2,3-triazole The title compound 1-[5(R)-3-[4-(1-cyanocyclopropan-1-yl)phenyl]-2-oxooxazolidin-5-ylmethyl]-4-(hydroxyimino)methyl-1,2,3-triazole (1.00 g) was prepared from 1-[5(R)-3-[4-(1-cyanocyclopropan-1-yl)phenyl]-2-oxooxazolidin-5-ylmethyl]-1,2,3-triazole-4-carboxaldehyde (1.00 g) in the same manner as described for EXAMPLE 6.

MS (FAB$^+$) m/z: 353 (MH$^+$). HRMS (FAB$^+$) for C17H17N6O3 (MH$^+$): calcd, 353.1362; found, 353.1381.

EXAMPLE 56

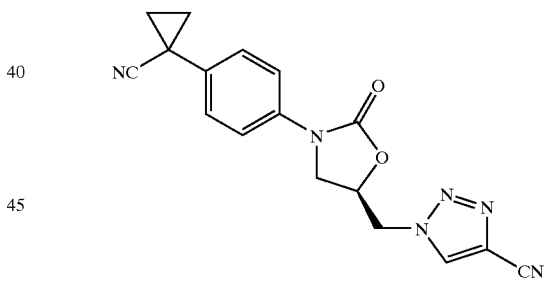

4-Cyano-1-[5(R)-3-[4-(1-cyanocyclopropan-1-yl)phenyl]-2-oxooxazolidin-5-ylmethyl]-1,2,3-triazole The title compound 4-cyano-1-[5(R)-3-[4-(1-cyanocyclopropan-1-yl)phenyl]-2-oxooxazolidin-5-ylmethyl]-1,2,3-triazole (379 mg) was prepared from 1-[5(R)-3-[4-(1-cyanocyclopropan-1-yl)phenyl]-2-oxooxazolidin-5-ylmethyl]-4-(hydroxyimino)methyl-1,2,3-triazole (450 mg) in the same manner as described for EXAMPLE 7.

MS (EI$^+$) m/z: 334 (M$^+$). HRMS (EI$^+$) for C17H14N6O2 (M$^+$): calcd, 334.1178; found, 334.1160.

EXAMPLE 57

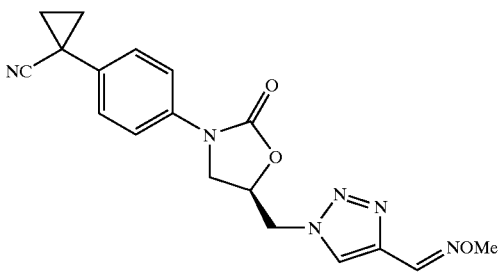

1-[5(R)-3-[4-(1-Cyanocyclopropan-1-yl)phenyl]-2-oxooxazolidin-5-ylmethyl]-4-(methoxyimino)methyl-1,2,3-triazole The title compound 1-[5(R)-3-[4-(1-cyanocyclopropan-1-yl)phenyl]-2-oxooxazolidin-5-ylmethyl]-4-(methoxyimino)methyl-1,2,3-triazole (316 mg) was prepared from 1-[5(R)-3-[4-(1-cyanocyclopropan-1-yl)phenyl]-2-oxooxazolidin-5-ylmethyl]-1,2,3-triazole-4-carboxaldehyde (300 mg) and O-methylhydroxylamine hydrochloride (223 mg) in the same manner as described for EXAMPLE 6.

EXAMPLE 58

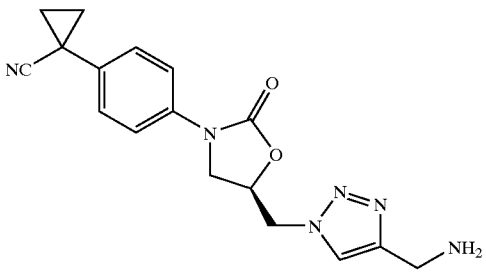

4-Aminomethyl-1-[5(R)-3-[4-(1-cyanocyclopropan-1-yl)phenyl]-2-oxooxazolidin-5-ylmethyl]-1,2,3-triazole Step 1.
4-Azidomethyl-1-[5(R)-3-[4-(1-cyanocyclopropan-1-yl)phenyl]-2-oxooxazolidin-5-ylmethyl]-1,2,3-triazole.

The title compound 4-azidomethyl-1-[5(R)-3-[4-(1-cyanocyclopropan-1-yl)phenyl]-2-oxooxazolidin-5-ylmethyl]-1,2,3-triazole (1.50 g) was prepared from 1-[5(R)-3-[4-(1-cyanocyclopropan-1-yl)phenyl]-2-oxooxazolidin-5-ylmethyl]-4-hydroxymethyl-1,2,3-triazole (1.50 g) in the same manner as described for EXAMPLE 1.

MS (EI$^+$) m/z: 364 (M$^+$). HRMS (EI$^+$) for C17H16N8O2 (M$^+$): calcd, 364.1396; found, 364.1364.

Step 2.
4-Aminomethyl-1-[5(R)-3-[4-(1-cyanocyclopropan-1-yl)phenyl]-2-oxooxazolidin-5-ylmethyl]-1,2,3-triazole.

To a solution of 4-azidomethyl-1-[5(R)-3-[4-(1-cyanocyclopropan-1-yl)phenyl]-2-oxooxazolidin-5-ylmethyl]-1,2,3-triazole (900 mg) in tetrahydrofuran (30 mL) was added triphenylphosphine (842 mg), the mixture was stirred at room temperature for 9.2 hours. The resulting mixture was heated under reflux for 7 hours, and then concentrated in vacuo. After dilution of the residue with 6 N hydrochloric acid and water, the mixture was washed with ethyl acetate. The aqueous solution was made to alkaline by the addition of saturated sodium hydrogencarbonate solution and sodium carbonate. The resulting mixture was extracted with dichloromethane-methanol (5:1). The organic extracts were washed with brine, dried over anhydrous magnesium sulfate, filtered, and then concentrated in vacuo to give 4-aminomethyl-1-[5(R)-3-[4-(1-cyanocyclopropan-1-yl)phenyl]-2-oxooxazolidin-5-ylmethyl]-1,2,3-triazole (790 mg).

MS (FAB$^+$) m/z: 339 (MH$^+$). HRMS (FAB$^+$) for C17H19N6O2 (MH$^+$): calcd, 339.1569; found, 339.1562.

EXAMPLE 59

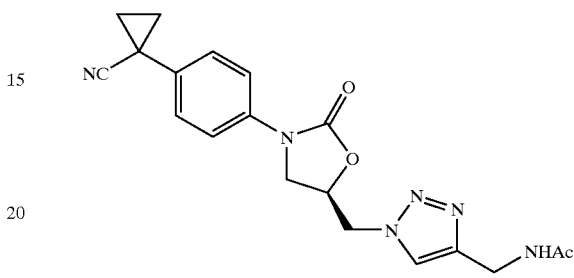

4-Acetoamidomethyl-1-[5(R)-3-[4-(1-cyanocyclopropan-1-yl)phenyl]-2-oxooxazolidin-5-ylmethyl]-1,2,3-triazole To a suspension of 4-aminomethyl-1-[5(R)-3-[4-(1-cyanocyclopropan-1-yl)phenyl]-2-oxooxazolidin-5-ylmethyl]-1,2,3-triazole (300 mg) in tetrahydrofuran (15 mL) was added a solution of triethylamine (197 mg) in tetrahydrofuran (1 mL) and a solution of acetic anhydride (109 mg) in tetrahydrofuran (1 mL), the mixture was stirred at room temperature for 15 min, and then concentrated in vacuo. Treatment of the residue with diethyl ether gave 4-acetoamidomethyl-1-[5(R)-3-[4-(1-cyanocyclopropan-1-yl)phenyl]-2-oxooxazolidin-5-ylmethyl]-1,2,3-triazole (304 mg).

MS (EI$^+$) m/z: 380 (M$^+$). HRMS (EI$^+$) for C19H20N6O3 (M$^+$): calcd, 380.1597; found, 380.1592.

EXAMPLE 60

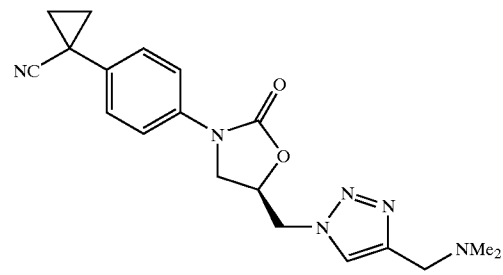

1-[5(R)-3-[4-(1-Cyanocyclopropan-1-yl)phenyl]-2-oxooxazolidin-5-ylmethyl]-4-dimethylaminomethyl-1,2,3-triazole Step 1.
1-[5(R)-3-[4-(1-Cyanocyclopropan-1-yl)phenyl]-2-oxooxazolidin-5-ylmethyl]-4-methanesulfonyloxymethyl-1,2,3-triazole.

The title compound 1-[5(R)-3-[4-(1-cyanocyclopropan-1-yl)phenyl]-2-oxooxazolidin-5-ylmethyl]-4-methanesulfonyloxymethyl-1,2,3-triazole (979 mg) was prepared from 1-[5(R)-3-[4-(1-cyanocyclopropan-1-yl)

phenyl]-2-oxooxazolidin-5-ylmethyl]-4-hydroxymethyl-1,2,3-triazole (811 mg) in the same manner as described for EXAMPLE 42.

Step 2.

1-[5(R)-3-[4-(1-Cyanocyclopropan-1-yl)phenyl]-2-oxooxazolidin-5-ylmethyl]-4-dimethylaminomethyl-1,2,3-triazole.

To a solution of dimethylamine (2.0 M, 8.38 mL) in tetrahydrofuran was added 1-[5(R)-3-[4-(1-cyanocyclopropan-1-yl)phenyl]-2-oxooxazolidin-5-ylmethyl]-4-methanesulfonyloxymethyl-1,2,3-triazole at room temperature for 1 hour, the mixture was stirred at the same temperature for 10 min. The resulting precipitates were collected by filtration. Flash chromatography (NH silica, dichloromethane:methanol=40:1) of the precipitates gave 1-[5(R)-3-[4-(1-cyanocyclopropan-1-yl)phenyl]-2-oxooxazolidin-5-ylmethyl]-4-dimethylaminomethyl-1,2,3-triazole (270 mg).

MS (EI$^+$) m/z: 366 (M$^+$). HRMS (EI$^+$) for C19H22N6O2 (M$^+$): calcd, 366.1804; found, 366.1778.

EXAMPLE 61

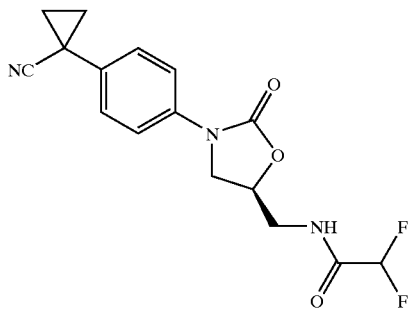

N-[5(S)-3-[4-(1-Cyanocyclopropan-1-yl)phenyl]-2-oxooxazolidin-5-ylmethyl]difluoroacetamide Step 1.

5(S)-Aminomethyl-3-[4-(1-cyanocyclopropan-1-yl)phenyl]oxazolidin-2-one.

The title compound 5(S)-aminomethyl-3-[4-(1-cyanocyclopropan-1-yl)phenyl]oxazolidin-2-one (5.31 g) was prepared from 5(R)-azidomethyl-3-[4-(1-cyanocyclopropan-1-yl)phenyl]oxazolidin-2-one (6.60 g) in the same manner as described for EXAMPLE 58.

MS (EI$^+$) m/z: 257 (M$^+$). HRMS (EI$^+$) for C14H15N3O2 (M$^+$): calcd, 257.1164; found, 257.1135.

Step 2.

N-[5(S)-3-[4-(1-Cyanocyclopropan-1-yl)phenyl]-2-oxooxazolidin-5-ylmethyl]difluoroacetamide.

The title compound N-[5(S)-3-[4-(1-cyanocyclopropan-1-yl)phenyl]-2-oxooxazolidin-5-ylmethyl]difluoroacetamide (695 mg) was prepared from 5(S)-aminomethyl-3-[4-(1-cyanocyclopropan-1-yl)phenyl]oxazolidin-2-one (600 mg) in the same manner as described for EXAMPLE 14.

MS (EI$^+$) m/z: 335 (M$^+$). HRMS (EI$^+$) for C16H15F2N3O3 (M$^+$): calcd, 335.1081; found, 335.1080.

EXAMPLE 62

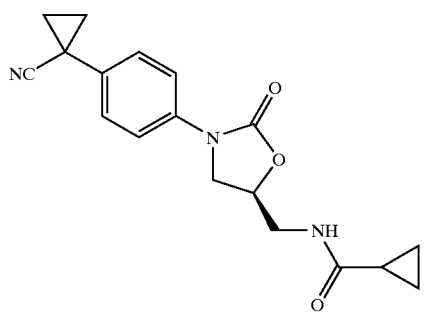

N-[5(S)-3-[4-(1-Cyanocyclopropan-1-yl)phenyl]-2-oxooxazolidin-5-ylmethyl]cyclopropanecarboxamide To a solution of 5(S)-aminomethyl-3-[4-(1-cyanocyclopropan-1-yl)phenyl]oxazolidin-2-one (150 mg) and cyclopropanecarboxylic acid (65.2 mg) in dichloromethane (10 mL) was added 1-[3-(dimethylamino)propyl]-3-ethylcarbodiimide hydrochloride (168 mg), the mixture was stirred at room temperature for 12 hours. The mixture was washed with water and saturated sodium hydrogencarbonate solution, dried over anhydrous magnesium sulfate, filtered, and then concentrated in vacuo. Flash chromatography (silica, dichloromethane:methanol=95:5) of the residue gave N-[5(S)-3-[4-(1-cyanocyclopropan-1-yl)phenyl]-2-oxooxazolidin-5-ylmethyl]cyclopropanecarboxamide (160 mg).

MS (EI$^+$) m/z: 325 (M$^+$). HRMS (EI$^+$) for C18H19N3O3 (M$^+$): calcd, 325.1426; found, 325.1426.

EXAMPLE 63

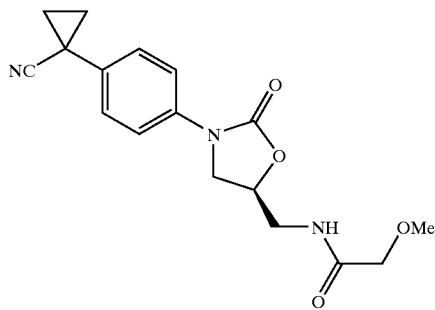

N-[5(S)-3-[4-(1-Cyanocyclopropan-1-yl)phenyl]-2-oxooxazolidin-5-ylmethyl]methoxyacetamide The title compound N-[5(S)-3-[4-(1-cyanocyclopropan-1-yl)phenyl]-2-oxooxazolidin-5-ylmethyl]methoxyacetamide (189 mg) was prepared from 5(S)-aminomethyl-3-[4-(1-cyanocyclopropan-1-yl)phenyl]oxazolidin-2-one (150 mg) and methoxyacetic acid (68.3 mg) in the same manner as described for EXAMPLE 62.

MS (EI$^+$) m/z: 329 (M$^+$). HRMS (EI$^+$) for C17H19N3O4 (M$^+$): calcd, 329.1376; found, 329.1378.

EXAMPLE 64

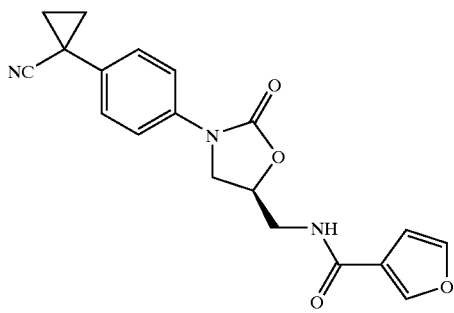

N-[5(S)-3-[4-(1-Cyanocyclopropan-1-yl)phenyl]-2-oxooxazolidin-5-ylmethyl]furan-3-carboxamide The title compound N-[5(S)-3-[4-(1-cyanocyclopropan-1-yl)phenyl]-2-oxooxazolidin-5-ylmethyl]furan-3-carboxamide (183 mg) was prepared from 5(S)-aminomethyl-3-[4-(1-cyanocyclopropan-1-yl)phenyl]oxazolidin-2-one (150 mg) and furan-3-carboxylic acid (84.9 mg) in the same manner as described for EXAMPLE 62.

MS (EI$^+$) m/z: 351 (M$^+$). HRMS (EI$^+$) for C19H17N3O4 (M$^+$): calcd, 351.1219; found, 351.1222.

EXAMPLE 65

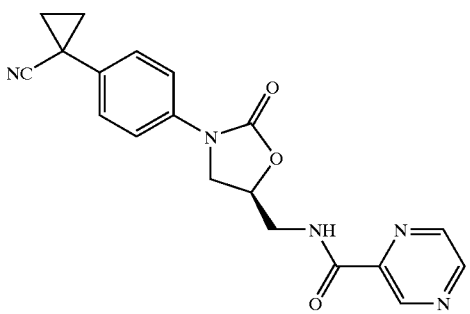

N-[5(S)-3-[4-(1-Cyanocyclopropan-1-yl)phenyl]-2-oxooxazolidin-5-ylmethyl]pyrazine-2-carboxamide The title compound N-[5(S)-3-[4-(1-cyanocyclopropan-1-yl)phenyl]-2-oxooxazolidin-5-ylmethyl]pyrazine-2-carboxamide (135 mg) was prepared from 5(S)-aminomethyl-3-[4-(1-cyanocyclopropan-1-yl)phenyl]oxazolidin-2-one (150 mg) and pyrazine-2-carboxylic acid (94.1 mg) in the same manner as described for EXAMPLE 62.

MS (EI$^+$) m/z: 363 (M$^+$). HRMS (EI$^+$) for C19H17N5O3 (M$^+$): calcd, 363.1331; found, 363.1348.

EXAMPLE 66

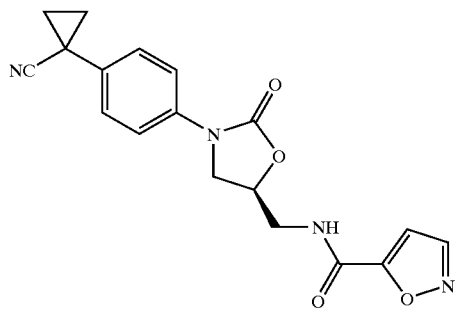

N-[5(S)-3-[4-(1-Cyanocyclopropan-1-yl)phenyl]-2-oxooxazolidin-5-ylmethyl]isoxazole-5-carboxamide The title compound N-[5(S)-3-[4-(1-cyanocyclopropan-1-yl)phenyl]-2-oxooxazolidin-5-ylmethyl]isoxazole-5-carboxamide (197 mg) was prepared from 5(S)-aminomethyl-3-[4-(1-cyanocyclopropan-1-yl)phenyl]oxazolidin-2-one (150 mg) and isoxazole-5-carboxylic acid (85.7 mg) in the same manner as described for EXAMPLE 62.

MS (EI$^+$) m/z: 352 (M$^+$). HRMS (EI$^+$) for C18H16N4O4 (M$^+$): calcd, 352.1172; found, 352.1179.

EXAMPLE 67

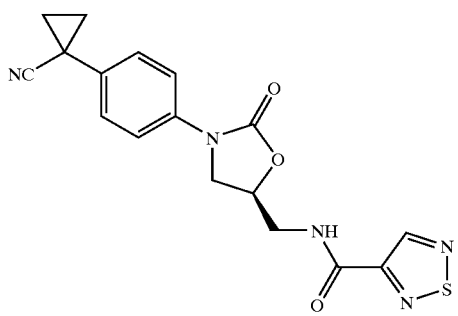

N-[5(S)-3-[4-(1-Cyanocyclopropan-1-yl)phenyl]-2-oxooxazolidin-5-ylmethyl]-1,2,5-thiadiazole-3-carboxamide The title compound N-[5(S)-3-[4-(1-cyanocyclopropan-1-yl)phenyl]-2-oxooxazolidin-5-ylmethyl]-1,2,5-thiadiazole-4-carboxamide (186 mg) was prepared from 5(S)-aminomethyl-3-[4-(1-cyanocyclopropan-1-yl)phenyl]oxazolidin-2-one (150 mg) and 1,2,5-thiadiazole-3-carboxylic acid (91.0 mg) in the same manner as described for EXAMPLE 62.

MS (EI$^+$) m/z: 369 (M$^+$). HRMS (EI$^+$) for C17H15N5O3S (M$^+$): calcd, 369.0896; found, 369.0916.

EXAMPLE 68

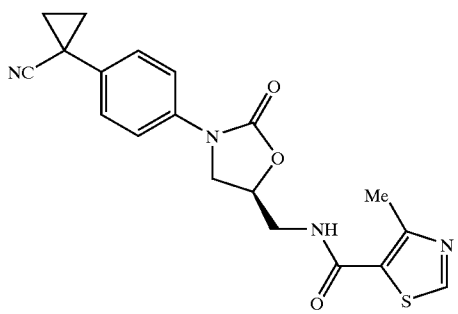

N-[5(S)-3-[4-(1-Cyanocyclopropan-1-yl)phenyl]-2-oxooxazolidin-5-ylmethyl]-(4-methyl-1,3-thiazole)-5-carboxamide The title compound N-[5(S)-3-[4-(1-cyanocyclopropan-1-yl)phenyl]-2-oxooxazolidin-5-ylmethyl]-(4-methyl-1,3-thiazole)-5-carboxamide (215 mg) was prepared from 5(S)-aminomethyl-3-[4-(1-cyanocyclopropan-1-yl)phenyl]oxazolidin-2-one (150 mg) and 4-methyl-1,3-thiadiazole-5-carboxylic acid (100 mg) in the same manner as described for EXAMPLE 62.

MS (EI$^+$) m/z: 382 (M$^+$). HRMS (EI$^+$) for C19H18N4O3S (M$^+$): calcd, 382.1100; found, 382.1121.

EXAMPLE 69

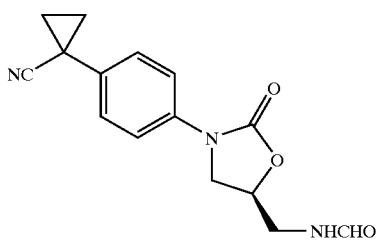

N-[5(S)-3-[4-(1-Cyanocyclopropan-1-yl)phenyl]-2-oxooxazolidin-5-ylmethyl]formamide The title compound N-[5(S)-3-[4-(1-cyanocyclopropan-1-yl)phenyl]-2-oxooxazolidin-5-ylmethyl]formamide (167 mg) was prepared from 5(S)-aminomethyl-3-[4-(1-cyanocyclopropan-1-yl)phenyl]oxazolidin-2-one (160 mg) and formic acid (34.3 mg) in the same manner as described for EXAMPLE 62.

MS (EI$^+$) m/z: 285 (M$^+$). HRMS (EI$^+$) for C15H15N3O3 (M$^+$): calcd, 285.1113; found, 285.1104.

EXAMPLE 70

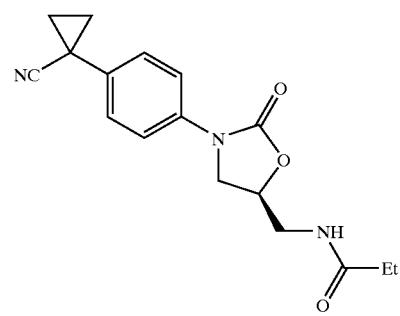

N-[5(S)-3-[4-(1-Cyanocyclopropan-1-yl)phenyl]-2-oxooxazolidin-5-ylmethyl]propionamide The title compound N-[5(S)-3-[4-(1-cyanocyclopropan-1-yl)phenyl]-2-oxooxazolidin-5-ylmethyl]propionamide (184 mg) was prepared from 5(S)-aminomethyl-3-[4-(1-cyanocyclopropan-1-yl)phenyl]oxazolidin-2-one (160 mg) and propionic anhydride (162 mg) in the same manner as described for EXAMPLE 14.

MS (EI$^+$) m/z: 313 (M$^+$). HRMS (EI$^+$) for C17H19N3O3 (M$^+$): calcd, 313.1426; found, 313.1429.

EXAMPLE 71

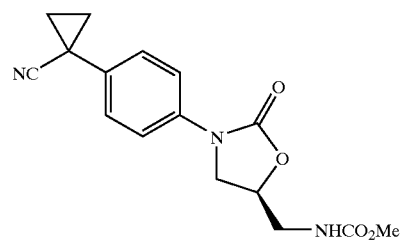

5(S)-3-[4-(1-Cyanocyclopropan-1-yl)phenyl]-5-[N-(methoxycarbonyl)]aminomethyloxazolidin-2-one The title compound 5(S)-3-[4-(1-cyanocyclopropan-1-yl)phenyl]-5-[N-(methoxycarbonyl)]aminomethyloxazolidin-2-one (181 mg) was prepared from 5(S)-aminomethyl-3-[4-(1-cyanocyclopropan-1-yl)phenyl]oxazolidin-2-one (160 mg) and methyl chloroformate (118 mg) in the same manner as described for EXAMPLE 14.

MS (EI$^+$) m/z: 315 (M$^+$). HRMS (EI$^+$) for C16H17N3O4 (M$^+$): calcd, 315.1219; found, 315.1220.

EXAMPLE 72

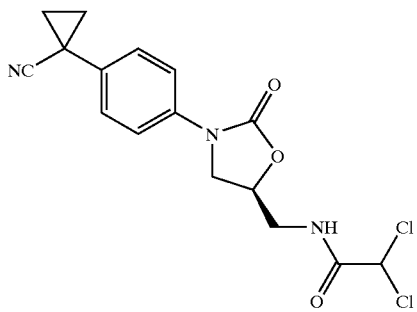

N-[5(S)-3-[4-(1-Cyanocyclopropan-1-yl)phenyl]-2-oxooxazolidin-5-ylmethyl]dichloroacetamide The title compound N-[5(S)-3-[4-(1-cyanocyclopropan-1-yl)phenyl]-2-oxooxazolidin-5-ylmethyl]dichloroacetamide (172 mg) was prepared from 5(S)-aminomethyl-3-[4-(1-cyanocyclopropan-1-yl)phenyl]oxazolidin-2-one (150 mg) and dichloroacetyl chloride (103 mg) in the same manner as described for EXAMPLE 14.

MS (EI$^+$) m/z: 367 (M$^+$). HRMS (EI$^+$) for C16H15Cl2N3O3 (M$^+$): calcd, 367.0490; found, 367.0481.

EXAMPLE 73

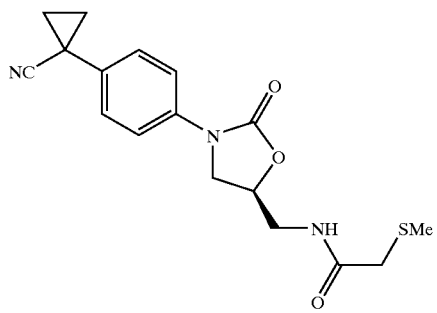

N-[5(S)-3-[4-(1-Cyanocyclopropan-1-yl)phenyl]-2-oxooxazolidin-5-ylmethyl]methylthioacetamide The title compound N-[5(S)-3-[4-(1-cyanocyclopropan-1-yl)phenyl]-2-oxooxazolidin-5-ylmethyl]methylthioacetamide (348 mg) was prepared from 5(S)-aminomethyl-3-[4-(1-cyanocyclopropan-1-yl)phenyl]oxazolidin-2-one (300 mg) and methylthioacetic acid (149 mg) in the same manner as described for EXAMPLE 62.

MS (EI$^+$) m/z: 345 (M$^+$). HRMS (EI$^+$) for C17H19N3O3S (M$^+$): calcd, 345.1147; found, 345.1156.

EXAMPLE 74

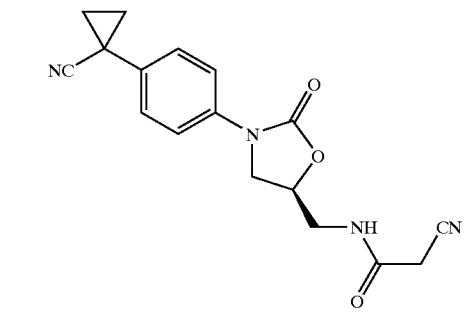

N-[5(S)-3-[4-(1-Cyanocyclopropan-1-yl)phenyl]-2-oxooxazolidin-5-ylmethyl]cyanoacetamide The title compound N-[5(S)-3-[4-(1-cyanocyclopropan-1-yl)phenyl]-2-oxooxazolidin-5-ylmethyl]cyanoacetamide (179 mg) was prepared from 5(S)-aminomethyl-3-[4-(1-cyanocyclopropan-1-yl)phenyl]oxazolidin-2-one (150 mg) and cyanoacetic acid (64.5 mg) in the same manner as described for EXAMPLE 62.

MS (EI$^+$) m/z: 324 (M$^+$). HRMS (EI$^+$) for C17H16N4O3 (M$^+$): calcd, 324.1222; found, 324.1245.

EXAMPLE 75

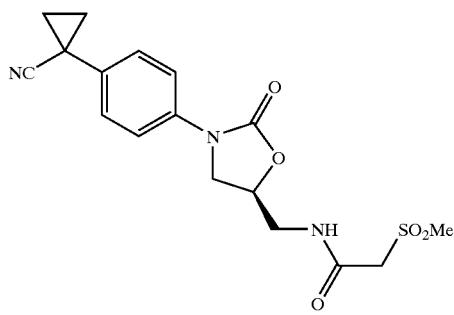

N-[5(S)-3-[4-(1-Cyanocyclopropan-1-yl)phenyl]-2-oxooxazolidin-5-ylmethyl]methylsulfonylacetamide The title compound N-[5(S)-3-[4-(1-cyanocyclopropan-1-yl)phenyl]-2-oxooxazolidin-5-ylmethyl]methylsulfonylacetamide (199 mg) was prepared from 5(S)-aminomethyl-3-[4-(1-cyanocyclopropan-1-yl)phenyl]oxazolidin-2-one (150 mg) and methylsulfonylacetic acid (105 mg) in the same manner as described for EXAMPLE 62.

MS (EI$^+$) m/z: 377 (M$^+$). HRMS (EI$^+$) for C17H19N3O5S (M$^+$): calcd, 377.1045; found, 377.1035.

EXAMPLE 76

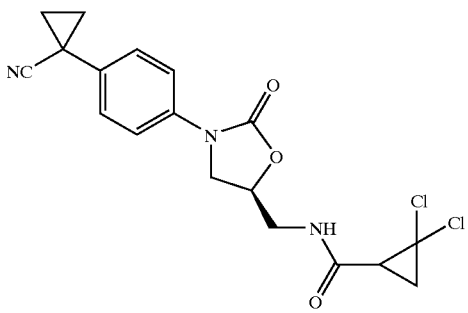

N-[5(S)-3-[4-(1-Cyanocyclopropan-1-yl)phenyl]-2-oxooxazolidin-5-ylmethyl]-(2,2-dichloro)cyclopropane-1-carboxamide (Diastereomers A and B)

The title compounds N-[5(S)-3-[4-(1-cyanocyclopropan-1-yl)phenyl]-2-oxooxazolidin-5-ylmethyl]-(2,2-dichloro)cyclopropane-1-carboxamide (diastereomers A (98.7 mg) and B (101 mg)) were prepared from 5(S)-aminomethyl-3-[4-(1-cyanocyclopropan-1-yl)phenyl]oxazolidin-2-one (150 mg) and 2,2-dichlorocyclopropane-1-carboxylic acid (117 mg) in the same manner as described for EXAMPLE 62.

Diastereomer A:

MS (EI$^+$) m/z: 393 (M$^+$). HRMS (EI$^+$) for C18H17Cl2N3O3 (M$^+$): calcd, 393.0647; found, 393.0666.

Diastereomer B:

MS (EI$^+$) m/z: 393 (M$^+$). HRMS (EI$^+$) for C18H17Cl2N3O3 (M$^+$): calcd, 393.0647; found, 393.0677.

EXAMPLE 77

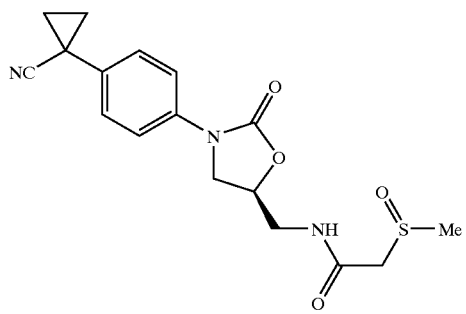

N-[5(S)-3-[4-(1-Cyanocyclopropan-1-yl)phenyl]-2-oxooxazolidin-5-ylmethyl]methylsulfinylacetamide To a solution of N-[5(S)-3-[4-(1-cyanocyclopropan-1-yl)phenyl]-2-oxooxazolidin-5-ylmethyl]methylthioacetamide (160 mg) in dichloromethane (4 mL) was added m-chloroperbenzoic acid (87.9 mg) at 0° C., the mixture was stirred at the same temperature for 2 hours. The mixture was washed with 5% sodium bisulfate solution, 5% sodium hydrogencarbonate solution and brine, dried over anhydrous magnesium sulfate, filtered, and then concentrated in vacuo. Flash chromatography (silica, dichloromethane:methanol=9:1) of the residue gave N-[5(S)-3-[4-(1-cyanocyclopropan-1-yl)phenyl]-2-oxooxazolidin-5-ylmethyl]methylsulfinylacetamide (139 mg).

MS (FAB$^+$) m/z: 362 (MH$^+$). HRMS (FAB$^+$) for C17H20N3O4S (MH$^+$): calcd, 362.1175; found, 362.1163.

EXAMPLE 78

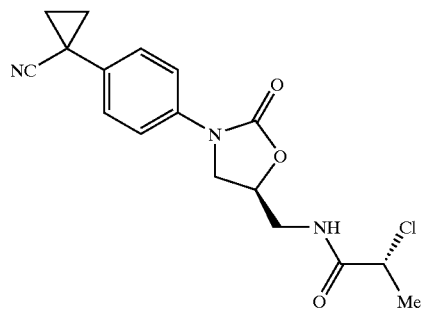

N-[5(S)-3-[4-(1-Cyanocyclopropan-1-yl)phenyl]-2-oxooxazolidin-5-ylmethyl]-2(R)-chloropropionamide The title compound N-[5(S)-3-[4-(1-cyanocyclopropan-1-yl)phenyl]-2-oxooxazolidin-5-ylmethyl]-2(R)-chloropropionamide (194 mg) was prepared from 5(S)-aminomethyl-3-[4-(1-cyanocyclopropan-1-yl)phenyl]oxazolidin-2-one (150 mg) and (R)-chloropropionic acid (82.2 mg) in the same manner as described for EXAMPLE 62.

MS (EI$^+$) m/z: 347 (M$^+$). HRMS (EI$^+$) for C17H18ClN3O3 (M$^+$): calcd, 347.1037; found, 347.1038.

EXAMPLE 79

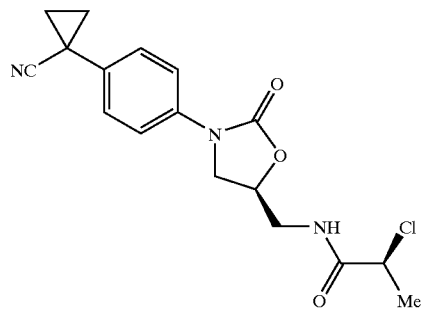

N-[5(S)-3-[4-(1-Cyanocyclopropan-1-yl)phenyl]-2-oxooxazolidin-5-ylmethyl]-2(S)-chloropropionamide The title compound N-[5(S)-3-[4-(1-cyanocyclopropan-1-yl)phenyl]-2-oxooxazolidin-5-ylmethyl]-2(S)-chloropropionamide (193 mg) was prepared from 5(S)-aminomethyl-3-[4-(1-cyanocyclopropan-1-yl)phenyl]oxazolidin-2-one (150 mg) and (S)-chloropropionic acid (82.2 mg) in the same manner as described for EXAMPLE 62.

MS (EI$^+$) m/z: 347 (M$^+$). HRMS (EI$^+$) for C17H18ClN3O3 (M$^+$): calcd, 347.1037; found, 347.1063.

EXAMPLE 80

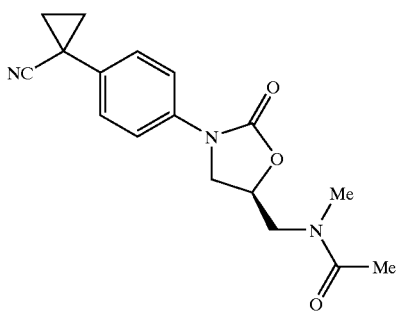

N-[5(S)-3-[4-(1-Cyanocyclopropan-1-yl)phenyl]-2-oxooxazolidin-5-ylmethyl]-N-methylacetamide To a solution of N-[5(S)-3-[4-(1-cyanocyclopropan-1-yl)phenyl]-2-oxooxazolidin-5-ylmethyl]acetamide (140 mg) in tetrahydrofuran (5 mL) was added iodomethane (73 μL) and potassium t-butoxide (78.7 mg) at room temperature, the mixture was stirred at the same temperature for 1 hour. After quenching the reaction by addition of 5% hydrochloric acid, the mixture was extracted with ethyl acetate. The organic extracts to were washed with 5% sodium hydrogencarbonate solution, 5% sodium thiosulfate solution and brine, dried over anhydrous magnesium sulfate, filtered, and then concentrated in vacuo. Flash chromatography (silica, ethyl acetate:methanol=19:1) of the residue gave N-[5(S)-3-[4-(1-cyanocyclopropan-1-yl)phenyl]-2-oxooxazolidin-5-ylmethyl]-N-methylacetamide (139 mg).

MS (EI$^+$) m/z: 313 (M$^+$). HRMS (EI$^+$) for C17H19N3O3 (M$^+$): calcd, 313.1426; found, 313.1433.

EXAMPLE 81

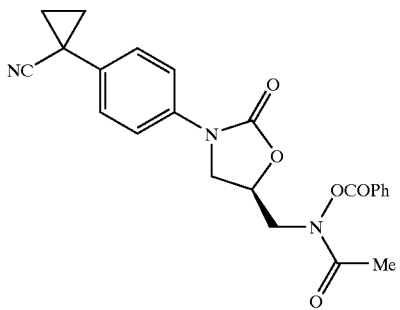

N-Benzoyloxy-N-[5(S)-3-[4-(1-cyanocyclopropan-1-yl)phenyl]-2-oxooxazolidin-5-ylmethyl]acetamide and N-Benzoyloxy-O-[5(S)-3-[4-(1-cyanocyclopropan-1-yl)phenyl]-2-oxooxazolidin-5-ylmethyl]acetimidate The title compounds N-benzoyloxy-N-[5(S)-3-[4-(1-cyanocyclopropan-1-yl)phenyl]-2-oxooxazolidin-5-ylmethyl]acetamide (127 mg) and N-benzoyloxy-O-[5(S)-3-[4-(1-cyanocyclopropan-1-yl)phenyl]-2-oxooxazolidin-5-ylmethyl]acetimidate (268 mg) were prepared from 5(R)-3-[4-(1-cyanocyclopropan-1-yl)phenyl]-5-hydroxymethyloxazolidin-2-one (272 mg) and N-benzoyloxyacetamide (179 mg) in the same manner as described for EXAMPLE 25.

N-Benzoyloxy-N-[5(S)-3-[4-(1-cyanocyclopropan-1-yl)phenyl]-2-oxooxazolidin-5-ylmethyl]acetamide:

MS (EI$^+$) m/z: 419 (M$^+$). HRMS (EI$^+$) for C23H21N3O5 (M$^+$): calcd, 419.1481; found, 419.1505.

N-Benzoyloxy-O-[5(S)-3-[4-(1-cyanocyclopropan-1-yl)phenyl]-2-oxooxazolidin-5-ylmethyl]acetimidate:

MS (FAB$^+$) m/z: 420 (MH$^+$). HRMS (FAB$^+$) for C23H22N3O5 (MH$^+$): calcd, 420.1559; found, 420.1578.

EXAMPLE 82

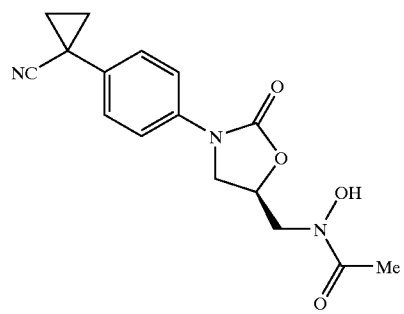

N-[5(S)-3-[4-(1-Cyanocyclopropan-1-yl)phenyl]-2-oxooxazolidin-5-ylmethyl]-N-hydroxyacetamide To a solution of N-benzoyloxy-N-[5(S)-3-[4-(1-cyanocyclopropan-1-yl)phenyl]-2-oxooxazolidin-5-ylmethyl]acetamide (105 mg) in methanol (10 mL) was added potassium carbonate (34.6 mg), the mixture was sonicated at room temperature for 5 min, and then concentrated in vacuo. Flash chromatography (silica, dichloromethane:methanol=9:1) of the residue gave N-[5(S)-3-[4-(1-cyanocyclopropan-1-yl)phenyl]-2-oxooxazolidin-5-ylmethyl]-N-hydroxyacetamide (57.2 mg).

MS (EI$^+$) m/z: 315 (M$^+$). HRMS (EI$^+$) for C16H17N3O4 (M$^+$): calcd, 315.1219; found, 315.1229.

EXAMPLE 83

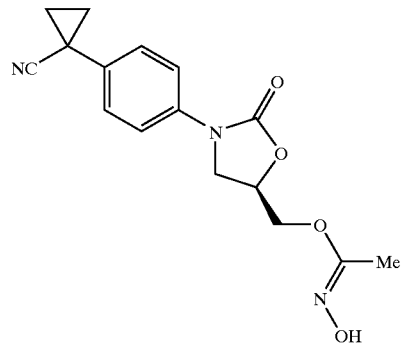

O-[5(S)-3-[4-(1-Cyanocyclopropan-1-yl)phenyl]-2-oxooxazolidin-5-ylmethyl]-N-hydroxyacetimidate The title compound O-[5(S)-3-[4-(1-cyanocyclopropan-1-yl)phenyl]-2-oxooxazolidin-5-ylmethyl]-N- hydroxyacetimidate (110 mg) was prepared from N-benzoyloxy-O-[5(S)-3-[4-(1-cyanocyclopropan-1-yl)phenyl]-2-oxooxazolidin-5-ylmethyl]acetimidate (235 mg) in the same manner as described for EXAMPLE 82.

MS (EI$^+$) m/z: 315 (M$^+$). HRMS (EI$^+$) for C16H17N3O4 (M$^+$): calcd, 315.1219; found, 315.1247.

EXAMPLE 84

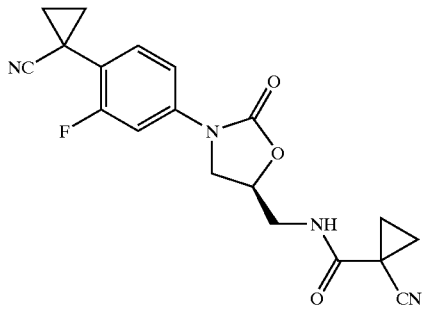

N-[5(S)-3-[4-(1-Cyanocyclopropan-1-yl)-3-fluorophenyl]-2-oxooxazolidin-5-ylmethyl]-1-cyanocyclopropane-1-carboxamide To a solution of 5(S)-aminomethyl-3-[4-(1-cyanocyclopropan-1-yl)-3-fluorophenyl]oxazolidin-2-one (315 mg) and 1-cyanocyclopropane-1-carboxylic acid (131 mg) in dimethylformamide (4 mL) was added diethyl cyanophosphonate (0.21 mL) and triethylamine (0.18 mL) at 0° C., the mixture was stirred at room temperature for 18 hours. After dilution with 1 N hydrochloric acid, the mixture was extracted with ethyl acetate. The organic extracts were washed with water, 1 N sodium hydroxide solution and brine, dried over anhydrous sodium sulfate, filtered, and then concentrated in vacuo. Flash chromatography (silica, hexane:ethyl acetate=3:10) of the residue gave N-[5(S)-3-[4-(1-cyanocyclopropan-1-yl)-3-fluorophenyl]-2-oxooxazolidin-5-ylmethyl]-1-cyanocyclopropane-1-carboxamide (306 mg).

MS (EI$^+$) m/z: 368 (M$^+$). HRMS (EI$^+$) for C19H17FN4O3 (M$^+$): calcd, 368.1285; found, 368.1260.

EXAMPLE 85

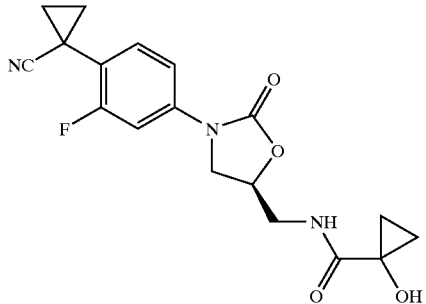

N-[5(S)-3-[4-(1-Cyanocyclopropan-1-yl)-3-fluorophenyl]-2-oxooxazolidin-5-ylmethyl]-1-hydroxycyclopropane-1-carboxamide The title compound N-[5(S)-3-[4-(1-cyanocyclopropan-1-yl)-3-fluorophenyl]-2-oxooxazolidin-5-ylmethyl]-1-hydroxycyclopropane-1-carboxamide (364 mg) was prepared from 5(S)-aminomethyl-3-[4-(1-cyanocyclopropan-1-yl)-3-fluorophenyl]oxazolidin-2-one (426 mg) and 1-hydroxycyclopropane-1-carboxylic acid (163 mg) in the same manner as described for EXAMPLE 84.

MS (EI$^+$) m/z: 359 (M$^+$). HRMS (EI$^+$) for C18H18FN3O4 (M$^+$): calcd, 359.1281; found, 359.1305.

EXAMPLE 86

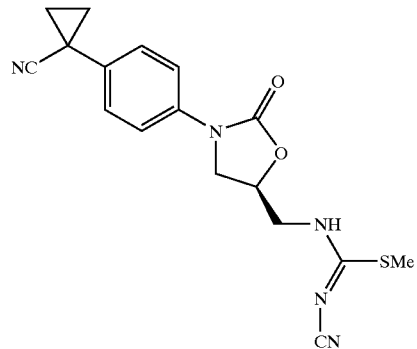

N'-Cyano-N-[5(S)-3-[4-(1-cyanocyclopropan-1-yl)phenyl]-2-oxooxazolidin-5-ylmethyl]-S-methylisothiourea To a solution of dimethyl N-cyanodithioiminocarbonate (179 mg) in methanol (2 mL) was added a solution of 5(S)-aminomethyl-3-[4-(1-cyanocyclopropan-1-yl)phenyl]oxazolidin-2-one (257 mg) in methanol (6 mL), the mixture was stirred at room temperature for 7 hours. The resulting precipitates were collected by filtration and washed with cold methanol to give N'-cyano-N-[5(S)-3-[4-(1-cyanocyclopropan-1-yl)phenyl]-2-oxooxazolidin-5-ylmethyl]-S-methylisothiourea (281 mg).

MS (FAB$^+$) m/z: 356 (MH$^+$). HRMS (FAB$^+$) for C17H18N5O2S (MH$^+$): calcd, 356.1181; found, 356.1172.

EXAMPLE 87

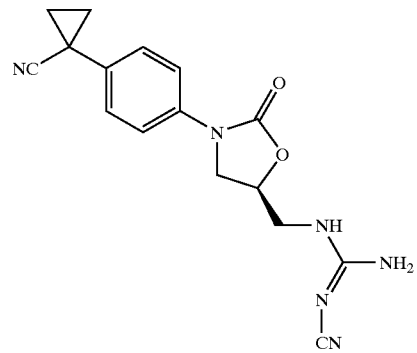

N'-Cyano-N-[5(S)-3-[4-(1-cyanocyclopropan-1-yl)phenyl]-2-oxooxazolidin-5-ylmethyl]urea To a solution of N'-cyano-N-[5(S)-3-[4-(1-cyanocyclopropan-1-yl)phenyl]-2-oxooxazolidin-5-ylmethyl]-S-methylisothiourea (210 mg) in pyridine (4 mL) was added a solution of ammonia (7 N, 20 mL) in methanol, the mixture was allowed to stand at room temperature overnight, and then concentrated in vacuo. Treatment of the residue with cold methanol gave N'-cyano-N-[5(S)-3-[4-(1- cyanocyclopropan-1-yl)phenyl]-2-oxooxazolidin-5-ylmethyl]urea (166 mg).

MS (FAB+) m/z: 325 (MH+). HRMS (FAB+) for C16H17N6O2 (MH+): calcd, 325.1413; found, 325.1414.

EXAMPLE 88

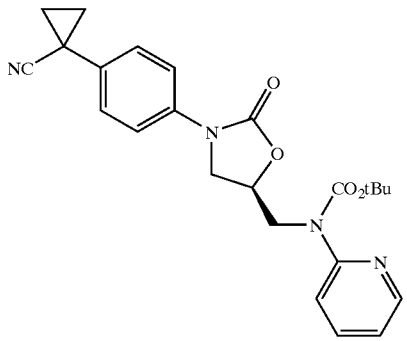

5(S)-5-[N-(t-Butoxycarbonyl)-N-(pyridin-2-yl)]aminomethyl-3-[4-(1-cyanocyclopropan-1-yl)phenyl]oxazolidin-2-one The title compound 5(S)-5-[N-(t-Butoxycarbonyl)-N-(pyridin-2-yl)]aminomethyl-3-[4-(1-cyanocyclopropan-1-yl)phenyl]oxazolidin-2-one (307 mg) was prepared from 5(R)-3-[4-(1-cyanocyclopropan-1-yl)phenyl]-5-hydroxymethyloxazolidin-2-one (258 mg) and 2-(t-butoxycarbonyl)aminopyridine (389 mg) in the same manner as described for EXAMPLE 15.

MS (EI+) m/z: 434 (M+). HRMS (EI+) for C24H26N4O4 (M+): calcd, 434.1954; found, 434.1973.

EXAMPLE 89

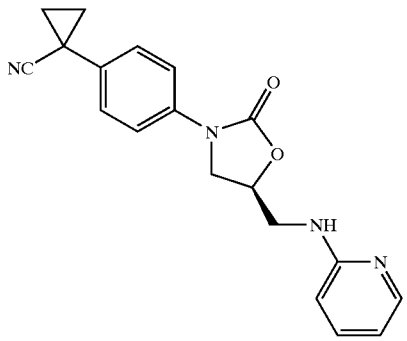

5(S)-3-[4-(1-Cyanocyclopropan-1-yl)phenyl]-5-[N-(pyridin-2-yl)]aminomethyloxazolidin-2-one The title compound 5(S)-3-[4-(1-cyanocyclopropan-1-yl)phenyl]-5-[N-(pyridin-2-yl)]aminomethyloxazolidin-2-one (175 mg) was prepared from 5(S)-5-[N-(t-butoxycarbonyl)-N-(pyridin-2-yl)]aminomethyl-3-[4-(1-cyanocyclopropan-1-yl)phenyl]oxazolidin-2-one (335 mg) using a solution of hydrogen chloride (8 M, 5 mL) in methanol instead of trifluoroacetic acid in the same manner as described for EXAMPLE 17.

MS (FAB+) m/z: 335 (MH+). HRMS (FAB+) for C19H19N4O2 (MH+): calcd, 335.1508; found, 335.1516.

EXAMPLE 90

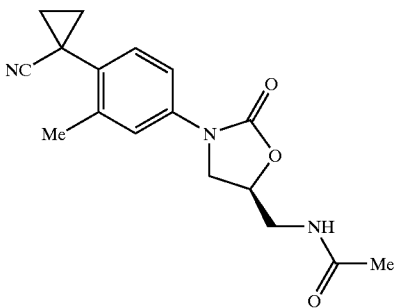

N-[5(S)-3-[4-(1-Cyanocyclopropan-1-yl)-3-methylphenyl]-2-oxooxazolidin-5-ylmethyl]acetamide Step 1.

5(R)-3-[4-(1-Cyanocyclopropan-1-yl)-3-methylphenyl]-5-hydroxymethyloxazolidin-2-one.

The title compound 5(R)-3-[4-(1-cyanocyclopropan-1-yl)-3-methylphenyl]-5-hydroxymethyloxazolidin-2-one (1.34 g) was prepared from 1-(4-benzyloxycarbonylamino-2-methylphenyl)-1-cyclopropanecarbonitrile (2.48 g) in the same manner as described for EXAMPLE 1.

MS (EI+) m/z: 272 (M+). HRMS (EI+) for C15H16N2O3 (M+): calcd, 272.1161; found, 272.1169.

Step 2.

5(R)-Azidomethyl-3-[4-(1-cyanocyclopropan-1-yl)-3-methylphenyl]oxazolidin-2-one.

The title compound 5(R)-azidomethyl-3-[4-(1-cyanocyclopropan-1-yl)-3-methylphenyl]oxazolidin-2-one (1.04 g) was prepared from 5(R)-3-[4-(1-cyanocyclopropan-1-yl)-3-methylphenyl]-5-hydroxymethyloxazolidin-2-one (1.00 g) in the same manner as described for EXAMPLE 1.

MS (EI+) m/z: 297 (M+). HRMS (EI+) for C15H15N5O2 (M+): calcd, 297.1226; found, 297.1227.

Step 3.

5(S)-Aminomethyl-3-[4-(1-cyanocyclopropan-1-yl)-3-methylphenyl]oxazolidin-2-one.

The title compound 5(S)-aminomethyl-3-[4-(1-cyanocyclopropan-1-yl)-3-methylphenyl]oxazolidin-2-one (706 mg) was prepared from 5(R)-azidomethyl-3-[4-(1-cyanocyclopropan-1-yl)-3-methylphenyl]oxazolidin-2-one (805 mg) in the same manner as described for EXAMPLE 9.

Rf: 0.19 (silica, dichloromethane:methanol=4:1).

Step 4.

N-[5(S)-3-[4-(1-Cyanocyclopropan-1-yl)-3-methylphenyl]-2-oxooxazolidin-5-ylmethyl]acetamide.

The title compound N-[5(S)-3-[4-(1-cyanocyclopropan-1-yl)-3-methylphenyl]-2-oxooxazolidin-5-ylmethyl]acetamide (134 mg) was prepared from 5(S)-aminomethyl-3-[4-(1-cyanocyclopropan-1-yl)-3-methylphenyl]oxazolidin-2-one (120 mg) in the same manner as described for EXAMPLE 14.

MS (EI+) m/z: 313 (M+). HRMS (EI+) for C17H19N3O3 (M+): calcd, 313.1426; found, 313.1423.

EXAMPLE 91

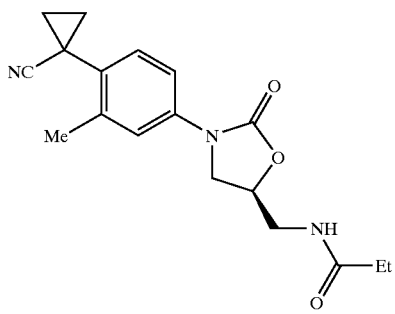

N-[5(S)-3-[4-(1-Cyanocyclopropan-1-yl)]-3-methylphenyl]-2-oxooxazolidin-5-ylmethyl] propionamide The title compound N-[5(S)-3-[4-(1-cyanocyclopropan-1-yl)]-3-methylphenyl]-2-oxooxazolidin-5-ylmethyl] propionamide (139 mg) was prepared from 5(S)-aminomethyl-3-[4-(1-cyanocyclopropan-1-yl)]-3-methylphenyl]oxazolidin-2-one (120 mg) and propionic anhydride (115 mg) in the same manner as described for EXAMPLE 14.

MS (EI$^+$) m/z: 327 (M$^+$). HRMS (EI$^+$) for C18H21N3O3 (M$^+$): calcd, 327.1583; found, 327.1571.

EXAMPLE 92

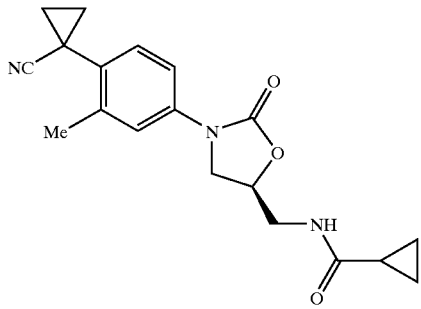

N-[5(S)-3-[4-(1-Cyanocyclopropan-1-yl)-3-methylphenyl]-2-oxooxazolidin-5-ylmethyl] cyclopropanecarboxamide The title compound N-[5(S)-3-[4-(1-cyanocyclopropan-1-yl)-3-methylphenyl]-2-oxooxazolidin-5-ylmethyl] cyclopropanecarboxamide (138 mg) was prepared from 5(S)-aminomethyl-3-[4-(1-cyanocyclopropan-1-yl)-3-methylphenyl]oxazolidin-2-one (120 mg) in the same manner as described for EXAMPLE 62.

MS (EI$^+$) m/z: 339 (M$^+$). HRMS (EI$^+$) for C19H21N3O3 (M$^+$): calcd, 339.1583; found, 339.1580.

EXAMPLE 93

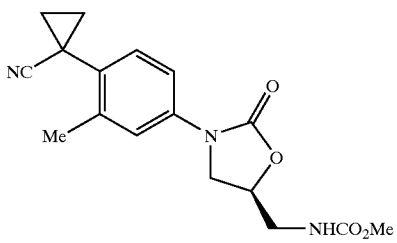

5(S)-3-[4-(1-Cyanocyclopropan-1-yl)-3-methylphenyl]-5-[N-(methoxycarbonyl)] aminomethyloxazolidin-2-one The title compound 5(S)-3-[4-(1-cyanocyclopropan-1-yl)-3-methylphenyl]-5-[N-(methoxycarbonyl)] aminomethyloxazolidin-2-one (142 mg) was prepared from 5(S)-aminomethyl-3-[4-(1-cyanocyclopropan-1-yl)-3-methylphenyl]oxazolidin-2-one (120 mg) and methyl chloroformate (51 μL) in the same manner as described for EXAMPLE 14.

MS (EI$^+$) m/z: 329 (M$^+$). HRMS (EI$^+$) for C17H19N3O4 (M$^+$): calcd, 329.1376; found, 329.1391.

EXAMPLE 94

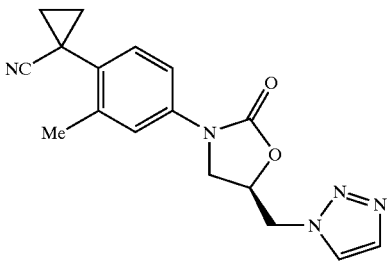

1-[5(R)-3-[4-(1-Cyanocyclopropan-1-yl)-3-methylphenyl]-2-oxooxazolidin-5-ylmethyl]-1,2,3-triazole The title compound 1-[5(R)-3-[4-(1-Cyanocyclopropan-1-yl)-3-methylphenyl]-2-oxooxazolidin-5-ylmethyl]-1,2,3-triazole (187 mg) was prepared from 5(R)-azidomethyl-3-[4-(1-cyanocyclopropan-1-yl)-3-methylphenyl]oxazolidin-2-one (200 mg) in the same manner as described for EXAMPLE 37.

MS (EI$^+$) m/z: 323 (M$^+$). HRMS (EI$^+$) for C17H17N5O2 (M$^+$): calcd, 323.1382; found, 323.1369.

EXAMPLE 95

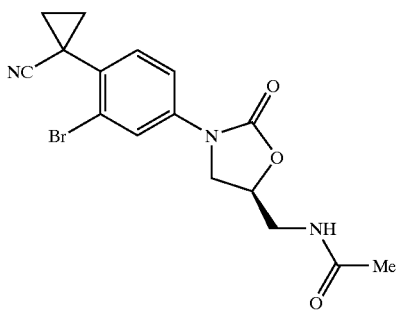

N-[5(S)-3-[3-Bromo-4-(1-Cyanocyclopropan-1-yl)
phenyl]-2-oxooxazolidin-5-ylmethyl]acetamide Step 1.

5(R)-3-[3-Bromo-4-(1-Cyanocyclopropan-1-yl)phenyl]-5-hydroxymethyloxazolidin-2-one.

The title compound 5(R)-3-[3-bromo-4-(1-cyanocyclopropan-1-yl)phenyl]-5-hydroxymethyloxazolidin-2-one (658 mg) was prepared from 1-(4-benzyloxycarbonylamino-2-bromophenyl)-1-cyclopropanecarbonitrile (1.15 g) using lithium t-butoxide (prepared from t-butanol (298 mg) and n-butyllithium in hexane (2.66 M, 1.3 mL)) in stead of n-butyllithium in the same manner as described for EXAMPLE 1.

MS (EI$^+$) m/z: 336 (M$^+$). HRMS (EI$^+$) for C14H13BrN2O3 (M$^+$): calcd, 336.0110; found, 336.0111.

Step 2.

5(R)-Azidomethyl-3-[3-bromo-4-(1-cyanocyclopropan-1-yl)phenyl]oxazolidin-2-one.

The title compound 5(R)-azidomethyl-3-[3-bromo-4-(1-cyanocyclopropan-1-yl)phenyl]oxazolidin-2-one was prepared from 5(R)-3-[3-bromo-4-(1-cyanocyclopropan-1-yl)phenyl]-5-hydroxymethyloxazolidin-2-one (580 mg) in the same manner as described for EXAMPLE 1. This was used in the next step without further purification.

Rf: 0.50 (silica, hexane:ethyl acetate=1:2).

Step 3.

N-[5(S)-3-[3-Bromo-4-(1-Cyanocyclopropan-1-yl)phenyl]-2-oxooxazolidin-5-ylmethyl]acetamide.

To a solution of the above crude 5(R)-azidomethyl-3-[3-bromo-4-(1-cyanocyclopropan-1-yl)phenyl]oxazolidin-2-one in tetrahydrofuran (10 mL) was added triphenylphosphine (541 mg), the mixture was stirred at room temperature for 6 hours. The resulting mixture was added water (155 μL) and then heated at 60° C. for 6 hours. The mixture was adjusted to pH 4 by the addition of 6 N hydrochloric acid at 0° C., diluted with ethyl acetate, and extracted with 5% hydrochloric acid. The aqueous extracts were washed with ethyl acetate, adjusted to pH 9 by the addition of potassium carbonate, and then diluted with tetrahydrofuran (20 mL). The resulting mixture was added acetic anhydride (878 mg), the mixture was stirred at room temperature for 1 hour. The mixture was extracted with ethyl acetate. The organic extracts were washed with brine, dried over anhydrous magnesium sulfate, filtered, and then concentrated in vacuo. Flash chromatography (silica, ethyl acetate:methanol=20:1) of the residue gave N-[5(S)-3-[3-bromo-4-(1-cyanocyclopropan-1-yl)phenyl]-2-oxooxazolidin-5-ylmethyl]acetamide (614 mg).

MS (EI$^+$) m/z: 377 (M$^+$). HRMS (EI$^+$) for C16H16BrN3O3 (M$^+$): calcd, 377.0375; found, 313.0378.

EXAMPLE 96

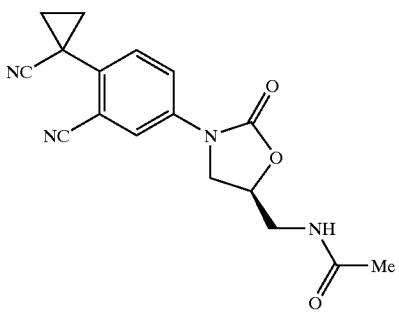

N-[5(S)-3-[3-Cyano-4-(1-cyanocyclopropan-1-yl)
phenyl]-2-oxooxazolidin-5-ylmethyl]acetamide A mixture of N-[5(S)-3-[3-bromo-4-(1-cyanocyclopropan-1-yl)phenyl]-2-oxooxazolidin-5-ylmethyl]acetamide (100 mg), zinc cyanide (24.8 mg), tris(dibenzylideneacetone)dipalladium(0) (12.1 mg) and (diphenylphosphino)ferrocene (17.6 mg) in N-methylpyrrolidone (5 mL) was heated at 150° C. for 18 hours, and then concentrated in vacuo. Flash chromatography (silica, ethyl acetate:methanol=19:1) of the residue gave N-[5(S)-3-[3-cyano-4-(1-cyanocyclopropan-1-yl)phenyl]-2-oxooxazolidin-5-ylmethyl]acetamide (43 mg).

MS (EI$^+$) m/z: 324 (M$^+$). HRMS (EI$^+$) for C17H16N4O3 (M$^+$): calcd, 324.1222; found, 324.1247.

EXAMPLE 97

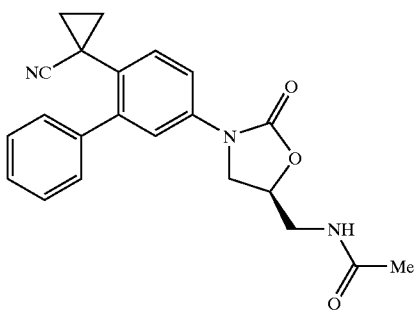

N-[5(S)-3-[4-(1-Cyanocyclopropan-1-yl)-3-phenylphenyl]-2-oxooxazolidin-5-ylmethyl]
acetamide A mixture of N-[5(S)-3-[3-bromo-4-(1-cyanocyclopropan-1-yl)phenyl]-2-oxooxazolidin-5-ylmethyl]acetamide (90 mg), phenylboronic acid (58.0 mg), tetrakis(triphenylphosphine)palladium(0) (27.5 mg), and 2 M sodium carbonate solution (240 μL) in dioxane (5 mL) was heated at 110° C. for 12 hours, and then concentrated in vacuo. Flash chromatography (silica, ethyl acetate:methanol=20:1) of the residue gave N-[5(S)-3-[4-(1-cyanocyclopropan-1-yl)-3-phenylphenyl]-2-oxooxazolidin-5-ylmethyl]acetamide (81.4 mg).

MS (EI$^+$) m/z: 375 (M$^+$). HRMS (EI$^+$) for C22H21N3O3 (M$^+$): calcd, 375.1583; found, 375.1574.

EXAMPLE 98

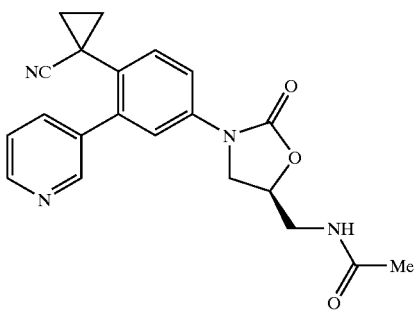

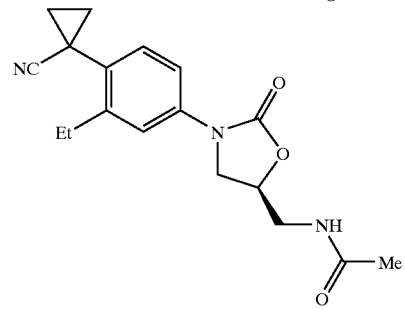

N-[5(S)-3-[4-(1-Cyanocyclopropan-1-yl)-3-(pyridin-3-yl)phenyl]-2-oxooxazolidin-5-ylmethyl]acetamide and N-[5(S)-3-[4-(1-Cyanocyclopropan-1-yl)-3-ethylphenyl]-2-oxooxazolidin-5-ylmethyl]acetamide The title compounds N-[5(S)-3-[4-(1-Cyanocyclopropan-1-yl)-3-(pyridin-3-yl)phenyl]-2-oxooxazolidin-5-ylmethyl] acetamide (36.2 mg) and N-[5(S)-3-[4-(1-cyanocyclopropan-1-yl)-3-ethylphenyl]-2-oxooxazolidin-5-ylmethyl]acetamide (24 mg) were prepared from N-[5(S)-3-[4-(1-cyanocyclopropan-1-yl)-3-bromophenyl]-2-oxooxazolidin-5-ylmethyl]acetamide (150 mg) and diethyl (3-pyridyl)borane (87.5 mg) in the same manner as described for EXAMPLE 97.

N-[5(S)-3-[4-(1-Cyanocyclopropan-1-yl)-3-(pyridin-3-yl)phenyl]-2-oxooxazolidin-5-ylmethyl]acetamide:

MS (EI$^+$) m/z: 376 (M$^+$). HRMS (EI$^+$) for C21H20N4O3 (M$^+$): calcd, 376.1535; found, 376.1524.

N-[5(S)-3-[4-(1-Cyanocyclopropan-1-yl)-3-ethylphenyl]-2-oxooxazolidin-5-ylmethyl]acetamide:

MS (EI$^+$) m/z: 327 (M$^+$). HRMS (EI$^+$) for C18H21N3O3 (M$^+$): calcd, 327.1583; found, 327.1576.

EXAMPLE 99

Step 1.

5(R)-[4-(1-(2-Methyl-1,3-dioxolan-2-yl)cyclopropan-1-yl)phenyl]-5-hydroxymethyloxazolidin-2-one.

The title compound 5(R)-[4-(1-(2-methyl-1,3-dioxolan-2-yl)cyclopropan-1-yl)phenyl]-5-hydroxymethyloxazolidin-2-one (2.55 g) was prepared from 4-benzyloxycarbonylamino-1-(1-(2-methyl-1,3-dioxolan-2-yl)cyclopropan-1-yl)benzene (3.00 g) in the same manner as described for EXAMPLE 1.

MS (EI$^+$) m/z: 319 (M$^+$). HRMS (EI$^+$) for C17H21NO5 (M$^+$): calcd, 319.1420; found, 319.1409.

Step 2.

5(R)-[4-(1-(2-Methyl-1,3-dioxolan-2-yl)cyclopropan-1-yl)phenyl]-5-phenylsulfonyloxymethyloxazolidin-2-one.

To a solution of 5(R)-[4-(1-(2-methyl-1,3-dioxolan-2-yl)cyclopropan-1-yl)phenyl]-5-hydroxymethyloxazolidin-2-one (2.55 g) and triethylamine (1.7 mL) in tetrahydrofuran (20 mL) was added benzenesulfonyl chloride (1.2 mL) at 0° C., the mixture was stirred at room temperature overnight, and heated at 40° C. for 10 hours. After dilution with water, the mixture was extracted with tetrahydrofuran. The organic extracts were washed with 1 N hydrochloric acid, saturated sodium hydrogencarbonate solution and brine, dried over anhydrous magnesium sulfate, filtered, and then concentrated in vacuo. Flash chromatography (silica, hexane:ethyl acetate=1:1) of the residue gave 5(R)-[4-(1-(2-methyl-1,3-dioxolan-2-yl)cyclopropan-1-yl)phenyl]-5-phenylsulfonyloxymethyloxazolidin-2-one (3.05 g).

MS (EI$^+$) m/z: 459 (M$^+$). HRMS (EI$^+$) for C23H25NO7S (M$^+$): calcd, 459.1352; found, 459.1335.

Step 3.

5(R)-Azidomethyl-3-[4-(1-(2-methyl-1,3-dioxolan-2-yl)cyclopropan-1-yl)phenyl]oxazolidin-2-one.

The title compound 5(R)-azidomethyl-3-[4-(1-(2-methyl-1,3-dioxolan-2-yl)cyclopropan-1-yl)phenyl]oxazolidin-2-one (1.49 g) was prepared from 5(R)-[4-(1-(2-methyl-1,3-dioxolan-2-yl)cyclopropan-1-yl)phenyl]-5-phenylsulfonyloxymethyloxazolidin-2-one (2.00 g) in the same manner as described for EXAMPLE 1.

MS (EI$^+$) m/z: 344 (M$^+$). HRMS (EI$^+$) for C17H20N4O4 (M$^+$): calcd, 344.1485; found, 344.1489.

Step 4.

N-[5(S)-3-[4-(1-Acetylcyclopropan-1-yl)phenyl]-2-oxooxazolidin-5-ylmethyl]acetamide.

A suspension of 5(R)-azidomethyl-3-[4-(1-(2-methyl-1,3-dioxolan-2-yl)cyclopropan-1-yl)phenyl]oxazolidin-2-one (1.46 g) and Lindlar catalyst (500 mg) in methanol (20 mL) and dichloromethane (4 mL) was hydrogenated at 1 atm for 2.5 hours at room temperature. After filtration of the catalyst, the filtrate was concentrated in vacuo to give 5(S)-aminomethyl-3-[4-(1-(2-methyl-1,3-dioxolan-2-yl)cyclopropan-1-yl)phenyl]oxazolidin-2-one. To a solution of crude 5(S)-aminomethyl-3-[4-(1-(2-methyl-1,3-dioxolan-2-yl)cyclopropan-1-yl)phenyl]oxazolidin-2-one thus obtained in dichloromethane (20 mL) was added triethylamine (1.2 mL) and acetic anhydride (0.8 mL) at room temperature, and the mixture was stirred at the same temperature for 1 hour, and then concentrated in vacuo. The residue was added acetic acid (30 mL) and water (3 mL), the resulting mixture was stirred at room temperature for 8 hours, and allowed to stand for overnight. After dilution with ethyl acetate, the mixture was washed with saturated sodium hydrogencarbonate solution and brine, dried over anhydrous magnesium sulfate, filtered, and then concentrated in vacuo. Flash chromatography (silica, ethyl acetate:methanol=20:1) of the residue gave N-[5(S)-3-[4-(1-acetylcyclopropan-1-yl)phenyl]-2-oxooxazolidin-5-ylmethyl]acetamide (800 mg).

MS (EI$^+$) m/z: 316 (M$^+$). HRMS (EI$^+$) for C17H20N2O4 (M$^+$): calcd, 316.1423; found, 316.1423.

REFERENCE EXAMPLE 1

2-Fluoro-4-nitrophenylacetic Acid

To a suspension of sodium hydride (32.7 g) in dimethyl sulfoxide (580 mL) was added diethyl malonate (129 mL) at 0° C. for 40 min, and the mixture was stirred at room temperature for 1.5 hours. 3,4-Difluoronitrobenzene (50.0 g) was added the mixture at 0° C., and the resulting solution was stirred at room temperature for 2 hours. The mixture was poured to 10% ammonium chloride solution, and then extracted with ethyl acetate. The organic extracts were washed with water and brine, dried over anhydrous magnesium sulfate, filtered, and then concentrated in vacuo to give diethyl 2-fluoro-4-nitrophenyl malonate. A solution of crude diethyl 2-fluoro-4-nitrophenyl malonate thus obtained in acetic acid (456 mL), water (323 mL) and concentrated sulfuric acid (130 mL) was heated under reflux for 14 hours, and then concentrated in vacuo. After dilution the residue with water, the mixture was extracted with ether. The ethereal solution was extracted with 10% potassium carbonate solution. The aqueous extracts were adjusted to pH 2 by the addition of concentrated hydrochloric acid. The resulting precipitates were collected by filtration, washed with water, and then dried in air to give 2-fluoro-4-nitrophenylacetic acid. MS (EI$^+$) m/z: 199 (M$^+$).

HRMS (EI$^+$) for $C_8H_6FNO_4$ (M$^+$): calcd, 199.0281; found, 199.0308.

REFERENCE EXAMPLE 2 t-Butyl 2-Fluoro-4-nitrophenylacetate

To a solution of 2-fluoro-4-nitrophenylacetic acid (24.0 g) in t-butyl alcohol (450 mL) was added di-t-butyl dicarbonate (29.0 g) and (4-dimethylamino)pyridine (1.47 g) at room temperature, and the mixture was stirred at the same temperature for 2 hours. The mixture was added saturated sodium hydrogencarbonate solution, stirred for 30 min, and then extracted with ethyl acetate. The organic extracts were washed with 5% hydrochloric acid and brine, dried over anhydrous magnesium sulfate, filtered, and then concentrated in vacuo. Flash chromatography (silica, hexane:ethyl acetate=6:1) of the residue gave t-butyl 2-fluoro-4-nitrophenylacetate. MS (FAB$^+$) m/z: 256 (MH$^+$).

HRMS (FAB$^+$) for $C_{12}H_{15}FNO_4$ (MH$^+$): calcd, 256.0985; found, 256.0989.

REFERENCE EXAMPLE 3 t-Butyl 1-(2-Fluoro-4-nitrophenyl)cyclopropane-1-carboxylate

To a solution of t-butyl 2-fluoro-4-nitrophenylacetate (11.3 g) in dimethyl sulfoxide (70 mL) was added bis(dimethylamino)methane (6.80 g) and acetic anhydride (14.9 g) at room temperature, and the mixture was stirred at the same temperature for 30 min. The mixture was poured to water, and the mixture was extracted with toluene. The organic extracts were washed with water and brine, dried over anhydrous magnesium sulfate, filtered, and then concentrated in vacuo. Flash chromatography (silica, hexane:ethyl acetate=9:1) of the residue gave t-butyl 2-(2-fluoro-4-nitrophenyl)acrylate. To a solution of the above t-butyl 2-(2-fluoro-4-nitrophenyl)acrylate and trimethylsulfoxonium iodide (11.7 g) in dimethyl sulfoxide (70 mL) was added potassium t-butoxide (5.96 g) at room temperature, and the mixture was stirred at the same temperature for 1 hour. After quenching the reaction by the addition of 5% hydrochloric acid, the mixture was extracted with ethyl acetate. The organic extracts were washed with 3% sodium thiosulfate solution and brine, dried over anhydrous magnesium sulfate, filtered, and then concentrated in vacuo. Flash chromatography (silica, hexane:ethyl acetate=9:1) of the residue gave t-butyl 1-(2-fluoro-4-nitrophenyl)cyclopropane-1-carboxylate. MS (EI$^+$) m/z: 281 (M$^+$).

HRMS (EI$^+$) for $C_{14}H_{16}FNO_4$ (M$^+$): calcd, 281.1063; found, 281.1088.

REFERENCE EXAMPLE 4 t-Butyl 1-(4-Benzyloxycarbonylamino-2-fluorophenyl)cyclopropane-1-carboxylate

A suspension of t-butyl 1-(2-fluoro-4-nitrophenyl)cyclopropane-1-carboxylate (110 mg) and palladium catalyst (10% on charcoal, 11 mg) in methanol (5 mL) was hydrogenated at 1 atm for 2 hours at room temperature. After filtration of the catalyst, the filtrate was concentrated in vacuo to give t-butyl 1-(4-amino-2-fluorophenyl)cyclopropane-1-carboxylate. To a solution of crude t-butyl 1-(4-amino-2-fluorophenyl)cyclopropane-1-carboxylate thus obtained in tetrahydrofuran (5 mL) was added sodium hydrogencarbonate (39 mg), water (1 mL) and benzyl chloroformate (61 L) at room temperature, and the mixture was stirred at the same temperature for 1 hour. After quenching the reaction by the addition of saturated sodium hydrogencarbonate solution, the mixture was extracted with ethyl acetate. The organic extracts were washed with brine, dried over anhydrous magnesium sulfate, filtered, and then concentrated in vacuo. Flash chromatography (silica, hexane:ethyl acetate=6:1) of the residue gave t-butyl 1-(4-benzyloxycarbonylamino-2-fluorophenyl)cyclopropane-1-carboxylate. MS (EI$^+$) m/z: 385 (M$^+$).

HRMS (EI$^+$) for $C_{22}H_{24}FNO4$ (M$^+$): calcd, 385.1689; found, 385.1693.

REFERENCE EXAMPLE 5

2,6-Difluoro-4-nitrophenylacetic Acid

The title compound 2,6-difluoro-4-nitrophenylacetic acid (16.0 g) was prepared from 3,4,5-trifluoronitrobenzene (14.8 g) and diethyl malonate (35 mL) in the same manner as described for REFERENCE EXAMPLE 1. MS (EI$^+$) m/z: 217 (M$^+$).

HRMS (EI$^+$) for $C_8H_5F_2NO_4$ (M$^+$): calcd, 217.0187; found, 217.0213.

REFERENCE EXAMPLE 6 t-Butyl 2,6-Difluoro-4-nitrophenylacetate

The title compound t-butyl 2,6-difluoro-4-nitrophenylacetate (18.5 g) was prepared from 2,6-difluoro-4-nitrophenylacetic acid (16.0 g) in the same manner as described for REFERENCE EXAMPLE 2.

Rf=0.73 (hexane:ethyl acetate=4:1).

REFERENCE EXAMPLE 7 t-Butyl 2-(2,6-Difluoro-4-nitrophenyl)acrylate

The title compound t-butyl 2-(2,6-difluoro-4-nitrophenyl)acrylate (18.8 g) was prepared from t-butyl 2,6-difluoro-4-nitrophenylacetate (18.5 g) in the same manner as described for REFERENCE EXAMPLE 3. MS (FAB$^+$) m/z: 285 (MH$^+$).

HRMS (FAB$^+$) for $C_{13}H_{14}F_2NO_4$ (MH$^+$): calcd, 285.0891; found, 285.0902.

REFERENCE EXAMPLE 8 t-Butyl 1-(2,6-Difluoro-4-nitrophenyl)cyclopropane-1-carboxylate

The title compound t-butyl 1-(2,6-difluoro-4-nitrophenyl)cyclopropane-1-carboxylate (145 mg) was prepared from t-butyl 2-(2,6-difluoro-4-nitrophenyl)acrylate (200 mg) in the same manner as described for REFERENCE EXAMPLE 3.

MS (EI$^+$) m/z: 299 (M$^+$). HRMS (EI$^+$) for $C_{14}H_{15}F_2NO_4$ (M$^+$): calcd, 299.0969; found, 299.0986.

REFERENCE EXAMPLE 9 t-Butyl 1-(4-Benzyloxycarbonylamino-2,6-difluorophenyl)cyclopropane-1-carboxylate The title compound t-butyl 1-(4-benzyloxycarbonylamino-2,6-difluorophenyl)

cyclopropane-1-carboxylate (14.9 g) was prepared from t-butyl 1-(2,6-difluoro-4-nitrophenyl)cyclopropane-1-carboxylate (12.3 g) in the same manner as described for REFERENCE EXAMPLE 4. MS (EI$^+$) m/z: 403 (M$^+$).

HRMS (EI$^+$) for $C_{14}H_{15}F_2NO_4$ (M$^+$): calcd, 403.1595; found, 403.1586.

REFERENCE EXAMPLE 10

1-(2-Fluoro-4-nitrophenyl)-1-cyclopropylmethanol

The title compound 1-(2-fluoro-4-nitrophenyl)-1-cyclopropylmethanol (20.7 g) was prepared from t-butyl 2-fluoro-4-nitrophenylacetate (30.2 g) in the same manner as described for EXAMPLES 2 and 3. MS (EI$^+$) m/z: 211 (M$^+$).

HRMS (EI$^+$) for $C_{10}H_{10}FNO_3$ (M$^+$): calcd, 211.0645; found, 211.0649.

REFERENCE EXAMPLE 11

1-(2-Fluoro-4-nitrophenyl)-1-cyclopropylcarbonitrile

The title compound 1-(2-fluoro-4-nitrophenyl)-1-cyclopropylcarbonitrile (424 mg) was prepared from 1-(2-fluoro-4-nitrophenyl)-1-cyclopropylmethanol (555 mg) in the same manner as described for EXAMPLES 5, 6 and 7. MS (EI$^+$) m/z: 206 (M$^+$).

HRMS (EI$^+$) for $C_{10}H_7FN_2O_2$ (M$^+$): calcd, 206.0492; found, 206.0512.

REFERENCE EXAMPLE 12

1-(4-Benzyloxycarbonylamino-2-fluorophenyl)-1-cyclopropanecarbonitrile

The title compound 1-(4-benzyloxycarbonylamino-2-fluorophenyl)-1-cyclopropanecarbonitrile (642 mg) was prepared from 1-(2-fluoro-4-nitrophenyl)-1-cyclopropylcarbonitrile (420 mg) in the same manner as described for REFERENCE EXAMPLE 4. MS (EI$^+$) m/z: 310 (M$^+$).

HRMS (EI$^+$) for $C_{18}H_{15}FN_2O_2$ (M$^+$): calcd, 310.1118; found, 310.1122.

REFERENCE EXAMPLE 13

1-(4-Benzyloxycarbonylaminophenyl)-1-cyclopropanecarbonitrile

The title compound 1-(4-benzyloxycarbonylaminophenyl)-1-cyclopropanecarbonitrile (8.34 g) was prepared from 1-(4-nitrophenyl)-1-cyclopropylcarbonitrile (5.50 g) in the same manner as described for REFERENCE EXAMPLE 4. MS (EI$^+$) m/z: 292 (M$^+$).

HRMS (EI$^+$) for $C_{18}H_{16}N_2O_2$ (M$^+$): calcd, 292.1212; found, 292.1190.

REFERENCE EXAMPLE 14

(2-Methyl-4-nitrophenyl)acetonitrile

To a suspension of sodium hydride (60% oil dispersion, 6.13 g) in dimethyl sulfoxide (100 mL) was added ethyl cyanoacetate (18.0 g) at 0° C., and the mixture was stirred at room temperature for 2 hours. 2-Methyl-4-nitrofluorobenzene (9.15 g) was added to the mixture, and the resulting solution was stirred at room temperature for 12 hours. After quenching the reaction by the addition of 6 N hydrochloric acid at 0° C., and the mixture was extracted with ether. The ethereal solution was washed with brine, dried over anhydrous magnesium sulfate, filtered, and then concentrated in vacuo to give ethyl (2-methyl-4-nitrophenyl)cyanoacetate. A solution of crude ethyl (2-methyl-4-nitrophenyl)cyanoacetate thus obtained in dioxane (200 mL) and 6 N hydrochloric acid (200 mL) was heated at 100° C. for 12 hours. After dilution of the mixture with water and sodium chloride, the mixture was extracted with ethyl acetate. The organic extracts were washed with brine, dried over anhydrous magnesium sulfate, filtered, and then concentrated in vacuo. Flash chromatography (silica, hexane:ethyl acetate=2:1) of the residue gave (2-methyl-4-nitrophenyl)acetonitrile (5.32 g).

MS (EI$^+$) m/z: 176 (M$^+$). HRMS (EI$^+$) for C9H8N2O2 (M$^+$): calcd, 176.0586; found, 176.0590.

REFERENCE EXAMPLE 15

1-(2-Methyl-4-nitrophenyl)cyclopropane-1-carbonitrile

A mixture of (2-methyl-4-nitrophenyl)acetonitrile (100 mg), benzyltriethylammonium chloride (129 mg), dibromoethane (73.4 μL) and 50% sodium hydroxide solution was heated at 70° C. for 1 hour. After quenching the reaction by the addition of concentrated hydrochloric acid at 0° C., and the mixture was extracted with ethyl acetate. The organic extracts were washed with brine, dried over anhydrous magnesium sulfate, filtered, and then concentrated in vacuo. Flash chromatography (silica, hexane:ethyl acetate=2:1) of the residue gave 1-(2-Methyl-4-nitrophenyl)cyclopropane-1-carbonitrile (92.1 mg).

MS (EI$^+$) m/z: 202 (M$^+$). HRMS (EI$^+$) for C11H10N2O2 (M$^+$): calcd, 202.0742; found, 202.0727.

REFERENCE EXAMPLE 16

1-(4-Benzyloxycarbonylamino-2-methylphenyl)cyclopropane-1-carbonitrile

The title compound 1-(4-benzyloxycarbonylamino-2-methylphenyl)cyclopropane-1-carbonitrile (5.05 g) was prepared from 1-(2-methyl-4-nitrophenyl)cyclopropane-1-carbonitrile (4.39 g) in the same manner as described for REFERENCE EXAMPLE 4.

MS (EI$^+$) m/z: 306 (M$^+$). HRMS (EI$^+$) for C19H18N2O2 (M$^+$): calcd, 306.1368; found, 306.1397.

REFERENCE EXAMPLE 17

(2-Bromo-4-nitrophenyl)acetonitrile

The title compound (2-bromo-4-nitrophenyl)acetonitrile (1.34 g) was prepared from 2-bromo-4-nitrochlorobenzene (2.36 g) in the same manner as described for REFERENCE EXAMPLE 14.

MS (EI$^+$) m/z: 240 (M$^+$). HRMS (EI$^+$) for C8H5BrN2O2 (M$^+$): calcd, 239.9534; found, 239.9562.

REFERENCE EXAMPLE 18

1-(2-Bromo-4-nitrophenyl)cyclopropane-1-carbonitrile

The title compound 1-(2-bromo-4-nitrophenyl)cyclopropane-1-carbonitrile (29.4 mg) was prepared from (2-bromo-4-nitrophenyl)acetonitrile (50 mg) in the same manner as described for REFERENCE EXAMPLE 15.

MS (EI⁺) m/z: 266 (M⁺). HRMS (EI⁺) for C10H7BrN2O2 (M⁺): calcd, 265.9691; found, 265.9677.

REFERENCE EXAMPLE 19

1-(4-Benzyloxycarbonylamino-2-bromophenyl)cyclopropane-1-carbonitrile

The title compound 1-(4-benzyloxycarbonylamino-2-bromophenyl)cyclopropane-1-carbonitrile (115 mg) was prepared from 1-(2-bromo-4-nitrophenyl)cyclopropane-1-carbonitrile (100 mg) in the same manner as described for REFERENCE EXAMPLE 4.

Rf: 0.57 (silica, hexane:ethyl acetate=2:1).

REFERENCE EXAMPLE 20

4-(1-Acetylcyclopropan-1-yl)nitrobenzene

The title compound 4-(1-acetylcyclopropan-1-yl)nitrobenzene (94.0 mg) was prepared from 4-nitrophenylacetone (100 mg) in the same manner as described for REFERENCE EXAMPLE 15.

MS (EI⁺) m/z: 205 (M⁺). HRMS (EI⁺) for C11H11NO3 (M⁺): calcd, 205.0739; found, 205.0729.

REFERENCE EXAMPLE 21

4-(1-(2-Methyl-1,3-dioxolan-2-yl)cyclooropan-1-yl)nitrobenzene

A solution of 4-(1-acetylcyclopropan-1-yl)nitrobenzene (2.40 g), ethylene glycol (6.5 mL), and pyridinium p-toluenesulfonate (1.47 g) in benzene (120 mL) was heated under reflux with Dean-Stark apparatus for 15 hours. After cooling, dilution with saturated sodium hydrogencarbonate solution, the mixture was extracted with ethyl acetate. The organic extracts were washed with brine, dried over anhydrous magnesium sulfate, filtered, and then concentrated in vacuo. Flash chromatography (silica, hexane:ethyl acetate=4:1) of the residue gave 4-(1-(2-methyl-1,3-dioxolan-2-yl)cyclopropan-1-yl)nitrobenzene (2.83 g).

MS (EI⁺) m/z: 250 (M⁺). HRMS (EI⁺) for C13H16NO4 (M⁺): calcd, 250.1079; found, 250.1089.

REFERENCE EXAMPLE 22

4-Benzyloxycarbonylamino-1-(1-(2-methyl-1,3-dioxolan-2-yl)cyclopropan-1-yl)benzene The title compound 4-benzyloxycarbonylamino-1-(1-(2-methyl-1,3-dioxolan-2-yl)cyclopropan-1-yl)benzene (3.39 g) was prepared from 4-(1-(2-methyl-1,3-dioxolan-2-yl)cyclopropan-1-yl)nitrobenzene (2.50 g) in the same manner as described for REFERENCE EXAMPLE 4.

MS (EI⁺) m/z: 353 (M⁺). HRMS (EI⁺) for C21H23NO4 (M⁺): calcd, 353.1627; found, 353.1623.

The invention has been described with reference to certain preferred embodiments. However, as variations thereon will become obvious to those of skill in the art, the invention is not to be considered as limited thereto.

What is claimed is:

1. A compound of the following formula I:

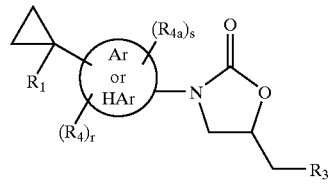

its enantiomer, diastereomer, or pharmaceutically acceptable salt, hydrate or prodrug thereof, wherein:

$R_1$ represents
   i) hydrogen,
   ii) $NR_5NR_6$,
   iii) $CR_7R_8R_9$, $C(R)_2OR_{14}$, $CH_2NHR_{14}$, $C(=O)R_{13}$, $C(=NOH)H$, $C(=NOR_{13})H$, $C(=NOR_{13})R_{13}$, $C(=NOH)R_{13}$, $C(=O)N(R_{13})_2$, $C(=NOH)N(R_{13})_2$, $NHC(=X_1)N(R_{13})_2$, $(C=NH)R_7$, $N(R_{13})C(=X_1)N(R_{13})_2$, $COOR_{13}$, $SO_2R_{14}$, $N(R_{13})SO_2R_{14}$, $N(R_{13})COR_{14}$, or $(C_{1-6}alkyl)CN$, $CN$, $CH=C(R)_2$, $OH$, $C(=O)CHR_{13}$, $C(=NR_{13})R_{13}$, $NHC(=X_1)R_{13}$; or
   iv) $C_{5-10}$ heterocycle optionally substituted with 1–3 groups of $R_7$, which may be attached through either a carbon or a heteroatom;

represents aryl or heteroaryl, heterocycle, heterocyclyl or heterocyclic, provided that in the case of a heteroaryl, heterocycle, heterocyclyl or heterocyclic, the cyclopropyl is not attached to a nitrogen atom on the ring;

$R_3$ represent
   i) $NR_{13}(C=X_2)R_{12}$,
   ii) $NR_{13}(C=X_1)R_{12}$,
   iii) $NR_{13}SO_2R_{14}$,
   iv) $NR_{13}(CHR_{13})_{0-4}aryl$,
   v) $NR_{13}(CHR_{13})_{0-4}heteroaryl$,
   vi) $S(CHR_{13})_{0-4}aryl$,
   vii) $S(CHR_{13})_{0-4}heteroaryl$,
   viii) $O(CHR_{13})_{0-4}aryl$, or
   ix) $O(CHR_{13})_{0-4}heteroaryl$;
   x) $OCR_{13}=NR_{16}$ xi)

$R_4$ and $R_{4a}$ independently represent
   i) hydrogen,
   ii) halogen,
   iii) $C_{1-6}$ alkoxy,
   iv) $C_{1-6}$ alkyl,
   v) CN,
   vi) Aryl, or
   vii) heteroaryl r and s independently are 1–3, with the provision that when $(R_{4a})_s$ and $(R_4)_r$ are attached to an Ar or HAr ring the sum of r and s is less than or equal to 4;

represents an optionally substituted aromatic heterocyclic group containing at least one nitrogen in the ring and which is attached through a bond on any nitrogen, and which is unsubstituted or contains 1 to 3 substituents of $R_{16}$;

$R_5$ and $R_6$ independently represent
i) hydrogen,
ii) $C_{1-6}$ alkyl optionally substituted with 1–3 groups of halogen, CN, OH, $C_{1-6}$ alkoxy, amino, imino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethylenyloxy, or ethynyl, said phenyl and pyridine optionally substituted with 1–3 halogen, CN, OH, $CF_3$, $C_{1-6}$ alkyl or $C_{1-6}$ alkoxy;
iii) $C_{1-6}$ acyl optionally substituted with 1–3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, aralkyloxy, phenyl, pyridine, $C_{1-6}$ alkylcarbonyl, $C_{1-6}$ alkylamino, dialkylamino, $C_{1-6}$ hydroxyacyloxy, $C_{1-6}$ alkylsulfenyl, phthalimido, maleimido, succinimido, said phenoxy, phenyl and pyridine optionally substituted with 1–3 groups of halo, OH, CN, $C_{1-6}$ alkoxy, amino, $C_{1-6}$ acylamino, $CF_3$ or $C_{1-6}$ alkyl;
iv) $C_{1-6}$ alkylsulfonyl optionally substituted with 1–3 groups of halogen, OH, $C_{1-6}$ alkoxy, amino, hydroxylamino, alkoxylamino, $C_{1-6}$ acyloxy, or phenyl; said phenyl optionally substituted with 1–3 groups of halo, OH, $C_{1-6}$ alkoxy, amino, $C_{1-6}$ acylamino, $CF_3$ or $C_{1-6}$ alkyl;
v) arylsulfonyl optionally substituted with 1–3 of halogen, $C_{1-6}$ alkoxy, OH or $C_{1-6}$ alkyl;
vi) $C_{1-6}$ alkoxycarbonyl optionally substituted with 1–3 of halogen, OH, $C_{1-6}$ alkoxy, $C_{1-6}$ acyloxy, or phenyl, said phenyl optionally substituted with 1–3 groups of halo, OH, $C_{1-6}$ alkoxy, amino, $C_{1-6}$ acylamino, $CF_3$ or $C_{1-6}$ alkyl;
vii) aminocarbonyl, $C_{1-6}$ alkylaminocarbonyl or $C_{1-6}$ dialkylaminocarbonyl, said alkyl groups optionally substituted with 1–3 groups of halogen, OH, $C_{1-6}$ alkoxy or phenyl;
viii) five to six membered heterocycles optionally substituted with 1–3 groups of halogen, OH, CN, amino, $C_{1-6}$ acylamino, $C_{1-6}$ alkylsulfonylamino, $C_{1-6}$ alkoxycarbonylamino, $C_{1-6}$ alkoxy, $C_{1-6}$ acyloxy or $C_{1-6}$ alkyl, said alkyl optionally substituted with 1–3 groups of halogen, or $C_{1-6}$ alkoxy;
ix) $C_{3-6}$ cycloalkylcarbonyl optionally substituted with 1–3 groups of halogen, OH, $C_{1-6}$ alkoxy or CN;
x) benzoyl optionally substituted with 1–3 groups of halogen, OH, $C_{1-6}$ alkoxy, $C_{1-6}$ alkyl, $CF_3$, $C_{1-6}$ alkanoyl, amino or $C_{1-6}$ acylamino;
xi) pyrrolylcarbonyl optionally substituted with 1–3 of $C_{1-6}$ alkyl;
xii) $C_{1-2}$ acyloxyacetyl where the acyl is optionally substituted with amino, $C_{1-6}$ alkylamino, $C_{1-6}$ dialkylamino, 4-morpholino, 4-aminophenyl, 4-(dialkylamino)phenyl, 4-(glycylamino)phenyl; or $R_5$ and $R_6$ taken together with any intervening atoms can form a 3 to 7 membered heterocyclic ring containing carbon atoms and 1–2 heteroatoms independently chosen from O, S, SO, $SO_2$, N, or $NR_8$;

$R_7$ represent
hydrogen, halogen, OH, $C_{1-6}$ alkoxy, $C_{1-6}$ alkyl, alkenyl,
amino, $C_{1-6}$ alkylamino, $C_{1-6}$ dialkylamino, hydroxylamino or $C_{1-2}$ alkoxyamino all of which can be optionally substituted on the nitrogen with $C_{1-6}$ acyl, $C_{1-6}$ alkylsulfonyl or $C_{1-6}$ alkoxycarbonyl, said acyl and alkylsulfonyl optionally substituted with 1–2 of halogen or OH;

$R_8$ and $R_8$ independently represents
H, CN,
$C_{1-6}$ alkyl optionally substituted with 1–3 halogen, CN, OH, $C_{1-6}$ alkoxy, $C_{1-6}$ acyloxy, or amino,
phenyl optionally substituted with 1–3 groups of halogen, OH, $C_{1-6}$ alkoxy; or $R_7$ and $R_8$ taken together can form a 3–7 membered carbon ring optionally interrupted with 1–2 heteroatoms chosen from O, S, SO, $SO_2$, NH, and $NR_8$;

$X_1$ represents O, S or $NR_{13}$, NCN, or $NSO_2R_{14}$ $X_2$ represents O, S, NH or $NSO_2R_{14}$;

$R_{10}$ represents hydrogen, $C_{1-6}$ alkyl or $CO_2R_{15}$;

$R_{11}$ represents hydrogen, $C_{1-6}$ alkyl, $C_{1-6}$ alkanoyl, halogen, amino, $C_{1-6}$ cylamino, $C_{1-6}$ alkoxy, OH or $CF_3$,; $NHC_{1-6}$ alkyl, or $N(C_{1-6}$ alkyl$)_2$, where said alkyl may be substituted with 1–3 groups of halo, OH or $C_{1-6}$ alkoxy;

$R_{12}$ represents hydrogen, $C_{1-6}$ alkyl, $C_{3-6}$ cycloalkyl, $NH_2$, heteroaryl, wherein said heteroaryl may be substituted with 1–2 groups of $C_{1-6}$ alkyl, $C_{1-6}$ alkylamino, $C_{1-6}$ alkoxy or $C_{1-6}$ dialkylamino, where said alkyl may be substituted with 1–3 groups of halo, OH, or $C_{1-6}$ alkoxy; alkylthio, alkylsufinyl, alkylsulfonyl, or cyano;

Each $R_{13}$ represents independently hydrogen, $C_{1-6}$ alkyl, $NR_5NR_6$, $SR_8$, $S(O)R_8$, $S(O)_2R_8$, CN, $C_{1-6}$ alkylS(O)R, OH, $C_{1-6}$ alkoxycarbonyl, $C_{6-C10}$ aryl carboxy, hydroxycarbonyl, $C_{1-6}$ acyl, $C_{3-7}$ membered carbon ring optionally interrupted with 1–4 heteroatoms chosen from O, S, SO, $SO_2$, NH and $NR_8$ where said $C_{1-6}$ alkyl or $C_{1-6}$ acyl groups may be independently substituted with 0–3 halogens, hydroxy, $N(R)_2$, $CO_2R$, $C_{6-10}$ aryl, $C_{5-10}$ heteroaryl, or $C_{1-6}$ alkoxy groups;

When two $R_{13}$ groups are attached to the same atom or two adjacent atoms they may be taken together to form a 3–7 membered carbon ring optionally interrupted with 1–2 heteroatoms chosen from O, S, SO, $SO_2$, NH, and $NR_8$;

R represents hydrogen or $C_{1-6}$ alkyl;

$R_{14}$ represents amino, $C_{1-6}$ alkyl, $C_{1-6}$ haloalkyl, five to six membered heterocycles or phenyl, said phenyl and heterocycles optionally substituted with 1–3 group of halo, $C_{1-6}$ alkoxy, $C_{1-6}$ acylamino, or $C_{1-6}$ alkyl, hydroxy and/or amino, said amino and hydroxy optionally protected with an amino or hydroxy protecting group;

$R_{15}$ is $C_{1-6}$ alkyl or benzyl said benzyl optionally substituted with 1–3 groups of halo, OH, $C_{1-6}$ alkoxy, amino, $C_{1-6}$ acylamino, or $C_{1-6}$ alkyl; and $R_{16}$ represents CN, $NH_2$, OH, hydroxy $C_{1-6}$ alkyl, $C_{1-6}$ alkyl, $COOC_{1-6}$ alkyl, COOH, $CONH_2$, $CON(C_{1-6}$ alkyl$)_2$, $CONHC_{1-6}$ alkyl, CHO, C=NOH, C=NO$C_{1-6}$ alkyl, $(CH_2)_{1-3}NH_2$, $(CH_2)_{1-6}$ $NHOC_{1-6}$ alkyl, or $(CH_2)_{1-6}N(C_{1-6}$ alkyl$)_2$, m, n, and q represents 0–1.

2. A compound according to claim 1 wherein $R_1$ independently represent H, $NR_5R_6$, CN, OH, $C(R)_2OR_{14}$, NHC(=X1)N($R_{13}$)$_2$, C(=NOH)N($R_{13}$)$_2$, or $CR_7R_8R_9$.

3. A compound according to claim 1 wherein

is phenyl, pyridine, pyrimidine, or piperidine.

4. A compound according to claim 2 wherein $R_1$ is $NR_5R_6$.

5. A compound according to claim 2 wherein $R_1$ is CN.

6. A compound according to claim 4 wherein $R_5$ and $R_6$ independently are:
  i) hydrogen,
  ii) $C_{1-6}$ alkyl optionally substituted with 1–3 groups of halogen, CN, OH, $C_{1-6}$ alkoxy, amino, imino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethyenyloxy, or ethynyl, said phenyl and pyridine optionally substituted with 1–3 halogen, CN, OH, $CF_3$, $C_{1-6}$ alkyl or $C_{1-6}$ alkoxy;
  iii) $C_{1-6}$ acyl optionally substituted with 1–3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, aralkyloxy, phenyl, pyridine, $C_{1-6}$ alkylcarbonyl, $C_{1-6}$ alkylamino, $C_{1-6}$ dialkylamino, $C_{1-6}$ hydroxyacyloxy, $C_{1-6}$ alkylsulfenyl, phthalimido, maleimido, succinimido, said phenoxy, phenyl and pyridine optionally substituted with 1–3 groups of halo, OH, CN, $C_{1-6}$ alkoxy, amino, $C_{1-6}$ acylamino, $CF_3$ or $C_{1-6}$ alkyl;
  iv) benzoyl optionally substituted with 1–3 groups of halogen, OH, $C_{1-6}$ alkoxy, $C_{1-6}$ alkyl, $CF_3$, $C_{1-6}$ alkanoyl, amino or $C_{1-6}$ acylamino.

7. A compound according to claim 1 wherein $X_1$ represents O.

8. A compound according to claim 1 wherein the structural formula is II:

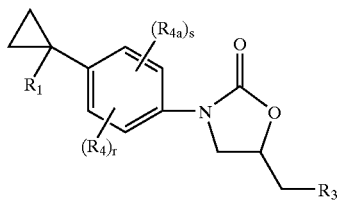

Formula II wherein $R_1$, $R_4$, $R_{4a}$, and $R_3$ are as described herein.

9. A compound according to claim 8 wherein $R_1$ independently represent H, $NR_5R_6$, CN, OH, $C(R)_2OR_{14}$, NHC(=X1)N($R_{13}$)$_2$, C(=NOH)N($R_{13}$)$_2$, or $CR_7R_8R_9$.

10. A compound according to claim 9 wherein $R_1$ is $NR_5R_6$.

11. A compound according to claim 9 wherein $R_1$ is CN.

12. A compound which is:
N-[5(S)-3-[4-[(1-t-Butoxycarbonyl)cyclopropan-1-yl]-3-fluorophenyl]-2-oxooxazolidin-5-ylmethyl]acetamide,
N-[5(S)-3-[4-(1-Carboxycyclopropan-1-yl)-3-fluorophenyl]-2-oxooxazolidin-5-ylmethyl]acetamide,
N-[5(S)-3-[3-Fluoro-4-(1-hydroxymethylcyclopropan-1-yl)phenyl]-2-oxooxazolidin-5-ylmethyl]acetamide,
N-[5(S)-3-[4-(1-Aminocyclopropan-1-yl)-3-fluorophenyl]-2-oxooxazolidin-5-ylmethyl]acetamide,
N-[5(S)-3-[4-(1-Aminocyclopropan-1-yl)-3,5-difluorophenyl]-2-oxooxazolidin-5-ylmethyl]acetamide,
N-[5(S)-3-[4-(1-Aminocyclopropan-1-yl)phenyl]-2-oxooxazolidin-5-ylmethyl]acetamide,
N-[5(S)-3-[3-Fluoro-4-(1-formylcyclopropan-1-yl)phenyl]-2-oxooxazolidin-5-ylmethyl]acetamide,
N-[5(S)-3-[3-Fluoro-4-(1-(hydroxyimino)methylcyclopropan-1-yl)phenyl]-2-oxooxazolidin-5-ylmethyl]acetamide,
N-[5(S)-3-[4-(1-Cyanocyclopropan-1-yl)-3-fluorophenyl]-2-oxooxazolidin-5-ylmethyl]acetamide,
N-[5(S)-3-[4-(1-Cyanocyclopropan-1-yl)-3-fluorophenyl]-2-oxooxazolidin-5-ylmethyl]thioacetamide,
N-[5(S)-3-[4-(1-Cyanocyclopropan-1-yl)-3,5-difluorophenyl]-2-oxooxazolidin-5-ylmethyl]thioacetamide,
N-[5(S)-3-[4-(1-Cyanocyclopropan-1-yl)-3-fluorophenyl]-2-oxooxazolidin-5-ylmethyl]methanesulfonylamide,
N-[5(S)-3-[4-[(1-t-Butoxycarbonyl)cyclopropan-1-yl]-3,5-difluorophenyl]-2-oxooxazolidin-5-ylmethyl]acetamide,
N-[5(S)-3-[3,5-Difluoro-4-(1-hydroxymethylcyclopropan-1-yl)phenyl]-2-oxooxazolidin-5-ylmethyl]acetamide,
N-[5(S)-3-[3,5-Difluoro-4-(1-formylcyclopropan-1-yl)phenyl]-2-oxooxazolidin-5-ylmethyl]acetamide,
N-[5(S)-3-[4-(1-Cyanocyclopropan-1-yl)-3,5-difluorophenyl]-2-oxooxazolidin-5-ylmethyl]acetamide,
N-[5(S)-3-[4-(1-Cyanocyclopropan-1-yl)-3-fluorophenyl]-2-oxooxazolidin-5-ylmethyl]difluoroacetamide,
N-[5(S)-3-[4-(1-Cyanocyclopropan-1-yl)-3,5-difluorophenyl]-2-oxooxazolidin-5-ylmethyl]difluoroacetamide,
N-[5(S)-3-[4-(1-Cyanocyclopropan-1-yl)phenyl]-2-oxooxazolidin-5-ylmethyl]difluoroacetamide,
5(S)-5-[N-(t-Butoxycarbonyl)-N-(1,2,4-oxadiazolyl-3-yl)]-3-[4-(1-cyanocyclopropan-1-yl)-3-fluorophenyl]aminomethyloxazolidin-2-one,
5(S)-5-[N-(t-Butoxycarbonyl)-N-(1,2-isoxadiazolyl-3-yl)]-3-[4-(1-cyanocyclopropan-1-yl)-3-fluorophenyl]aminomethyloxazolidin-2-one,
5(S)-3-[4-(1-Cyanocyclopropan-1-yl)-3-fluorophenyl]-5-[N-(1,2,4-oxadiazolyl-3-yl)amino]methyloxazolidin-2-one,
5(S)-3-[4-(1-Cyanocyclopropan-1-yl)-3,5-difluorophenyl]-5-[N-(1,2,4-oxadiazolyl-3-yl)amino]methyloxazolidin-2-one,
5(S)-3-[4-(1-Cyanocyclopropan-1-yl)-3-fluorophenyl]-5-[N-(1,2,3,4-thiatriazolyl-5-yl)amino]methyloxazolidin-2-one,
5(S)-3-[4-(1-Cyanocyclopropan-1-yl)-3,5-difluorophenyl]-5-[N-(1,2,3,4-thiatriazolyl-5-yl)amino]methyloxazolidin-2-one,
5(S)-3-[4-(1-Cyanocyclopropan-1-yl)phenyl]-5-[N-(1,2,3,4-thiatriazolyl-5-yl)amino]methyloxazolidin-2-one, 5(S)-3-[4-(1-Cyanocyclopropan-1-yl)-3-fluorophenyl]-5-[N-(1,2-isoxadiazolyl-3-yl)amino]methyloxazolidin-2-one, (S)-3-[4-(1-Cyanocyclopropan-1-yl)-3,5-difluorophenyl]-5-[N-(1,2-isoxadiazolyl-3-yl)amino]methyloxazolidin-2-one, N-[5(S)-3-[4-(1-Cyanocyclopropan-1-yl)phenyl]-2-oxooxazolidin-5-ylmethyl]acetamide, N-[5(S)-3-[4-(1-Cyanocyclopropan-1-yl)phenyl]-2-oxooxazolidin-5-ylmethyl]thioacetamide, 5(S)-5-[N-(t-Butoxycarbonyl)-N-(1,2,4-oxadiazolyl-3-yl)]-3-[4-(1-cyanocyclopropan-1-yl)phenyl]aminomethyloxazolidin-2-one, 5(S)-5-[N-(t-Butoxycarbonyl)-N-(1,2-isoxadiazolyl-3-yl)]-3-[4-(1-cyanocyclopropan-1-yl)phenyl]aminomethyloxazolidin-2-one, 5(S)-3-[4-(1-Cyanocyclopropan-1-yl)phenyl]-5-[N-(1,2,4-oxadiazolyl-3-yl)amino]methyloxazolidin-2-one, 5(S)-3-[4-(1-Cyanocyclopropan-1-yl)phenyl]-5-[N-(1,2-isoxadiazolyl-3-yl)amino]methyloxazolidin-2-one, 5(R)-3-[4-(1-Cyanocyclopropan-1-yl)phenyl]-5-[N-(1,2-isoxadiazolyl-3-yl)oxy]methyloxazolidin-2-one, 5(S)-5-[N-(t-Butoxycarbonyl)-N-(1,3-thiazolyl-2-yl)]-3-[4-(1-cyanocyclopropan-1-yl)phenyl]aminomethyloxazolidin-2-one, 5(S)-5-[N-(t-Butoxycarbonyl)-N-(1,3,4-thiadiazolyl-2-yl)]-3-[4-(1-cyanocyclopropan-1-yl)phenyl]aminomethyloxazolidin-2-one, 5(S)-3-[4-(1-Cyanocyclopropan-1-yl)phenyl]-5-[N-(1,3-thiazolyl-2-yl)amino]methyloxazolidin-2-one, 5(S)-3-[4-(1-Cyanocyclopropan-1-yl)-3-fluorophenyl]-5-[N-(1,3-thiazolyl-2-yl)amino]methyloxazolidin-2-one, 5(S)-3-[4-(1-Cyanocyclopropan-1-yl)-3,5-difluorophenyl]-5-[N-(1,3-thiazolyl-2-yl)amino]methyloxazolidin-2-one, 5(S)-3-[4-(1-Cyanocyclopropan-1-yl)phenyl]-5-[N-(1,3,4-thiadiazolyl-2-yl)amino]methyloxazolidin-2-one, S-Methyl N-[5(S)-3-[4-(1-Cyanocyclopropan-1-yl)-3-fluorophenyl]-2-oxooxazolidin-5-ylmethyl]dithiocarbamate, S-Methyl N-[5(S)-3-[4-(1-Cyanocyclopropan-1-yl)-3,5-difluorophenyl]-2-oxooxazolidin-5-ylmethyl]dithiocarbamate, S-Methyl N-[5(S)-3-[4-(1-Cyanocyclopropan-1-yl)phenyl]-2-oxooxazolidin-5-ylmethyl]dithiocarbamate, N-[5(S)-3-[4-(1-Cyanocyclopropan-1-yl)-3-fluorophenyl]-2-oxooxazolidin-5-ylmethyl]thiourea, N-[5(S)-3-[4-(1-Cyanocyclopropan-1-yl)-3,5-fluorophenyl]-2-oxooxazolidin-5-ylmethyl]thiourea, N-[5(S)-3-[4-(1-Cyanocyclopropan-1-yl)phenyl]-2-oxooxazolidin-5-ylmethyl]thiourea, O-Methyl N-[5(S)-3-[4-(1-Cyanocyclopropan-1-yl)-3-fluorophenyl]-2-oxooxazolidin-5-ylmethyl]thiocarbonate, O-Methyl N-[5(S)-3-[4-(1-Cyanocyclopropan-1-yl)-3,5-difluorophenyl]-2-oxooxazolidin-5-ylmethyl]thiocarbonate, N'-Methyl N-[5(S)-3-[4-(1-Cyanocyclopropan-1-yl)-3-fluorophenyl]-2-oxooxazolidin-5-ylmethyl]thiourea, N'-Methyl N-[5(S)-3-[4-(1-Cyanocyclopropan-1-yl)-3,5-difluorophenyl]-2-oxooxazolidin-5-ylmethyl]thiourea, N'-Methyl N-[5(S)-3-[4-(1-Cyanocyclopropan-1-yl)phenyl]-2-oxooxazolidin-5-ylmethyl]thiourea, O-Methyl N-[5(S)-3-[4-(1-Cyanocyclopropan-1-yl)phenyl]-2-oxooxazolidin-5-ylmethyl]thiocarbonate, N'-Cyano N-[5(S)-3-[4-(1-Cyanocyclopropan-1-yl)phenyl]-2-oxooxazolidin-5-ylmethyl]acetamidine, N'-Cyano N-[5(S)-3-[4-(1-Cyanocyclopropan-1-yl)-3-fluorophenyl]-2-oxooxazolidin-5-ylmethyl]acetamidine, or its enantiomer, diastereomer, or pharmaceutically acceptable salt, hydrate or prodrug thereof.

13. A compound which is:

1-[5(R)-3-[4-(1-Cyanocyclopropan-1-yl)phenyl]-2-oxooxazolidin-5-ylmethyl]-1,2,3-triazole, 5-Amino-4-cyano-1-[5(R)-3-[4-(1-cyanocyclopropan-1-yl)phenyl]-2-oxooxazolidin-5-ylmethyl]-1,2,3-triazole, 1-[5(R)-3-[4-(1-Cyanocyclopropan-1-yl)phenyl]-2-oxooxazolidin-5-ylmethyl]-5-methyl-1,2,3-triazole, 1-[5(R)-3-[4-(1-Cyanocyclopropan-1-yl)phenyl]-2-oxooxazolidin-5-ylmethyl]-4-methyl-1,2,3-triazole, 1-[5(R)-3-[4-(1-Cyanocyclopropan-1-yl)-3-fluorophenyl]-2-oxooxazolidin-5-ylmethyl]-1,2,3-triazole, 1-[5(R)-3-[4-(1-Cyanocyclopropan-1-yl)phenyl]-2-oxooxazolidin-5-ylmethyl]-1,2,5-triazole, 5(R)-3-[4-[(1-Cyanocyclopropan-1-yl)phenyl]-5-methanesulfonyloxymethyloxazolidin-2-one, 1-[5(R)-3-[4-(1-Cyanocyclopropan-1-yl)phenyl]-2-oxooxazolidin-5-ylmethyl]-1,2,5-triazole, 1-[5(R)-3-[4-(1-Cyanocyclopropan-1-yl)phenyl]-2-oxooxazolidin-5-ylmethyl]-1,2,4-triazole, 1-[5(R)-3-[4-(1-Cyanocyclopropan-1-yl)phenyl]-2-oxooxazolidin-5-ylmethyl]-1,2-prazole, 2-[5(R)-3-[4-(1-Cyanocyclopropan-1-yl)phenyl]-2-oxooxazolidin-5-ylmethyl]tetrazole, 1-[5(R)-3-[4-(1-Cyanocyclopropan-1-yl)phenyl]-2-oxooxazolidin-5-ylmethyl]-1,3-imidazole, 1-[5(R)-3-[4-(1-Cyanocyclopropan-1-yl)phenyl]-2-oxooxazolidin-5-ylmethyl]tetrazole, 1-[5(R)-3-[4-(1-Cyanocyclopropan-1-yl)phenyl]-2-oxooxazolidin-5-ylmethyl]-4-hydroxymethyl-1,2,3-triazole and 1-[5(R)-3-[4-(1-cyanocyclopropan-1-yl)phenyl]-2-oxooxazolidin-5-ylmethyl]-5-hydroxymethyl-1,2,3-triazole, t-Butyl 1-[5(R)-3-[4-(1-Cyanocyclopropan-1-yl)phenyl]-2-oxooxazolidin-5-ylmethyl]-1,2,3-triazole-4-carboxylate, 1-[5(R)-3-[4-(1-Cyanocyclopropan-1-yl)phenyl]-2-oxooxazolidin-5-ylmethyl]-1,2,3-triazole-4-carboxylic Acid, 1-[5(R)-3-[4-(1-Cyanocyclopropan-1-yl)phenyl]-2-oxooxazolidin-5-ylmethyl]-1,2,3-triazole-4-carboxamide, 1-[5(R)-3-[4-(1-Cyanocyclopropan-1-yl)phenyl]-2-oxooxazolidin-5-ylmethyl]-N-methyl-1,2,3-triazole-4-carboxamide, 1-[5(R)-3-[4-(1-cyanocyclopropan-1-yl)phenyl]-2-oxooxazolidin-5-ylmethyl]-N,N-dimethyl-1,2,3-triazole-4-carboxamide, 1-[5(R)-3-[4-(1-Cyanocyclopropan-1-yl)phenyl]-2-oxooxazolidin-5-ylmethyl]-1,2,3-triazole-4-carboxaldehyde, 1-[5(R)-3-[4-(1-Cyanocyclopropan-1-yl)phenyl]-2-oxooxazolidin-5-ylmethyl]-4-(hydroxyimino)methyl-1,2,3-triazole, 4-Cyano-1-[5(R)-3-[4-(1-cyanocyclopropan-1-yl)phenyl]-2-oxooxazolidin-5-ylmethyl]-1,2,3-triazole, 1-[5(R)-3-[4-(1-Cyanocyclopropan-1-yl)phenyl]-2-oxooxazolidin-5-ylmethyl]-4-(methoxyimino)methyl-1,2,3-triazole, 4-Aminomethyl-1-[5(R)-3-[4-(1-cyanocyclopropan-1-yl)phenyl]-2-oxooxazolidin-5-ylmethyl]-1,2,3-triazole, 4-Azidomethyl-1-[5(R)-3-[4-(1-cyanocyclopropan-1-yl)phenyl]-2-oxooxazolidin-5-ylmethyl]-1,2,3-triazole, 4-Aminomethyl-1-[5(R)-3-[4-(1-cyanocyclopropan-1-yl)phenyl]-2-oxooxazolidin-5-ylmethyl]-1,2,3-triazole, 4-Acetoamidomethyl-1-[5(R)-3-[4-(1-cyanocyclopropan-1-yl)phenyl]-2-oxooxazolidin-5-ylmethyl]-1,2,3-triazole, 1-[5(R)-3-[4-(1-Cyanocyclopropan-1-yl)phenyl]-2-oxooxazolidin-5-ylmethyl]-4-dimethylaminomethyl-1,2,3-triazole, 1-[5(R)-3-[4-(1-Cyanocyclopropan-1-yl)phenyl]-2-oxooxazolidin-5-ylmethyl]-4-methanesulfonyloxymethyl-1,2,3-triazole, 1-[5(R)-3-[4-(1-Cyanocyclopropan-1-yl)phenyl]-2-oxooxazolidin-5-ylmethyl]-4-dimethylaminomethyl-1,2,3-triazole, N-[5(S)-3-[4-(1-Cyanocyclopropan-1-yl)phenyl]-2-oxooxazolidin-5-ylmethyl]difluoroacetamide, 5(S)-Aminomethyl-3-[4-(1-cyanocyclopropan-1-yl)phenyl]oxazolidin-2-one, N-[5(S)-3-[4-(1-Cyanocyclopropan-1-yl)phenyl]-2-oxooxazolidin-5-ylmethyl]difluoroacetamide, N-[5(S)-3-[4-(1-Cyanocyclopropan-1-yl)phenyl]-2-oxooxazolidin-5-ylmethyl]cyclopropanecarboxamide, N-[5(S)-3-[4-(1-Cyanocyclopropan-1-yl)phenyl]-2-oxooxazolidin-5-ylmethyl]methoxyacetamide, N-[5(S)-3-[4-(1-Cyanocyclopropan-1-yl)phenyl]-2-oxooxazolidin-5-ylmethyl]furan-3-carboxamide, N-[5(S)-3-[4-(1-Cyanocyclopropan-1-yl)phenyl]-2-oxooxazolidin-5-ylmethyl]pyrazine-2-carboxamide, N-[5(S)-3-[4-(1-Cyanocyclopropan-1-yl)phenyl]-2-oxooxazolidin-5-ylmethyl]isoxazole-5-carboxamide, N-[5(S)-3-[4-(1-Cyanocyclopropan-1-yl)phenyl]-2-oxooxazolidin-5-ylmethyl]-1,2,5-thiadiazole-3-carboxamide, N-[5(S)-3-[4-(1-Cyanocyclopropan-1-yl)phenyl]-2-oxooxazolidin-5-ylmethyl]-(4-methyl-1,3-thiazole)-5-carboxamide, N-[5(S)-3-[4-(1-Cyanocyclopropan-1-yl)phenyl]-2-oxooxazolidin-5-ylmethyl]formamide, N-[5(S)-3-[4-(1-Cyanocyclopropan-1-yl)phenyl]-2-oxooxazolidin-5-ylmethyl]propionamide, 5(S)-3-[4-(1-Cyanocyclopropan-1-yl)phenyl]-5-[N-(methoxycarbonyl)]aminomethyloxazolidin-2-one, N-[5(S)-3-[4-(1-Cyanocyclopropan-1-yl)phenyl]-2-oxooxazolidin-5-ylmethyl]dichloroacetamide, N-[5(S)-3-[4-(1-Cyanocyclopropan-1-yl)phenyl]-2-oxooxazolidin-5-ylmethyl]methylthioacetamide, N-[5(S)-3-[4-(1-Cyanocyclopropan-1-yl)phenyl]-2-oxooxazolidin-5-ylmethyl]cyanoacetamide, N-[5(S)-3-[4-(1-Cyanocyclopropan-1-yl)phenyl]-2-oxooxazolidin-5-ylmethyl]methylsulfonylacetamide, N-[5(S)-3-[4-(1-Cyanocyclopropan-1-yl)phenyl]-2-oxooxazolidin-5-ylmethyl]-(2,2-dichloro)cyclopropane-1-carboxamide (diastereomers A and B), N-[5(S)-3-[4-(1-Cyanocyclopropan-1-yl)phenyl]-2-oxooxazolidin-5-ylmethyl]methylsulfinylacetamide, N-[5(S)-3-[4-(1-Cyanocyclopropan-1-yl)phenyl]-2-oxooxazolidin-5-ylmethyl]-2(R)-chloropropionamide, N-[5(S)-3-[4-(1-Cyanocyclopropan-1-yl)phenyl]-2-oxooxazolidin-5-ylmethyl]-2(S)-chloropropionamide, N-[5(S)-3-[4-(1-Cyanocyclopropan-1-yl)phenyl]-2-oxooxazolidin-5-ylmethyl]-N-methylacetamide, N-Benzoyloxy-N-[5(S)-3-[4-(1-cyanocyclopropan-1-yl)phenyl]-2-oxooxazolidin-5-ylmethyl]acetamide and N-benzoyloxy-O-[5(S)-3-[4-(1-cyanocyclopropan-1-yl)phenyl]-2-oxooxazolidin-5-ylmethyl]acetimidate, N-[5(S)-3-[4-(1-Cyanocyclopropan-1-yl)phenyl]-2-oxooxazolidin-5-ylmethyl]-N-hydroxyacetamide, O-[5(S)-3-[4-(1-Cyanocyclopropan-1-yl)phenyl]-2-oxooxazolidin-5-ylmethyl]-N-hydroxyacetimidate, N-[5(S)-3-[4-(1-Cyanocyclopropan-1-yl)-3-fluorophenyl]-2-oxooxazolidin-5-ylmethyl]-1-cyanocyclopropane-1-carboxamide, N-[5(S)-3-[4-(1-Cyanocyclopropan-1-yl)-3-fluorophenyl]-2-oxooxazolidin-5-ylmethyl]-1-hydroxycyclopropane-1-carboxamide, N'-Cyano-N-[5(S)-3-[4-(1-cyanocyclopropan-1-yl)phenyl]-2-oxooxazolidin-5-ylmethyl]-S-methylisothiourea, N'-Cyano-N-[5(S)-3-[4-(1-cyanocyclopropan-1-yl)phenyl]-2-oxooxazolidin-5-ylmethyl]urea, 5(S)-5-[N-(t-Butoxycarbonyl)-N-(pyridin-2-yl)]aminomethyl-3-[4-(1-cyanocyclopropan-1-yl)phenyl]oxazolidin-2-one, 5(S)-3-[4-(1-Cyanocyclopropan-1-yl)phenyl]-5-[N-(pyridin-2-yl)]aminomethyloxazolidin-2-one, N-[5(S)-3-[4-(1-Cyanocyclopropan-1-yl)-3-methylphenyl]-2-oxooxazolidin-5-ylmethyl]acetamide, 5(R)-3-[4-(1-Cyanocyclopropan-1-yl)-3-methylphenyl]-5-hydroxymethyloxazolidin-2-one, 5(R)-Azidomethyl-3-[4-(1-cyanocyclopropan-1-yl)-3-methylphenyl]oxazolidin-2-one, 5(S)-Aminomethyl-3-[4-(1-cyanocyclopropan-1-yl)-3-methylphenyl]oxazolidin-2-one, N-[5(S)-3-[4-(1-Cyanocyclopropan-1-yl)-3-methylphenyl]-2-oxooxazolidin-5-ylmethyl]acetamide, N-[5(S)-3-[4-(1-Cyanocyclopropan-1-yl)]-3-methylphenyl]-2-oxooxazolidin-5-ylmethyl]propionamide, 5(R)-3-[3-Bromo-4-(1-Cyanocyclopropan-1-yl)phenyl]-5-hydroxymethyloxazolidin-2-one, 5(R)-Azidomethyl-3-[3-bromo-4-(1-cyanocyclopropan-1-yl)phenyl]oxazolidin-2-one, N-[5(S)-3-[3-Bromo-4-(1-Cyanocyclopropan-1-yl)phenyl]-2-oxooxazolidin-5-ylmethyl]acetamide, N-[5(S)-3-[3-Cyano-4-(1-cyanocyclopropan-1-yl)phenyl]-2-oxooxazolidin-5-ylmethyl]acetamide, N-[5(S)-3-[4-(1-Cyanocyclopropan-1-yl)-3-phenylphenyl]-2-oxooxazolidin-5-ylmethyl]acetamide, N-[5(S)-3-[4-(1-Cyanocyclopropan-1-yl)-3-(pyridin-3-yl)phenyl]-2-oxooxazolidin-5-ylmethyl]acetamide and N-[5(S)-3-[4-(1-cyanocyclopropan-1-yl)-3-ethylphenyl]-2-oxooxazolidin-5-ylmethyl]acetamide, 5(R)-[4-(1-(2-Methyl-1,3-dioxolan-2-yl)cyclopropan-1-yl)phenyl]-5-hydroxymethyloxazolidin-2-one, 5(R)-[4-(1-(2-Methyl-1,3-dioxolan-2-yl)cyclopropan-1-yl)phenyl]-5-phenylsulfonyloxymethyloxazolidin-2-one, 5(R)-Azidomethyl-3-[4-(1-(2-methyl-1,3-dioxolan-2-yl)cyclopropan-1-yl)phenyl]oxazolidin-2-one, N-[5(S)-3-[4-(1-Acetylcyclopropan-1-yl)phenyl]-2-oxooxazolidin-5-ylmethyl]acetamide.

14. A pharmaceutical composition comprised of a compound in accordance with claim 1 in combination with a pharmaceutically acceptable carrier.

15. A pharmaceutical composition produced by combining a compound in accordance with claim 1 with a pharmaceutically acceptable carrier.

16. A method of treating a bacterial infection in a mammalian patient in need thereof, comprising administering to said patient an effective amount of a compound of claim 1.

17. A method for the preparation of a compound of claim 1, wherein $R_1$ is an ester and the $R_3$ is OH, the method comprising:
1) reacting a nitro substituted aryl, heteroaryl, heterocycle, or heterocyclic nucleus having a leaving group substituent with an acyclic diester in the presence of a base followed by hydrolysis of the resulting diester and decarboxylation under acidic conditions to form the nitro substituted nucleus acetic acid;
2) esterifying the acetic acid product from step 1) to form the corresponding acetic acid ester;
3) reacting the acetic acid ester from step 2) with formaldehyde or equivalent to form the acrylate from the ester, and cyclizing the acrylate to form the 1,1-substituted cyclopropane; and
4) reducing the nitro substituted cyclopropane amino compound and acylating the amine to form a carbobenzoxy or acyloxy substituted amine.

18. A method according to claim 17, wherein the product from step 4) is deprotonated with a base and reacted with an ester to form the hydroxyoxazolidinone.

19. A method according to claim 17, wherein the acrylate is formed in step 3) by reaction of the acetic acid ester with formaldehyde or formaldehyde equivalent in a nonprotic polar solvent in the presence of an anhydride.

20. A method according to claim 17, wherein the acrylate in step 3) is cyclized to the cyclopropane by reaction with an ylide precursor.

21. A method according to claim 18, wherein the ester is a R-glycidyl ester or an S-glycidyl ester.

22. A method for the preparation of a compound of claim 1, wherein $R_1$ is a cyano and the $R_3$ is OH, the method comprising:
1) reacting a nitro substituted aryl, heteroaryl, heterocycle, or heterocyclic nucleus having a leaving group substituent with an acyclic diester in the presence of a base followed by hydrolysis of the resulting diester and decarboxylation under acidic conditions to form the nitro substituted nucleus acetic acid;
2) esterifying the acetic acid product from step 1) to form the corresponding acetic acid ester;
3) reacting the acetic acid ester from step 2) with a formaldehyde or formaldehyde equivalent to form the acrylate from the ester, and cyclizing the acrylate to form the 1,1-acetic acid ester cyclopropane;
4) converting the ester from step 3) to the corresponding cyano compound; and
5) reducing the nitro group to the amino compound and acylating the amine to form a carbo benzoxy or acyloxy substituted amine.

23. A method according to claim 22, wherein the product from step 5) is deprotonated with a base and reacted with an ester to form the hydroxyoxazolidinone.

24. A method according to claim 22, wherein the acrylate is formed in step 3) by reaction of the acetic acid ester with formaldehyde or formaldehyde equivalent in a nonprotic polar solvent in the presence of an anhydride.

25. A method according to claim 22, wherein the acrylate in step 3) is cyclized to the cyclopropane by reaction with an ylide precursor.

26. A method according to claim 23, wherein the ester is a R-glycidyl ester or an S-glycidyl ester.

27. A method according to claim 22, wherein the ester is converted in step 4) to the cyano group by hydrolyzing the ester to the acid, reducing to the carbinol, oxidizing to the aldehyde, forming the oxime, and dehydrating to the cyano compound.

28. A method for the preparation of a compound of claim 1, where $R_1$ is CN or an ester and R3 is a triazole, which comprises:
1) reaction of a 1,1-CN or ester substituted aryl, heteroaryl, heterocycle or heterocyclic nucleus which contains a hydroxymethyloxazolidinone substituent with a reagent to convert the hydroxyl group to a leaving group;
2) converting the leaving group on the compound from step 1) to an azidomethyl substituent;
3) converting the azidomethyl substituent from step 2) to an amine; and
4) reacting the amine compound of step 3) with reactants to add to proximal and distal nitrogens of the azide and form substituted triazoles.

29. A method according to claim 28, wherein the leaving group formed in step 1) is a mesylate, tosylate, benzenesulfonate, or a halide.

30. A method for the preparation of a compound of claim 1, where $R_1$ is CN or an ester and R3 is an acyl group, which comprises:
1) reaction of a 1,1-CN or ester substituted aryl, heteroaryl, heterocycle or heterocyclic nucleus which contains a hydroxymethyloxazolidinone substituent, with a reagent to convert the hydroxyl group to a leaving group;
2) converting the leaving group on the compound from step 1) to an azidomethyl substituent;
3) converting the azidomethyl substituent from step 2) to an amine; and
4) reacting the amine compound of step 3) with an acylating reactant to acylate the amine.

31. A method according to claim 30, wherein the leaving group formed in step 1) is a mesylate, tosylate, benzenesulfonate, or a halide.

32. A method according to claim 30, wherein the acylating agent is selected from the group consisting of acetic anhydride, difluoroacetic anhydride, trifluoroacetic anhydride, bis-2-(1H)-hydroxypyridine thiocarbonate, methylisothiocyanate, O-methyl-N-cyanoacetamide, propionic anhydride, methylchloroformate, dichloroacetylchloride, N-cyanodithioiminocarbonate, sulfonyl chlorides, methane sulfonyl chloride, and carboxylic acids.

* * * * *